US 7,557,187 B2

(12) United States Patent
Caput et al.

(10) Patent No.: US 7,557,187 B2
(45) Date of Patent: Jul. 7, 2009

(54) PURIFIED SR-P70 PROTEIN

(75) Inventors: Daniel Caput, Avignonet Lauragais (FR); Pascual Ferrara, Saint Léon. Haute-Garonne (FR); Ahmed Mourad Kaghad, Montgiscard (FR)

(73) Assignee: sanofi-aventis, Paris (FR)

( * ) Notice: Subject to any disclaimer, the term of this patent is extended or adjusted under 35 U.S.C. 154(b) by 221 days.

(21) Appl. No.: 11/122,636

(22) Filed: May 5, 2005

(65) Prior Publication Data

US 2005/0202016 A1    Sep. 15, 2005

Related U.S. Application Data

(63) Continuation of application No. 09/125,005, filed as application No. PCT/FR97/00214 on Feb. 3, 1997, now abandoned.

(30) Foreign Application Priority Data

Feb. 2, 1996    (FR) .................................. 96 01309

(51) Int. Cl.
*C07K 14/00* (2006.01)
*A61K 38/16* (2006.01)
(52) U.S. Cl. ...................... 530/350; 530/358
(58) Field of Classification Search .................. None
See application file for complete search history.

(56) References Cited

U.S. PATENT DOCUMENTS 5,532,348 A    7/1996    Huibregise et al.
6,451,979 B1   9/2002    Kaelin et al.

FOREIGN PATENT DOCUMENTS

| EP | 0 377 295 | 7/1990 |
| WO | WO94/01563 | 1/1994 |
| WO | WO94/08241 | 4/1994 |
| WO | WO99/66946 | 12/1999 |

OTHER PUBLICATIONS

Dequiedt et al. (DNA Seq, 1995,5: 261-264, See Score 20060927_162151_us-11-122-636-6_copy_110_310.rup database sequence search, Result 38).*
Bowie et al (Science, 1990, 257:1306-1310).*
Burgess et al (J of Cell Bio. 111:2129-2138, 1990).*
Lazar et al. (Molecular and Cellular Biology, 1988, 8:1247-1252).*
Scott et al (Nature Genetics, 1999, 21:440-443).*
Bork (Genome Research, 2000,10:398-400).*
Kaghad et al. (Cell 90:809-819, Aug. 22, 1997).*
Alberts et al., Molecular Biology of the Cell, 3rd ed., 1994, p. 465.
Arai et al., Immunologically distinct p53 molecules generated by alternative splicing, Mol. Cell. Biol., Sep. 1986, vol. 6. No. 9, pp. 3232-3239.
B. Curti, Physical barriers to drug delivery in tumors, Critical Reviews in Oncology/Hematology, 1993, pp. 29-39.

Benedict et al., The Long Isoform of Terminal Deoxynucleotidyl Transferase Enters the Nucleus and, Rather than Catalyzing Nontemplated Nucleotide . . . J. of Exp. Medicine, 2001, vol. 193, No. 1., pp. 89-99.
Bodrug et al., Molecular analysis of a constitutional X-autosome translocation in a female with muscular dystrophy, Science. vol. 237, 1987, pp. 1620-1624.
Bowie et al., Deciphering the Message in Protein Sequences: Tolerance to Amino Acid Substitutions, Science, 1990, vol. 247, pp. 1306-1310.
Burgess et al., Possible Dissociation oi the Heparin-binding and Mitogenic Activities of Heparin-binding (Acidic FibroblastP Growth Factor-1 . . . , J. Cell Biol., 1990, vol. 111, p. 2129-2138.
Dequiedt et al., DNA Seq. 5, 1995, pp. 255-259.
Frasca et al., p73 Tumor-Suppressor Activity Is Impaired in Human Thyroid Cancer, Cancer Research, vol. 63, Sep. 15, 2003, pp. 5829-5837.
Fu et al., Translational regulation of human p53 g in Expression, EMBO Journal, 1996, vol. 15, pp. 4392-4401.
H. Drexler, Recent Results on the Biology of Hodgkin and Reed-Sternberg cells, Leukemia and Lymphoma, 1993, vol. 9, pp. 1-25.
Hartwell et al., Integrating Genetic Approaches into the Discovery of Anticancer Drugs, Science, Nov. 7, 1997, vol. 278, pp. 1064-1068.
Hirashima et al., Ecalectin/Galectin-9, a Novel Eosinophil Chemoattractant: Its Function and Production, Int. Arch. Allergy Immunol., 2000, Suppl. 1, pp. 6-9.
Ikawa et al., p53 family genes: structural comparison, expression and mutation, Cell Death and Differentiation, 1999, vol. 6, pp. 1154-1161.
Iwase et al., Identification of protein-tyrosine kinase gnes preferentially expressed in embryo stomach and gastric cancer, Biochem Biophys Res. Commun.
Jansen et al., Translational Control of Gene Expression, Pediatric Res. 1995, vol. 37, No. 6, pp. 681-686.
Jiang et al., Smooth Muscle Tissues Express a Major Dominant Negative Spice Varian of the Type 3 Ca2= Release Channel (Ryanodine Receptor), J. of Bio. Chem., 2003, vol. 278, No. 7, pp. 4763-4769.
Lazar et al., Transforming Growth Factor alpha: Mutation of Aspartic Acid 47 and Leucine 48 Results in Different Biological Activities, Mol. & Cell. Biol., Mar. 1988, vol. 8, No. 3, pp. 1247-1252.
M. Embleton, Monoclonal Antibodies To Osteogenic Sarcoma Antigens, Immunol. Ser. 1984, pp. 181-207.
McClean et al., Evidence of Post-translational Regulation of P-Glycoprotein Associated with the Expression of A Distinctive Multiple Drug-resistant Phenotype in Chinese Hamster Ovary Cells, Eur. J. Cancer, 1993, vol. 29A, pp. 2243-2248.

(Continued)

*Primary Examiner*—Karen A Canella
*Assistant Examiner*—Peter J Reddig

(57) ABSTRACT

The invention relates to new nucleic acid sequences of the family of tumour-suppressing genes related to the gene for the p53 protein, and to the corresponding protein sequences.

6 Claims, 36 Drawing Sheets

OTHER PUBLICATIONS

Neumann et al., Multifactorial inheritance of neural tube defects: localization of the major gene and recognition of modifiers in ct mutant mice, Nature Genetics, 1994, vol. 6, pp. 357-362.

P. Bork, Powers and Pitfalls in Sequence Analysis: the 70% Hurdle, Genome Research. 2000, vol. 10, pp. 398-400.

Puig et al., p73 Expressio in Human Normal and Tumor Tissues: Loss of p73 aipa Expression is Associated with Tumor Progession in Bladder Cancer, Cancer Research, Nov. 15, 2003, vol. 9, pp. 5652-5651.

R. Jain. Barriers to Drug Delivery in Solid Tumors, Scientific American, Jul. 1994, pp. 58-65.

Shantz et al., Translational regulation of ornithine decarboxylase and other enzymes of the polyamine pathway, Int. J. Biochem and Cell Biol. 1999. vol. 31, pp. 107-122.

Soussi et al., Nucleotide sequence of a cDNA encoding the chicken p53 nuclear protein, Nucleic Acid Research, 1998, vol. 16, No. 23, p. 1183.

T. Gura, Systems for Identifying New Drugs Are Often Faulty. Science, Nov. 7, 1997, vol. 278, pp. 1041-1042.

T.C. Hsu, Karyology of Cells in Culture, Tissue Culture Methods and Applications, Kruse and Patterson Eds. 1973. Academic Press, NY, see abstract p. 764.

Tominaga et al., Detection of p73 antibodies in patients with various types of cancer: immunological characterization, Br. J. of Cancer, 2001, vol. 84, No. 1, pp. 57-63.

Wilson et al.. 2.2 Mb of continguous nucleotide sequence from chromosome III of C. elegans, Nature, vol. 368. pp. 32-38.

Zellner et al., Disparity in Expression of Protein Kinase C alpha in Human Glloma versus Glioma-derived Primary Cell Lines: Therapeutic Implications, Clin. Can. Res. 1998, vol. 4, pp. 1797-1802.

* cited by examiner

FIG. 1A

```
901  TCAGCACCATCCTGTACAACTTCATGTGTAACAGCAGCTGTGTGGGCGC  950
     ||||||||  |||||| |||||||| ||||||||||||  |||  |||  |||
798  GTACCACCATCCACTACAACTACATCTGTAACAGTTCCTGCATGGGCGGC  837

951  ATGAACCGACGGCCCATCCTCATCATCATCACCCTGGAGACGCGGGATGG  1000
     ||||||||  |||||||||||||  ||  ||||  ||||||  ||
838  ATGAACCGGAGGCCCATCCTCACAATTATCACACTGGAAGACTCCAGTGG  887

1001 GCAGGTGCTGGGCCGCCGGTCCTTCGAGGGCCGCATCTGCGCCTGTCCTG  1050
     |  |  ||||| ||    |||  ||| |||| ||  |  |  ||||||||
888  TAATCTACTGGACGGAACAGCTTTGAGGTGCGAGTTTGTGCCTGTCCTG  937

1051 CCCGCGACCGAAAAGCCGATGAGGACCACTACCGGGAGCAGCAGGCCTTG  1100
     || |  ||||      |||  ||  ||   |||  ||  ||  ||  | |
938  GGAGAGACCGGCGCACAGAGGAAGAGAATTTCC.............G  971

1101 AATGAGAGCTCCGCCAAGAACGGGGCTGCCAGCAAGCGCGCCTTCAAGCA  1150
     |  ||  ||    |||  |  |  |  ||||||| | |  ||  ||||| |
972  CAAGAAAGGGGAGCCTTGCCACGAGCTGCCCCCTGGAGCACTAAGCGAG  1021

1151 GAGTCCCCCTGCCGTCCCGCCCTGGGCCC  GGGTGTGAAGAAGCGGCGG  1199
       |  |  |  | ||  |  |||  |||  ||||||  |  |
1022 CACTGCCCAACAACACCAGCTCCTCTCCCCAGCCAAAGAAGAAACCACTG  1071

1200 CACGGAGACGAGGACACGTACTACCTGCAGGTGCGAGGCCGCGAGAACTT  1249
     |||| ||| |    |  |   |||  |  ||| |  ||  |  ||  |||
1072 GATGGAGAATATTTCAC......CCTTCAGATCCGCGGCGTGAGCGCTT  1115

1250 CGAGATCCTGATGAAGCTGAAGGAGAGCCTGGAGCTGATGGAGTTGGTGC  1299
     |||||| |  |  ||||||| |||  | ||| |||| |  ||  | ||
1116 CGAGATGTTCCGAGAGCTGAATGAGGCCTTGGAACTCAAGGA........  1157

1300 CGCAGCCGCTGGTAGACTCCTATCGGCAGCAGCAGCAGCTCCTACAGAGG  1349
       ||   ||||||| | |  |  |||  ||||| | | ||||  |||
1158 TGCCCAGGCTGGGAAAGAGCCAGCGG..GGAGCAGGGCTCACTCCAGCCA  1205

1350 CCGAGTCACCTACAGCCCCCATCCTACGGGCCCGTCCTCTCGCCCATGAA  1399
     || |  || |  ||| ||   | |  |  ||  ||  ||| ||  |||
1206 CCTGAAGTCCAAGAAGGGGCAATCTACCTCCCGCCATAAAAATTCATGT  1255

1400 CAAGGTGCACGGGGCCGTCAACAAGCTCCCCTCCGTCAACCAGCTGGTGG  1449
     | ||  | ||      |    ||||| | |  |  ||||||| ||  |||
1256 TCAAGACAGAGGGGCCTGACTCAGACTGACATTC.....TCAGCTTCTTG  1300

1450 GCCAGCCTCCCCCGCACAGCTCGGCAGCTACACCCAACCTGGACCTCTG  1499
     |||||| |    || |||||||  |  |    |  |  |||  |||||
1301 TTCCCCACTGAGCCTCCCACCCCATCT CTCCCTCCCTGCCATTTTG  1349

1500 GGCTCTGGGATGCTCAACAACCACGGCCACGCAGTGCCAGCCAACAGCGA  1549
     |  |||||||| |||  |      |  ||||| | | ||||| ||||  |
1350 AGTTCTGGGTCTTTAAACCCTTGCTTGCAATAGGTGTGTCAGAAGCAA  1399

1550 GATGACCAGCAGCCACGGCACCCAGTCCATGGTCTCGGGGTCCCACTGCA  1599
1400 A........................................  1400
```

FIG. 1B

```
  1 MAQSTTTSPDGGTTFEHLWSSLEPDSTYFDLPQSSRGNNEVVGGTDSSHD  50
    ..|:::...:|..:|....:.|:.||....:||...:......:|
  1 .....MEEPQSDPSTEPPLS....QETFSDLWKLLPENNVLSPLPSQAVD  41

51 VFHLEGHTTSVMAQFNLLSSTMDQMSSRAASASPYTPEHAASVPTHSPYA 100
    :|....|..:||.....|:......|...|..|||..|..:|:
 42 DLML...SPDDLAQWLTEDPGPDEAPRMSEAAPHMAPTPAAPTPA.APAP  87

101 QPSSTFDTMSPAPVIPSNTDYPGPHHFEVTFQQSSTAKSATWTYSPLLKK 150
    ||...:....:||...|.|..|...:|.:|:||||.|.||||.|.|
 88 APSWPL.....SSSVPSQKTYHGSYGFRLGFLHSGTAKSVTCTYSPDLNK 132

151 LYCQIAKTCPIQIKVSAPPPPGTAIRAMPVYKKAEHVTDIVKRCPNHELG 200
    :.||:||||:|:,|...||||.:|||:||..:|:|:|:|:|||:||
133 MFCQLAKTCPVQLWVDSTPPPGSRVRAMAIYKQSQHMTEVVRRCPHHE..  180

201 RDFNEGQSAPASHLIRVEGNNLSQYVDDFVTGRQSVVVPYEPPQVGTEFT 250
    |.:,:.||:.||||||||.:|.||.|.|.|:||||||||||:||,.|
181 RCSDSDGLAPPQHLIRVEGNLRVEYSDDRNTFRHSVVVPYEPPEVGSDCT 230

251 TILYNFMCNSSCVGGMNRRPILIIITLETRDGQVLGRRSFEGRICACPGR 300
    ||.||:|||||:|||||||||||||.|:|||:.|:||:|.|:|||||
231 TIHYNYMCNSSCMGGMNRRPILTIITLEDSSGNLLGRNSPEVRVCACPGR 280

301 DRKADEDHYREQQALNESSAKNGAASKRAFKQSPPAVPALGPGVKKRRHG 350
    ||:|:|::...:..:...|||...::.|..|::...:|:.
281 DRRTEEENFRKKG..EPCHELPPGSTKRALPNNTSSSPQ.....PKKKPL 323

351 DEDTYYLQVRGRENFEILMKLKESLELMELVPQPLVDSYRQQQQLLQRPS 400
    |::|.||:|||.||.||.:||..|..|....:|::..|...|...
374 DGEYFTLQIRGRERFEMFRELNEALELKDAQAGKEPAGSRAHSSHLKSKK 373

401 HLQPPSYGPVLSPMNKVHGGVNKLPSVHQLVGQPPHSSAATPNLGPVGS  450
    ......|:..|:|.
374 GQSTSRHKKFMFKTEGPDSD............................. 393
```

FIG. 2

```
  1 TGCCTCCCCGCCCGCGCACCCGCCCCGAGGCCTGTGCTCCTGCGAAGGGG  50
    ||||||||||||||||||||||||||||||||||||||||||||||||||
  1 TGCCTCCCCGCCCGCGCACCCGCCCCGAGGCCTGTGCTCCTGCGAAGGCG  50

51 ACGCAGCGAAGCCGGGGCCCGCGCCAGGCCGGCCGGGACGGACGCCGATG 100
    ||||||||||||||||||||||||||||||||||||||||||||||||||
 51 ACGCAGCGAAGCCGGGGCCCGCGCCAGGCCGGCCGGGACGGACGCCGATG 100

101 CCCGGAGCTGCGACGGCTGCAGAGCGAGCTGCCCTCGGAGGCCGGTGTGA 150
    ||||||||||||||||||||||||||||||||||||||||||||||||||
101 CCCGGAGCTGCGACGGCTGCAGAGCGAGCTGCCCTCGGAGGCCGGTGTGA 150

151 GGAAGATGGCCCAGTCCACCACCACCTCCCCCGATGGGGGCACCACGTTT 200
    ||||||||||||||||||||||||||||||||||||||||||||||||||
151 GGAAGATGGCCCAGTCCACCACCACCTCCCCCGATGGGGGCACCACGTTT 200

201 CAGCACCTCTGGAGCTCTCTGGAACCAGACAGCACCTACTTCGACCTTCC 250
    ||||||||||||||||||||||||||||||||||||||||||||||||||
201 CAGCACCTCTGGAGCTCTCTGGAACCAGACAGCACCTACTTCGACCTTCC 250

251 CCAGTCAAGCCGGGGGAATAATGAGGTGGTGGGTGGCACGGATTCCAGCA 300
    ||||||||||||||||||||||||||||||||||||||||||||||||||
251 CCAGTCAAGCCGGGCGAATAATGAGGTGGTGGGTGGCACGGATTCCAGCA 300

301 TGGACGTCTTCCACCTAGAGGGCATGACCACATCTGTCATGGCCCAGTTC 350
    ||||||||||||||||||||||||||||||||||||||||||||||||||
301 TGGACGTCTTCCACCTAGAGGGCATGACCACATCTGTCATGGCCCAGTTC 350

351 AATTTGCTGAGCAGCACCATGGACCAGATGAGCAGCCGCCTGCCTCGGC  400
    ||||||||||||||||||||||||||||||||||||||||||||||||||
351 AATTTGCTGAGCAGCACCATGGACCAGATGAGCAGCCGCCGCTGCCTCGGC 400

401 CAGCCCGTACACCCCGGAGCACGCCGCCAGCGTGCCCACCCATTCACCCT 450
    ||||||||||||||||||||||||||||||||||||||||||||||||||
401 CAGCCCGTACACCCCGGAGCACGCCGCCAGCGTGCCCACCCATTCACCCT 450

451 ACGCACAGCCCAGCTCCACCTTCGACACCATGTCGCCCGCGCCTGTCATC 500
    ||||||||||||||||||||||||||||||||||||||||||||||||||
451 ACGCACAGCCCAGCTCCACCTTCGACACCATGTCGCCCGCGCCTGTCATC 500

501 CCCTCCAACACCGACTATCCCGGACCCCACCACTTCGAGGTCACTTTCCA 550
    ||||||||||||||||||||||||||||||||||||||||||||||||||
501 CCCTCCAACACCGACTATCCCGGACCCCACCACTTCGAGGTCACTTTCCA 550

551 GCAGTCCAGCACGGCCAAGTCAGCCACCTGGACGTACTCCCCACTCTTGA 600
    ||||||||||||||||||||||||||||||||||||||||||||||||||
551 GCAGTCCAGCACGGCCAAGTCAGCCACCTGGACGTACTCCCCACTCTTGA 600

601 AGAAACTCTACTGCCAGATCGCCAAGACATGCCCCATCCAGATCAAGGTG 650
    ||||||||||||||||||||||||||||||||||||||||||||||||||
601 AGAAACTCTACTGCCAGATCGCCAAGACATGCCCCATCCAGATCAAGGTG 650

651 TCCGCCCCACCGCCCCCGGGCACGGCCATCCGGGCCATGCCTGTCTACAA 700
    ||||||||||||||||||||||||||||||||||||||||||||||||||
651 TCCGCCCCACCGCCCCCGGGCACGGCCATCCGGGCCATGCCTGTCTACAA 700

701 GAAGGCCGAGCACGTGACCGACATCGTGAAGCGCTGCCCCAACCACGAGC 750
    ||||||||||||||||||||||||||||||||||||||||||||||||||
701 GAAGGCCGAGCACGTGACCGACATCGTGAAGCGCTGCCCCAACCACGAGC 750

751 TCGGGAGGGACTTCAACGAAGGACAGTCTGCCCCAGCCAGCCACCTCATC 800
    ||||||||||||||||||||||||||||||||||||||||||||||||||
751 TCGGGAGGGACTTCAACGAAGGACAGTCTGCCCCAGCCAGCCACCTCATC 800

801 CGTGTGGAAGGCAATAATCTCTCGCAGTATGTGGACGACCCTGTCACCGG 850
    ||||||||||||||||||||||||||||||||||||||||||||||||||
801 CGTGTGGAAGGCAATAATCTCTCGCAGTATGTGGACGACCCTGTCACCGG 850

851 CAGGCAGAGCGTCGTGGTGCCCTATGAGCCACCACAGGTGGGGACAGAAT 900
    ||||||||||||||||||||||||||||||||||||||||||||||||||
851 CAGGCAGAGCGTCGTGGTGCCCTATGAGCCACCACAGGTGGGGACAGAAT 900
```

FIG. 3A

```
901  TCACCACCATCCTGTACAACTTCATGTGTAACAGCAGCTGTGTGGGGGC  950
     ||||||||||||||||||||||||||||||||||||||||||||||||
901  TCACCACCATCCTGTACAACTTCATGTGTAACAGCAGCTGTGTGGGGGC  950

951  ATGAACCGACGGCCCATCCTCATCATCATCACCCTGGAGACGCGGATGG 1000
     ||||||||||||||||||||||||||||||||||||||||||||||||
951  ATGAACCGACGGCCCATCCTCATCATCATCACCCTGGAGACGCGGATGG 1000

1001 GCAGGTGCTGGGCCGCCGGTCCTTCGAGGGCCGCATCTGCGCCTGTCCTG 1050
     ||||||||||||||||||||||||||||||||||||||||||||||||
1001 GCAGGTGCTGGGCCGCCGGTCCTTCGAGGGCCGCATCTGCGCCTGTCCTG 1050

1051 GCCGCGACCGAAAAGCCGATGAGGACCACTACCGGGAGCAGCAGGCCTTG 1100
     ||||||||||||||||||||||||||||||||||||||||||||||||
1051 GCCGCGACCGAAAAGCCGATGAGGACCACTACCGGGAGCAGCAGGCCTTG 1100

1101 AATGAGAGCTCCGCCAAGAACGGGGCTGCCAGCAAGCCCGCCTTCAAGCA 1150
     ||||||||||||||||||||||||||||||||||||||||||||||||
1101 AATGAGAGCTCCGCCAAGAACGGGGCTGCCAGCAAGCCCGCCTTCAAGCA 1150

1151 GAGTCCCCCTGCCGTCCCCGCCCTGGGCCCGGGTGTGAAGAAGCCGGCGG 1200
     ||||||||||||||||||||||||||||||||||||||||||||||||
1151 GAGTCCCCCTGCCGTCCCCGCCCTGGGCCCGGGTGTGAAGAAGCCGGCGG 1200

1201 ACGGAGACGAGGACACGTACTACCTGCAGGTGCCGAGGCCGCGAGAACTTC 1250
     ||||||||||||||||||||||||||||||||||||||||||||||||
1201 ACGGAGACGAGGACACGTACTACCTGCAGGTGCCGAGGCCGCGAGAACTTC 1250

1251 GAGATCCTGATGAAGCTGAACGAGAGCCTGGAGCTGATGGAGTTGGTGCC 1300
     ||||||||||||||||||||||||||||||||||||||||||||||||
1251 GAGATCCTGATGAAGCTGAACGAGAGCCTGGAGCTGATGGAGTTGGTGCC 1300

1301 GCAGCCGCTGGTAGACTCCTATCGGCAGCAGCAGCAGCTCCTACAGAGGC 1350
     ||||||||||||||||||||||||||||||||||||||||||||||||
1301 GCAGCCGCTGGTAGACTCCTATCGGCAGCAGCAGCAGCTCCTACAGAGGC 1350

1351 CGAGTCACCTACAGCCCCCATCCTACGGGCCGGTCCTCTCGCCCATGAAC 1400
     ||||||||||||||||||||||||||||||||||||||||||||||||
1351 CGAGTCACCTACAGCCCCCATCCTACGGGCCGGTCCTCTCGCCCATGAAC 1400

1401 AAGGTGCACGGGGGCGTGAACAAGCTGCCCTCGTCAACCAGCTGGTGGCG 1450
     ||||||||||||||||||||||||||||||||||||||||||||||||
1401 AAGGTGCACGGGGGCGTGAACAAGCTGCCCTCGTCAACCAGCTGGTGGCG 1450

1451 CCAGCCTCCCCCGCACAGCTCGGCAGCTACACCCAACCTGGGACCTGTCG 1500
     ||||||||||||||||||||||||||||||||||||||||||||||||
1451 CCAGCCTCCCCCGCACAGCTCGGCAGCTACACCCAACCTGGGACCTGTCG 1500

1501 GCTCTGGGATGCTCAACAACCACGGCCACGCAGTGCCAGCCAACAGCGAG 1550
     ||||||||||||||||||||||||||||||||||||||||||||||||
1501 GCTCTGGGATGCTCAACAACCACGGCCACGCAGTGCCAGCCAACAGCGAG 1550

1551 ATGACCAGCAGCCACGGCACCCAGTCCATGGTCTCGGGTCCCACTGCAC 1600
     ||||||||||||||||||||||||||||||||||||||||||||||||
1551 ATGACCAGCAGCCACGGCACCCAGTCCATGGTCTCGGGTCCCACTGCAC 1600

1601 TCCGCCACCCCCCTACCACGCCGACCCCAGCCTCGTCAGTTTTTTAACAG 1650
     ||||||||||||||||||||||||||||||||
1601 TCCGCCACCCCCCTACCACGCCGACCCCAGCCTCGTC............ 1637

1701 AGCATTTACCACCTGCAGAACCTGACCATCGAGGACCTGGGGGCCCTGAA 1750
                                    ||||||||||||||||||||
1638 ...........................AGGACCTGGGGGCCCTGAA 1656

1751 GATCCCCGAGCAGTATCGCATGACCATCTGGCGGGGCCTGCAGGACCTGA 1800
     ||||||||||||||||||||||||||||||||||||||||||||||||
```

FIG. 3B

```
1657 GATCCCCGAGCAGTATCGCATGACCATCTGGCGGGGCCTGCAGGACCTGA 1706

1801 AGCAGGGCCACGACTACGGCGCCGCCGCGCAGCAGCTGCTCCGCTCCAGC 1850
     ||||||||||||||||||||||||||||||||||||||||||||||||||
1707 AGCAGGGCCACGACTACGGCGCCGCCGCGCAGCAGCTGCTCCGCTCCAGC 1756

1851 AACGCCGCCGCCATTTCCATCGGCGGCTCCGGGGAGCTGCAGCGCCAGCG 1900
     ||||||||||||||||||||||||||||||||||||||||||||||||||
1757 AACGCCGCCGCCATTTCCATCGGCGGCTCCGGGGAGCTGCAGCGCCAGCG 1806

1901 GGTCATGGAGGCCGTGCACTTCCGCGTGCGCCACACCATCACCATCCCCA 1950
     ||||||||||||||||||||||||||||||||||||||||||||||||||
1807 GGTCATGGAGGCCGTGCACTTCCGCGTGCGCCACACCATCACCATCCCCA 1856

1951 ACCGCGGCGGCCCCGGCGCCGGCCCCGACGAGTGGGCGGACTTCGGCTTC 2000
     ||||||||||||||||||||||||||||||||||||||||||||||||||
1857 ACCGCGGCGGCCCCGGCGCCGGCCCCGACGAGTGGGCGGACTTCGGCTTC 1906

2001 GACCTGCCCGACTGCAAGGCCCGCAAGCAGCCCATCAAGGAGGAGTTCAC 2050
     ||||||||||||||||||||||||||||||||||||||||||||||||||
1907 GACCTGCCCGACTGCAAGGCCCGCAAGCAGCCCATCAAGGAGGAGTTCAC 1956

2051 GGAGGCCCAGATCCACTGAGGGGCCGGGCCCAGCCAGAGCCTGTGCCACC 2100
     ||||||||||||||||||||||||||||||||||||||||||||||||||
1957 GGAGGCCCAGATCCACTGAGGGGCCGGGCCCAGCCAGAGCCTGTGCCACC 2006

2101 GCCCAGAGACCCAGGCCGCCTCGCTCTC 2128
     ||||||||||||||||||||||||||||
2007 GCCCAGAGACCCAGGCCGCCTCGCTCTC 2034
```

FIG. 3C

```
    1 TGCCTCCCCGCCCGCGCACCCGCCCCGAGGCCCTGTGCTCCTGCGAAGGGGACGCAGCGAA    60
   61 GCCGGGGCCCCGCGCCAGGCCCGGCCGGGACGGACGCCGATGCCCGGAGCTGCCGACGGCTGC   120
  121 AGAGCCGACCTGCCCTCGGAGGCCCGTGTGAGGAAGATGGCCCAGTCCACCACCACCTCCC   180
  -10                                    M  A  Q  S  T  T  T  S  P   9
  181 CCGATGGGGGCACCACGTTTGAGCACCTCTGGAGCTCTCTGGAACCAGACAGCACCTACT   240
   10  D  G  T  T  F  E  H  L  W  S  S  L  E  P  D  S  T  Y  F     29
  241 TCGACCTTCCCCAGTCAAGCCGGGGGAATAATGAGGTGGTGGGTGGCACGGATTCCAGCA   300
   30  D  L  P  Q  S  S  R  G  N  N  E  V  V  G  G  T  D  S  S  N   49
  301 TGGACGTCTTCCACCTAGAGGGCATGACCACATCTGTCATGGCCCAGTTCAATTTGCTGA   360
   50  D  V  F  H  L  E  G  M  T  T  S  V  M  A  Q  F  N  L  L  S   69
  361 GCAGCACCATGGACCAGATGAGCAGCCGCGCTGCCTCGGCCAGCCCGTACACCCCGGAGC   420
   70  S  T  M  D  Q  M  S  S  R  A  A  S  A  S  P  Y  T  P  E  H   89
  421 ACGCCGCCAGCGTGCCCACCCATTCACCCTACGCACAGCCCAGCTCCACCTTCGACACCA   480
   90  A  A  S  V  P  T  H  S  P  Y  A  Q  P  S  S  T  F  D  T  N  109
  481 TGTCGCCCGCGCCTGTCATCCCCTCCAACACCGACTATCCGGACCCCACCACTTCGAGG   540
  110  S  P  A  P  V  I  P  S  N  T  D  Y  P  G  P  H  H  F  E  V  129
  541 TCACTTTCCAGCAGTCCAGCACGGCCAAGTCAGCCACCTGGACGTACTCCCCACTCTTGA   600
  130  T  F  Q  Q  S  S  T  A  K  S  A  T  W  T  Y  S  P  L  L  K  149
  601 AGAAACTCTACTGCCAGATCGCCAAGACATGCCCCATCCAGATCAAGGTGTCCGCCCCAC   660
  150  K  L  Y  C  Q  I  A  K  T  C  P  I  Q  I  K  V  S  A  P  P  169
  661 CGCCCCCCGGGCACCGCCATCCGGGCCATGCCTGTCTACAAGAAGGCGGAGCACGTGACCG   720
  170  P  G  T  A  I  R  A  M  P  V  Y  K  K  A  E  H  V  T  D    189
  721 ACATCGTGAAGCGCTGCCCCAACCACGAGCTCGGGAGGGACTTCAACGAAGGACAGTCTG   780
  190  I  V  K  R  C  P  N  H  E  L  G  R  D  F  N  E  G  Q  S  A  209
  781 CCCCAGCCAGCCACCTCATCCGTGTGGAAGGCAATAATCTCTCGCAGTATGTGGACGACC   840
  210  P  A  S  H  L  I  R  V  E  G  N  N  L  S  Q  Y  V  D  D  P  229
  841 CTGTCACCGGCAGGCAGAGCGTCGTGGTGCCCTATGAGCCACCACAGGTGGGGACAGAAT   900
  230  V  T  G  R  Q  S  V  V  V  P  Y  E  P  P  Q  V  G  T  E  F  249
  901 TCACCACCATCCTGTACAACTTCATGTGTAACAGCAGCTGTGTGGGGGGCATGAACCGAC   960
  250  T  T  I  L  Y  N  F  M  C  N  S  S  C  V  G  G  M  N  R  R  269
  961 GGCCCATCCTCATCATCATCACCCTGGAGACGCGGGATGGGCAGGTGCTGGGCCGCCGT  1020
  270  P  I  L  I  I  I  T  L  E  T  R  D  G  Q  V  L  G  R  R  S  289
 1021 CCTTCGAGGGCCGCATCTGCGCCTGTCCTGGCCGCGACCGAAAAGCCGATGAGGACCACT  1080
  290  F  E  G  R  I  C  A  C  P  G  R  D  R  K  A  D  E  D  H  Y  309
 1081 ACCGCGAGCAGCAGGCCCTTGAATGAGAGCTCCGCCAAGAACGGGGCTGCCAGCAAGCGCG  1140
  310  R  E  Q  Q  A  L  N  E  S  S  A  K  N  G  A  A  S  K  R  A  329
 1141 CCTTCAAGCAGAGTCCCCCTGCCGTCCCCGCCCTGGGCCCGGGTGTGAAGAAGCGGCGCC  1200
  330  F  K  Q  S  P  P  A  V  P  A  L  G  P  G  V  K  K  R  R  H  349
 1201 ACGGAGACGAGGACACGTACTACCTGCAGGTGCGAGGCCGCGAGAACTTCGAGATCCTGA  1260
  350  G  D  E  D  T  Y  Y  L  Q  V  R  G  R  E  H  F  E  I  L  M  369
 1261 TGAAGCTGAAGGAGAGCCTGGAGCTGATGGAGCTTGTGCCCCAGCCGCTGGTAGACTCCT  1320
  370  K  L  K  E  S  L  E  L  M  E  L  V  P  Q  P  L  V  D  S  Y  389
 1321 ATCGCCAGCAGCAGCAGCTCCTACAGAGGCCGAGTCACCTACAGCCCCCATCCTACGGC  1380
  390  R  Q  Q  Q  Q  L  L  Q  R  P  S  H  L  Q  P  P  S  Y  G  P  409
 1381 CGGTCCTCTCGCCCATGAACAAGGTGCACGGGGGCGTGAACAAGCTGCCCTCCGTCAACC  1440
  410  V  L  S  P  M  N  K  V  H  G  G  V  N  K  L  P  S  V  N  Q  429
 1441 AGCTGGTGGGCCAGCCTCCCCCGCACAGCTCGGCTGCTACACCCAACCTGGGACCTGTGG  1500
  430  L  V  G  Q  P  P  P  H  S  S  A  A  T  P  N  L  G  P  V  G  449
 1501 GCTCTGGGATGCTCAACAACCACGGCCACGCAGTGCCAGCCAACAGCGAGATGACCAGCA  1560
  450  S  G  M  L  N  N  H  G  H  A  V  P  A  N  S  E  M  T  S  S  469
 1561 GCCACTGCACCCAGTCCATGGTCTCCGGGTCCCACTGCACTCCGCCACCCCCTTACCACG  1620
  470  H  G  T  Q  S  M  V  S  G  S  H  C  T  P  P  P  P  Y  H  A  489
 1621 CCGACCCCAGCCTCGTCAGTTTTTTAACAGGATTGGGGTGTCCAAACTGCATCGAGTATT  1680
  490  D  P  S  L  V  S  F  L  T  G  L  G  C  P  N  C  I  E  Y  F  509
```

FIG. 4A

```
1681  TCACGTCCCAGGGGTTACAGAGCATTTACCACCTGCAGAACCTGACCATCGAGGACCTGG  1740
 510   T  S  Q  G  L  Q  S  I  Y  H  L  Q  N  L  T  I  E  D  L  G   529
1741  GGGCCCTGAAGATCCCCGAGCAGTATCGCATGACCATCTGGCGCGGCCTGCAGGACCTGA  1800
 530   A  L  K  I  P  E  Q  Y  R  M  T  I  W  R  G  L  Q  D  L  K   549
1801  AGCAGGGCCACGACTACGGCGCCGCCGCCCAGCAGCTGCTCCGCTCCAGCAACGCGGCCG  1860
 550   Q  G  H  D  Y  G  A  A  A  Q  Q  L  L  R  S  S  N  A  A  A   569
1861  CCATTTCCATCGGCGGCTCCGGGGAGCTGCAGCGCCAGCGGGTCATGCAGGCCGTGCACT  1920
 570   I  S  I  G  G  S  G  E  L  Q  R  Q  R  V  M  Q  A  V  H  F   589
1921  TCCGCGTGCGCCACACCATCACCATCCCCAACCGCGGCGGCCCCGGCGCCGGCCCCGACG  1980
 590   R  V  R  H  T  I  T  I  P  N  R  G  G  P  G  A  G  P  D  E   609
1981  AGTGGGCGGACTTCGGCTTCGACCTGCCCGACTGCAAGGCCCGCAAGCAGCCCATCAAGG  2040
 610   W  A  D  F  G  F  D  L  P  D  C  K  A  R  K  Q  P  I  K  E   629
2041  AGGAGTTCACGGAGGCCGAGATCCACTGAGTGGCCGGGCCCAGCCAGAGCCTGTGCCACC  2100
 630   E  F  T  E  A  E  I  H  *                                    649
2101  GCCCAGAGACCCAGGCCGCCTCGCTCTCCTTCCTGTGTCCAAAACTGCCTCCGGAGGCAG  2160
2161  GGCCTCCAGGCTGTGCCCGGGGAAAGGCAAGGTCCGGCCCATGCCCCGGCCACCTCACCGG  2220
2221  CCCCAGGAGAGGCCCAGCCACCAAAGCCGCCTGCCGGACAGCCTGAGTCACCTGCAGAACC  2280
2281  TTCTGGAGCTGCCCTAATGCTGGGCTTGCGGGGCAGGGGCCGGCCCACTCTCAGCCCTGC  2340
2341  CACTGCCGGGCCGTGCTCCATGGCAGGCGTGGGTGGGGACCGCAGTGTCAGCTCCGACCTC  2400
2401  CAGGCCTCATCCTAGAGACTCTGTCATCTGCCGATCAAGCAAGGTCCTTCCAGAGGAAAG  2460
2461  AATCCTCTTCGCTGGTGGACTGCCAAAAAGTATTTTGCGACATCTTTTGGTTCTGGAGAG  2520
2521  TGGTGAGCAGCCAAGCGACTGTGTCTGAAACACCGTGCATTTTCAGGGAATGTCCCTAAC  2580
2581  GGGCTGGGGACTCTCTCTGCTGGACTTGGGAGTGGCCTTTGCCCCCAGCACACTGTATTC  2640
2641  TGCGGGACCGCCTCCTTCCTGCCCTAACAACCACCAAAGTGTTGCTGAAATTGGAGAAA  2700
2701  ACTGGGGAAGGCGCAACCCCTCCCAGGTGCGGGAAGCATCTGGTACCGCCTCGGCCAGTG  2760
2761  CCCCTCAGCCTGGCCACAGTCACCTCTCCTTGGGGAAACCCTGGGCAGAAAGGGACACCCT  2820
2821  GTCCTTAGAGGACCGGAAATTGTCAATATTTGATAAAATGATACCCTTTTCTAC       2874
```

```
  1 GCGAGCTGCCCTCGGAGGCCGGCCGTGGGGAAGATGGCCCAGTCCACCGCCACCTCCCCTG   60
 -9                                    M  A  Q  S  T  A  T  S  P  D  10
 61 ATGGGGGCACCACGTTTGAGCACCTCTGGAGCTCTCTGGAACCAGACAGCACCTACTTCG  120
 11  G  G  T  T  F  E  H  L  W  S  S  L  E  P  D  S  T  Y  F  D   30
121 ACCTTCCCCAGTCAAGCCGGGGGAATAATGAGGTGGTGGGCGGAACGGATTCCAGCATGG  180
 31  L  P  Q  S  S  R  G  N  N  E  V  V  G  G  T  D  S  S  M  D   50
181 ACGTCTTCCACCTGGAGGGCATGACTACATCTGTCATGGCCCAGTTCAATCTGCTGAGCA  240
 51  V  F  H  L  E  G  M  T  T  S  V  M  A  Q  F  N  L  L  S      70
241 GCACCATGGACCAGATGAGCAGCCGCGCGGCCTCGGCCAGCCCCTACACCCCAGAGCACG  300
 71  S  T  M  D  Q  M  S  S  R  A  A  S  A  S  P  Y  T  P  E  H   90
301 CCGCCAGCGTGCCCACCCACTCGCCCTACGCACAACCCAGCTCCACCTTCGACACCATGT  360
 91  A  A  S  V  P  T  H  S  P  Y  A  Q  P  S  S  T  F  D  T  M  110
361 CGCCCGGCGCCTGTCATCCCCTCCAACACCGACTACCCCGGACCCCACCACTTTGAGGTCA  420
111  S  P  A  P  V  I  P  S  N  T  D  Y  P  G  P  H  H  F  E  V  130
421 CTTTCCAGCAGTCCAGCACGGCCAAGTCAGCCACCTGGACGTACTCCCCGCTCTTGAAGA  480
131  T  F  Q  Q  S  S  T  A  K  S  A  T  W  T  Y  S  P  L  L  K  150
481 AACTCTACTGCCAGATCGCCAAGACATGCCCCATCCAGATCAAGGTGTCCACCCCGCCAC  540
151  K  L  Y  C  Q  I  A  K  T  C  P  I  Q  I  K  V  S  T  P  P  170
541 CCCCAGGCACTGCCATCCGGGCCATGCCTGTTTACAAGAAAGCGGAGCACGTGACCGACG  600
171  P  P  G  T  A  I  R  A  M  P  V  Y  K  K  A  E  H  V  T  D  190
601 TCGTGAAACGCTGCCCCAACCACGAGCTCGGGAGGGACTTCAACGAAGGACAGTCTGCTC  660
191  V  V  K  R  C  P  N  H  E  L  G  R  D  F  N  E  G  Q  S  A  210
661 CAGCCAGCCACCTCATCCGCGTGGAAGGCAATAATCTCTCGCAGTATGTGGATGACCCTG  720
211  P  A  S  H  L  I  R  V  E  G  N  N  L  S  Q  Y  V  D  D  P  230
721 TCACCGGCAGGCAGAGCGTCGTGGTGCCCTATGAGCCACCACAGGTGGGGACGGAATTCA  780
231  V  T  G  R  Q  S  V  V  V  P  Y  E  P  P  Q  V  G  T  E  F  250
781 CCACCATCCTGTACAACTTCATGTGTAACAGCAGCTGTGTAGGGGGCATGAACCGGCGGC  840
251  T  T  I  L  Y  N  F  M  C  N  S  S  C  V  G  G  M  N  R  R  270
841 CCATCCTCATCATCATCACCCTGGAGATGCGGGATGGGCAGGTGCTGGGCCGCCGGTCCT  900
271  P  I  L  I  I  I  T  L  E  M  R  D  G  Q  V  L  G  R  R  S  290
901 TTGAGGGCCGCATCTGCGCCTGTCCTGGCCGCGACCGAAAAGCTGATGAGGACCACTACC  960
291  F  E  G  R  I  C  A  C  P  G  R  D  R  K  A  D  E  D  H  Y  310
961 GGGAGCAGCAGGCCCTGAACGAGAGCTCCGCCAAGAACGGGGCCGCCAGCAAGCGTGCCT 1020
311  R  E  Q  Q  A  L  N  E  S  S  A  K  N  G  A  A  S  K  R  A  330
1021 TCAAGCAGAGCCCCCCTGCCGTCCCCGCCCTTGGTGCCGGTGTGAAGAAGCGGCGGCATG 1080
331  F  K  Q  S  P  P  A  V  P  A  L  G  A  G  V  K  K  R  R  H  350
1081 GAGACGAGGACACGTACTACCTTCAGGTGCGAGGCCGGGAGAACTTTGAGATCCTGATGA 1140
351  G  D  E  D  T  Y  Y  L  Q  V  R  G  R  E  N  F  E  I  L  M  370
1141 AGCTGAAAGAGAGCCTGGAGCTGATGGAGTTGGTGCCGCAGCCACTGGTGGACTCCTATC 1200
371  K  L  K  E  S  L  E  L  M  E  L  V  P  Q  P  L  V  D  S  Y  390
1201 GGCAGCAGCAGCAGCTCCTACAGAGGCCGAGTCACCTACAGCCCCCGTCCTACGGGCCGG 1260
391  R  Q  Q  Q  Q  L  L  Q  R  P  S  H  L  Q  P  P  S  Y  G  P  410
1261 TCCTCTCGCCCATGAACAAGGTGCACGGGGGCATGAACAAGCTGCCCTCCGTCAACCAGC 1320
411  V  L  S  P  M  N  K  V  H  G  G  M  N  K  L  P  S  V  N  Q  430
1321 TGGTGGGCCAGCCTCCCCCGCACAGTTCGGCAGCTACACCCAACCTGGGGCCCGTGGGCC 1380
431  L  V  G  Q  P  P  P  H  S  S  A  A  T  P  N  L  G  P  V  G  450
1381 CCGGGATGCTCAACAACCATGGCCACGCAGTGCCAGCCAACGGCGAGATGAGCAGCAGCC 1440
451  P  G  M  L  N  N  H  G  H  A  V  P  A  N  G  E  M  S  S  S  470
```

FIG. 6A

```
1441  ACAGCGCCCAGTCCATGGTCTCGGGGTCCCACTGCACTCCGCCACCCCCTACCACGCCG  1500
 471    S  A  Q  S  M  V  S  G  H  C  T  P  P  P  P  Y  H  A  D    490
1501  ACCCCAGCCTCGTCAGTTTTTTAACAGGATTGGGGTGTCCAAACTGCATCGAGTATTTCA  1560
 491    P  S  L  V  S  F  L  T  G  L  G  C  P  N  C  I  E  Y  F  T  510
1561  CCTCCCAAGGGTTACAGAGCATTTACCACCTGCAGAACCTGACCATTGAGGACCTGGGGG  1620
 511    S  Q  G  L  Q  S  I  Y  H  L  Q  N  L  T  I  E  D  L  G  A  530
1621  CCCTGAAGATCCCCGAGCAGTACCGCATGACCATCTGGCGGGGCCTGCAGGACCTGAAGC  1680
 531    L  K  I  P  E  Q  Y  R  M  T  I  W  R  G  L  Q  D  L  K  Q  550
1681  AGGGCCACGACTACAGCACCGCGCAGCAGCTGCTCCGCTCTAGCAACGCGGCCACCATCT  1740
 551    G  H  D  Y  S  T  A  Q  Q  L  L  R  S  S  N  A  A  T  I  S  570
1741  CCATCGGCGGCTCAGGGGAACTGCAGCGCCAGCGGGTCATGGAGGCCGTGCACTTCCGCG  1800
 571    I  G  G  S  G  E  L  Q  R  Q  R  V  M  E  A  V  H  F  R  V  590
1801  TGCGCCACACCATCACCATCCCCAACCGCGGCGGCCCAGGCGGCGGCCCTGACGAGTGGG  1860
 591    R  H  T  I  T  I  P  N  R  G  G  P  G  G  P  D  E  W  A    610
1861  CGGACTTCGGCTTCGACCTGCCCGACTGCAAGGCCCGCAAGCAGCCCATCAAGGAGGAGT  1920
 611    D  F  G  F  D  L  P  D  C  K  A  R  K  Q  P  I  K  E  E  F  630
1921  TCACGGAGGCCGAGATCCACTGAGGGCCTCGCCTGGCTGCAGCCTGCGCCACCGCCCAGA  1980
 631    T  E  A  E  I  H  *                                          650
1981  GACCCAAGCTGCCTCCCCTCTCCTTCCTGTGTGTCCAAAACTGCCTCAGGAGGCAGGACC  2040
2041  TTCGGGCTGTGCCCGGGGAAAGGCAAGGTCCGGCCCATCCCCAGGCACCTCACAGGCCCC  2100
2101  AGGAAAGGCCCCAGCCACCGAAGCCGCCTGTGGACAGCCTGAGTCACCTGCAGAACC     2156
```

```
  1  TGGTCCCGCTTCGACCAAGACTCCGGCTACCAGCTTGCGGGCCCCGCGGAGGAGGAGACC   60
 61  CCGCTGGGGCTAGCTGGGCGACGCGCGCCAAGCGGCGGCGGGAAGGAGGCGGGAGGAGCG  120
121  GGGCCCGAGACCCCGACTCGGGCAGAGCCAGCTGGGGAGGCGGGGCGCGCGTGGGAGCCA  180
181  GCGGCCCGGGTGGCCGGCCCTCCTCCGCCACGGCTGAGTGCCCGCGCTGCCTTCCCGCCG  240
241  GTCCGCCAAGAAAGGCGCTAAGCCTGCGGCAGTCCCCTCGCCGCCGCCTCCCTGCTCCGC  300
301  ACCCTTATAACCCGCCGTCCCGCATCCAGGCGAGGAGGCAACGCTGCAGCCCAGCCCTCG  360
361  CCGACGCCGACGCCCGGCCCGGAGCAGAATGAGCGGCAGCGTTGGGGAGATGGCCCAGAC  420
 -8                                   M  S  G  S  V  G  E  M  A  Q  T   11
421  CTCTTCTTCCTCCTCCTCCACCTTCGAGCACCTGTGGAGTTCTCTAGAGCCAGACAGCAC  480
 12   S  S  S  S  S  T  F  E  H  L  W  S  S  L  E  P  D  S  T   31
481  CTACTTTGACCTCCCCCAGCCCAGCCAAGGGACTAGCGAGGCATCAGGCAGCGAGGAGTC  540
 32   Y  F  D  L  P  Q  P  S  Q  G  T  S  E  A  S  G  S  E  E  S   51
541  CAACATGGATGTCTTCCACCTGCAAGGCATGGCCCAGTTCAATTTGCTCAGCAGTGCCAT  600
 52   N  M  D  V  F  H  L  Q  G  M  A  Q  F  N  L  L  S  S  A  M   71
601  GGACCAGATGGGCAGCCGTGCGGCCCCGGCGAGCCCCTACACCCCGGAGCACGCCGCCAG  660
 72   D  Q  M  G  S  R  A  A  P  A  S  P  Y  T  P  E  H  A  A  S   91
661  CGCGCCCACCCACTCGCCCTACGCGCAGCCCAGCTCCACCTTCGACACCATGTCTCCGGC  720
 92   A  P  T  H  S  P  Y  A  Q  P  S  S  T  F  D  T  M  S  P  A  111
721  GCCTGTCATCCCTTCCAATACCGACTACCCCGGCCCCC                      758
112   P  V  I  P  S  N  T  D  Y  P  G  P                       123
```

FIG. 8

```
Name: sr-p70a-cos3    Len:  650   Check: 9661   Weight: 1.00
Name: sr-p70b-cos3    Len:  650   Check: 3605   Weight: 1.00
Name: sr-p70-ht29     Len:  650   Check:   85   Weight: 1.00
Name: sr-p70c-att20   Len:  650   Check: 4072   Weight: 1.00
Name: sr-p70a-att20   Len:  650   Check: 4204   Weight: 1.00

//

1                                                         50
sr-p70a-cos3   .......MAQ STTTSPDGGT TFEHLWSSLE PDSTYFDLPQ SSRGNNEVVG
sr-p70b-cos3   .......MAQ STTTSPDGGT TFEHLWSSLE PDSTYFDLPQ SSRGNNEVVG
sr-p70-ht29    .......MAQ STATSPDGGT TFEHLWSSLE PDSTYFDLPQ SSRGNNEVVG
sr-p70c-att20  .......... .......... .......... .......... ..........
sr-p70a-att20  MSGSVGEMAQ ...TSSSSSS TFEHLWSSLE PDSTYFDLPQ PSQGTSEASG 51                                                       100
sr-p70a-cos3   GTDSSMD.VF HLEGMTTSVM AQFNLLSSTM DQMSSRAASA SPYTPEHAAS
sr-p70b-cos3   GTDSSMD.VF HLEGMTTSVM AQFNLLSSTM DQMSSRAASA SPYTPEHAAS
sr-p70-ht29    GTDSSMD.VF HLEGMTTSVM AQFNLLSSTM DQMSSRAASA SPYTPEHAAS
sr-p70c-att20  ...MCMGPVY ..ESLG...Q AQFNLLSSAM DQMGSRAAPA SPYTPEHAAS
sr-p70a-att20  SEESNMD.VP HLQGM..... AQFNLLSSAM DQMGSRAAPA SPYTPEHAAS 101                                                      150
sr-p70a-cos3   VPTHSPYAQP SSTFDTMSPA PVIPSNTDYP GPHHFEVTFQ QSSTAKSATW
sr-p70b-cos3   VPTHSPYAQP SSTFDTMSPA PVIPSNTDYP GPHHFEVTFQ QSSTAKSATW
sr-p70-ht29    VPTHSPYAQP SSTFDTMSPA PVIPSNTDYP GPHHFEVTFQ QSSTAKSATW
sr-p70c-att20  APTHSPYAQP SSTFDTMSPA PVIPSNTDYP GPHHFEVTFQ QSSTAKSATW
sr-p70a-att20  APTHSPYAQP SSTFDTMSPA PVIPSNTDYP GP........ ..........

151                                                      200
sr-p70a-cos3   TYSPLLKKLY CQIAKTCPIQ IKVSAPPPPG TAIRAMPVYK KAEHVTDIVK
sr-p70b-cos3   TYSPLLKKLY CQIAKTCPIQ IKVSAPPPPG TAIRAMPVYK KAEHVTDIVK
sr-p70-ht29    TYSPLLKKLY CQIAKTCPIQ IKVSTPPPPG TAIRAMPVYK KAEHVTDIVK
sr-p70c-att20  TYSPLLKKLY CQIAKTCPIQ IKVSTPPPPG TAIRAMPVYK KAEHVTDIVK
sr-p70a-att20  .......... .......... .......... .......... ..........

201                                                      250
sr-p70a-cos3   RCPNHELGRD FNEGQSAPAS HLIRVEGNNL SQYVDDPVTG RQSVVVPYEP
sr-p70b-cos3   RCPNHELGRD FNEGQSAPAS HLIRVEGNNL SQYVDDPVTG RQSVVVPYEP
sr-p70-ht29    RCPNHELGRD FNEGQSAPAS HLIRVEGNNL SQYVDDPVTG RQSVVVPYEP
sr-p70c-att20  RCPNHELGRD FNEGQSAPAS HLIRVEGNNL AQYVDDPVTG RQSVVVPYEP
sr-p70a-att20  .......... .......... .......... .......... ..........

251                                                      300
sr-p70a-cos3   PQVGTEFTTI LYNFMCNSSC VGGMNRRPIL IIITLETRDG QVLGRRSFEG
sr-p70b-cos3   PQVGTEFTTI LYNFMCNSSC VGGMNRRPIL IIITLETRDG QVLGRRSFEG
sr-p70-ht29    PQVGTEFTTI LYNFMCNSSC VGGMNRRPIL IIITLEMRDG QVLGRRSFEG
sr-p70c-att20  PQVGTEFTTI LYNFMCNSSC VGGMNRRPIL VIITLETRDG QVLGRRSFEG
sr-p70a-att20  .......... .......... .......... .......... ..........

301                                                      350
sr-p70a-cos3   RICACPGRDR KADEDHYREQ QALNESSAKN GAASKRAFKQ SPPAVPALGP
sr-p70b-cos3   RICACPGRDR KADEDHYREQ QALNESSAKN GAASKRAFKQ SPPAVPALGP
sr-p70-ht29    RICACPGRDR KADEDHYREQ QALNESSAKN GAASKRAFKQ SPPAVPALGA
sr-p70c-att20  RICACPGRDR KADEDHYREQ QALNESTTKN GAASKRAFKQ SPPAIPALGT
sr-p70a-att20  .......... .......... .......... .......... ..........
```

FIG. 9A

```
                    351                                                          400
 _ sr-p70a-cos3     GVKKRRHGDE  DTYYLQVRGR  ENFEILMKLK  ESLELMELVP  QPLVDSYR..
 _ sr-p70b-cos3     GVKKRRHGDE  DTYYLQVRGR  ENFEILMKLK  ESLELMELVP  QPLVDSYR..
   sr-p70-ht29     GVKKRRHGDE  DTYYLQVRGR  ENFEILMKLK  ESLELMELVP  QPLVDSYR..
_sr-p70c-att20     NVKKRRHGDE  DMFYMHVRGR  ENFEILMKVK  ESLELMELVP  QPLVDSYRQQ
_sr-p70a-att20     ..........  ..........  ..........  ..........  ..........

401                                                          450
 _ sr-p70a-cos3     QQQQLLQRPS  HLQPPSYGPV  LSPMNKVHGG  VNKLPSVNQL  VGQPPPHSSA
 _ sr-p70b-cos3     QQQQLLQRPS  HLQPPSYGPV  LSPMNKVHGG  VNKLPSVNQL  VGQPPPHSSA
   sr-p70-ht29     QQQQLLQRPS  HLQPPSYGPV  LSPMNKVHGG  MNKLPSVNQL  VGQPPPHSSA
_sr-p70c-att20     QQQQLLQRPS  HLQPPSYGPV  LSPMNKVHGG  VNKLPSVNQL  VGQPPPHSSA
_sr-p70a-att20     ..........  ..........  ..........  ..........  ..........

451                                                          500
 _ sr-p70a-cos3     ATPNLGPVGS  GMLNNHGHAV  PANSEMTSSH  GTQSMVSGSH  CTPPPPYHAD
 _ sr-p70b-cos3     ATPNLGPVGS  GMLNNHGHAV  PANSEMTSSH  GTQSMVSGSH  CTPPPPYHAD
   sr-p70-ht29     ATPNLGPVGP  GMLNNHGHAV  PANGEMSSSH  SAQSMVSGSH  CTPPPPYHAD
_sr-p70c-att20     AGPNLGPMGS  GMLNSHGHSM  PANGEMNGGH  SSQTMVSGSH  CTPPPPYHAD
_sr-p70a-att20     ..........  ..........  ..........  ..........  ..........

501                                                          550
 _ sr-p70a-cos3     PSLVSFLTGL  GCPNCIEYFT  SQGLQSIYHL  QNLTIEDLGA  LKIPEQYRMT
 _ sr-p70b-cos3     PSLVR..T.W  G.P.......  ..........  ..........  ..........
   sr-p70-ht29     PSLVSFLTGL  GCPNCIEYFT  SQGLQSIYHL  QNLTIEDLGA  LKIPEQYRMT
_sr-p70c-att20     PSLVSFLTGL  GCPNCIECFT  SQGLQSIYHL  QNLTIEDLGA  LKVPDQYRMT
_sr-p70a-att20     ..........  ..........  ..........  ..........  ..........

551                                                          600
 _ sr-p70a-cos3     IWRGLQDLKQ  GHDYGAAAQQ  LLR.SSNAAA  ISIGGSGELQ  RQRVMEAVHF
 _ sr-p70b-cos3     ..........  ..........  ..........  ..........  ..........
   sr-p70-ht29     IWRGLQDLKQ  GHDYS.TAQQ  LLR.SSNAAT  ISIGGSGELQ  RQRVMEAVHF
_sr-p70c-att20     IWRGLQDLKQ  SHDCG...QQ  LLRSSSNAAT  ISIGGSGELQ  RQRVMEAVHF
_sr-p70a-att20     ..........  ..........  ..........  ..........  ..........

601                                                          650
 _ sr-p70a-cos3     RVRHTITIPN  RGGPGA..GP  DEWADFGFDL  PDCKARKQPI  KEEFTEAEIH
 _ sr-p70b-cos3     ..........  ..........  ..........  ..........  ..........
   sr-p70-ht29     RVRHTITIPN  RGGPGG..GP  DEWADFGFDL  PDCKARKQPI  KEEFTEAEIH
_sr-p70c-att20     RVRHTITIPN  RGGAGAVTGP  DEWADFGFDL  PDCKSRKQPI  KEEFTETESH
_sr-p70a-att20     ..........  ..........  ..........  ..........  ..........
```

FIG. 9B

```
  1←─┬─→2                         ←──┬──→3
  1  MAQS..TATSPDGGTTFEHLWSSLEPDSTYFDLPQSSRGNNEVVGGTDSSMD   50
     ||      ||  |||   ||                  ||           ||
  1  MEEPQSDPSVEPPLSQETFSDLWKLLPE............NNVLSPLFSQAMD  41
  1←─┴─→2        ←──┬──→3                        ←──┬─→4
 51  VFHLEGMTTSVMAQFNLLSSTMDQMSSRAASASPYTPEHAASVPTHSPYA   100
      |   |        |    |        ||  ||   |     |     |
 42  DLML...SPDDIEQWFTEDGPDEAPRMPEAAPPVAPAPAAPTPA.APAP    87
                                                ←──┬──→5
101  QPSSTFDTMSPAPVIPSNTDYPGPHHFEVTFQQSSTAKSATWTYSPLLKK  150
      ||    ||    |   |    |   |       |||| | ||||||||
 88  APSWPL....SSSVPSQKTYQGSYGFRLGFLHSGTAKSVTCTYSPALNK   132
                                                ←──┴─→5
151  LYCQIAKTCPIQIKVSTPPPPGTAIRAMPVYKKAEHVTDVVKRCPNHELG   200
     | || |||||| |  ||||| ||  |||  |||   | ||| |||  |
133  MFCQLAKTCPVQLWVDSTPPPGTRVRAMAIYKQSQHMTEVVRRCPHHE..   180
          ←──┬──→6                          ←──┬──→7
201  RDFNEGQSAPASHLIRVEGNNLSQYVDDPVTGRQSVVVPYEPPQVGTEFT   250
      |       || ||||||||  |  ||   | ||||||||||  |  |
181  RCSDSDGLAPPQHLIRVEGNLRVEYLDDRNTFRHSVVVPYEPPEVGSDCT   230
          ←──┴──→6                     ←──┬──→7
251  TILYNFMCNSSCVGGMNRRPILIIITLEMRDGQVLGRRSFEGRICACPGR   300
     || || |||||| ||||||||| |||||  |  ||| ||| |||||||||
231  TIHYNYMCNSSCMGGMNRRPILTIITLEDSSGNLLGRNSFEVRVCACPGR   280
                                        ←──┬──→9
301  DRKADEDHYREQQALNESSAKNGAASKRAFKQSPPAVPALGAGVKKRRHG   350
     ||                |||  |         |||        |
281  DRRTEEENLRKKGEPHHELP..PGSTKRALPNNTSSPQ.....PKKPL    323
         ←──┬──→10                              ←──┬──→11
351  DEDTYYLQVRGRENFEILMKLKESLELMELVPQPLVDSYRQQQLLQRPS   400
      |   |||||| ||  |  |  |  |||
324  DGEYFTLQIRGRERPEMFRELNEALELKDAQAGKEPGGSRAHSSHLKSKK  373
         ←──┴──→10                              ←──┬─→11←─→12
401  HLQPPSYGPVLSPMNKVHGGMNKLPSVNQLVGQPPPHSSAATPNLGPVGP  450

374  GQSTSRHKKLMFKTEGPDSD                               393
                                                 ←──┬──→13
451  GMLNNMHGHAVPANGEMSSSHSAQSMVSGSHCTPPPPYHADPSLVSPLTGL 500

←─→14
501  GCPNCIEYFPTSQGLQSIYHLQNLTIEDLGALKIPEQYRMTIWRGLQDLKQ 550

551  GHDYSTAQQLLRSSNAATISIGGSGELQRQRVMEAVHFRVRHTITIPNRG  600

601  GPGGGPDEWADFGFDLPDCKARKQPIKEEFTEAEIH                636
```

```
                                                                                 INTRON1
  1        CACCCTACTCC AGGGATGGCC CAAGCAGGGC CACTTGCCTG CGGCCCCCAC
 51        CGAGCCTGTC ACAGACGAGAC AGAGCAGGAC AGAGAGGAG TTCCAGGGT GCTCAGGTGT
                                                                                 EXON2
101        CATTCCTTCC TTCCTGGCAG GCCAGCTGCC CTCGAGGCC GAGGTGGGGA
            A
151        AGATGGGCCA GTCCACCGGG ATCTCCCCTG ATGGGCGGC CACGTTTAG
201        CACCCTCTGA GCTCTCTG AGGGCCTTG CTGCTCAGA GTGGAGGGCC
251        CCCCTGGCAG GCACTCTGG CTAGCTCAG CCACCTTCG TGGCTAACT
301        GGGCCAGAGC AGGAGGGGTG GCCCGGGAG GACTCTGGGC TAGCCCCAGG
351        CACCCTCACT GAGACTTTGG GCTAAACTTG GCAACCCTCA CTGGGATTCT
401        GGGCTAGCCT CGACCACCCT ACTACTCTTG ACTGGACACTA AGCAGGAGAG
451        CTGGCTCCAC ACTACTCTTG GCCTAGCCTA AGCACCCTC ATCACCTGC
                                                                                 INTRON2
501        GGACAGGGCG CGTCGAGCAG GCAGGGAAGA GGGACTGCTG CCCTAGGCCT
551        TCCCTGGGGA TCCAGGACCA AAATTCAGAC AGAGCCCAGG TCTTTCTCT
601        GGAGAGGGCC CATGCCCAGG AGAGCCCCAG AGAGCCCCAG AATAACACAG CCCATGAGAG
651        GCTCTCTCTC TCTGGCACTC ACAGACCTCA TGGAATGGCA GGTGGAGGAC
701        AGAGATGGGA TGAGGGGAAA TGAGAGGGCT AGGAGAGGTA GGCCTCACCA
751        GGAGTCTTCAG GCTAGGCTTG AGCTCTGGGC AGGAGAGTA TTGGCTCAC
                                                                                 EXON3
801        ACCCAAAACTG GGGCCGGACG CTTCATTTT CCTTCCCAG CCCCAGGGAG
851        CCAGAGAGCA CCTACTTCGA CCTTCCCAG TCAAGCCGA
```

GCTCCG  -STYI 101
CCTTGCA +STYI

```
sr-p70d-imr32                    CG ACCTTCCCCA GTCAAGCCGG GGGAATAATG  32
sr-p70a-hc29                     CG ACCTTCCCCA GTCAAGCCGG GGGAATAATG 150

AGGTGGTGGG CGGAACGGAT TCCAGCATGG ACGTCTTCCA CCTGGAGGGC  82
AGGTGGTGGG CGGAACGGAT TCCAGCATGG ACGTCTTCCA CCTGGAGGGC 200

ATGACTACAT CTGTCATGCA TCCTCGGCTC CTGCCTCACT AGCTGCGGAG 132
ATGACTACAT CTGTCAT... .......... .......... ..........  217

CCTCTCCCGC TCGGTCCACG CTGCCGGGCG GCCACGACCG TGACCCTTCC 182
.......... .......... .......... .......... ..........

CCTCGGGCCG CCCAGATCCA TGCCTCGTCC CACGGGACAC CAGTTCCCTG 232
.......... .......... .......... .......... ..........

GCGTGTGCAG ACCCCCGGC GGCTACCATG CTGTACGTCG GTGACCCCGC 282
.......... .......... .......... .......... ..........

ACGGCACCTC GCCACGGCCC AGTTCAATCT GCTGAGCAGC ACCATGGACC 332
.......... .....GGCCC AGTTCAATCT GCTGAGCAGC ACCATGGACC 252

AGATGAGCAG CCGCGCGGCC TCGGCCAGCC CCTACACCCC AGAGCACGCC 382
AGATGAGCAG CCGCGCGGCC TCGGCCAGCC CCTACACCCC AGAGCACGCC 302

GCCAGCGTGC CCACCCACTC GCCCTACGCA CAACCCAGCT CCACCTTCGA 432
GCCAGCGTGC CCACCCACTC GCCCTACGCA CAACCCAGCT CCACCTTCGA 352

CACCATGTCG CCGGCGCCTG TCATCCCCTC CAACACCGAC TACCCCGGAC 482
CACCATGTCG CCGGCGCCTG TCATCCCCTC CAACACCGAC TACCCCGGAC 402

CCCACCACTT TGAGGTCACT TTCCAGCAGT CCAGCACGGC CAAGTCAGCC 532
CCCACCACTT TGAGGTCACT TTCCAGCAGT CCAGCACGGC CAAGTCAGCC 452

ACCTGGACGT ACTCCCCGCT CTTGAAG
ACCTGGACGT ACTCCCCGCT CTTGAAG
```

PURIFIED SR-P70 PROTEIN

RELATED APPLICATIONS

This application is a continuation of U.S. application Ser. No. 09/125,005, filed on Jul. 30, 1998, now abandoned, which is the national stage of WO application number PCT/FR97/00214 filed on Feb. 3, 1997 which claims priority from French patent application number 9601309 filed Feb. 2, 1996.

The invention relates to new nucleic acid sequences of the family of tumour-suppressing genes related to the gene for the p53 protein, and to the corresponding protein sequences.

The invention also relates to the prophylactic, therapeutic and diagnostic applications of these sequences, in particular in the field of pathologies linked to the phenomena of apoptosis or of cell transformation.

Tumour-suppressing genes perform a key role in protection against the phenomena of carcinogenesis, and any modification capable of bringing about the loss of one of these genes, its inactivation or its dysfunction may have oncogenic character, thereby creating favourable conditions for the development of a malignant tumour.

The authors of the present invention have identified transcription products of a new gene, as well as the corresponding proteins. This gene, SR-p70, is related to the p53 tumour-suppressing gene, the antitumour activity of which is linked to its transcription factor activity, and more specifically to the controls exerted on the activity of the Bax and Bcl-2 genes which are instrumental in the mechanisms of cell death.

Hence the present invention relates to purified SR-p70 proteins, or biologically active fragments of the latter.

The invention also relates to isolated nucleic acid sequences coding for the said proteins or their biologically active fragments, and to specific oligonucleotides obtained from these sequences.

It relates, in addition, to the cloning and/or expression vectors containing at least one of the nucleotide sequences defined above, and the host cells transfected by these cloning and/or expression vectors under conditions permitting the replication and/or expression of one of the said nucleotide sequences.

The methods of production of recombinant SR-p70 proteins or their biologically active fragments by the transfected host cells also form part of the invention.

The invention also comprises antibodies or antibody derivatives specific for the proteins defined above.

It relates, in addition, to methods of detection of cancers, either by measuring the accumulation of SR-p70 proteins in the tumours according to immunohistochemical techniques, or by demonstrating autoantibodies directed against these proteins in patients' serum.

The invention also relates to any inhibitor or activator of SR-p70 activity, for example of protein-protein interaction, involving SR-p70.

It also relates to antisense oligonucleotide sequences specific for the above nucleic acid sequences, capable of modulating in vivo the expression of the SR-p70 gene.

Lastly, the invention comprises a method of gene therapy, in which vectors such as, for example, inactivated viral vectors capable of transferring coding sequences for a protein according to the invention are injected into cells deficient for this protein, for purposes of regulating the phenomena of apoptosis or of reversion of transformation.

A subject of the present invention is a purified polypeptide comprising an amino acid sequence selected from:
a) the sequence SEQ ID No. 2;
b) the sequence SEQ ID No. 4;
c) the sequence SEQ ID No. 6;
d) the sequence SEQ ID No. 8;
e) the sequence SEQ ID No. 10;
f) the sequence SEQ ID No. 13;
g) the sequence SEQ ID No. 15;
h) the sequence SEQ ID No. 17;
i) the sequence SEQ ID No. 19;
j) any biologically active sequence derived from SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19.

In the description of the invention, the following definitions are used:

SR-p70 protein: a polypeptide comprising an amino acid sequence selected from the sequences SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19, or any biologically active fragment or derivative of this polypeptide;

derivative: any variant polypeptide of the polypeptide of sequence SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19, or any molecule resulting from a modification of a genetic and/or chemical nature of the sequence SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19, that is to say obtained by mutation, deletion, addition, substitution and/or chemical modification of a single amino acid or of a limited number of amino acids, as well as any isoform sequence, that is to say sequence identical to the sequence SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19, or to one of its fragments or modified sequences, containing one or more amino acids in the form of the D enantiomer, the said variant, modified or isoform sequences having retained at least one of the properties that make them biologically active;

biologically active: capable of binding to DNA and/or of exerting transcription factor activity and/or of participating in the control of the cell cycle, of differentiation and of apoptosis and/or capable of being recognized by the antibodies specific for the polypeptide of sequence SEQ ID No. 2, SEQ ID No. 4, SEQ ID No. 6, SEQ ID No. 8, SEQ ID No. 10, SEQ ID No. 13, SEQ ID No. 15, SEQ ID No. 17 or SEQ ID No. 19, and/or capable of inducing antibodies which recognize this polypeptide.

The manufacture of derivatives may have different objectives, including especially that of increasing the affinity of the polypeptide for DNA or its transcription factor activity, and that of improving its levels of production, of increasing its resistance to proteases, of modifying its biological activities or of endowing it with new pharmaceutical and/or biological properties.

Among the polypeptides of the invention, the polypeptide of human origin comprising the sequence SEQ ID No. 6, SEQ ID No. 13, SEQ ID No. 15, SEQ ID No.17 or SEQ ID No. 19 is preferred. The polypeptide of 636 amino acids corresponding to the sequence SEQ ID No. 6 is more than 97% identical to the polypeptide of sequence SEQ ID No. 2.

The polypeptide of sequence SEQ ID No. 2 and that of sequence SEQ ID No. 4 are two expression products of the same gene, and the same applies to the sequences SEQ ID No. 8 and SEQ ID No. 10 and to the sequences SEQ ID No. 6, SEQ ID No. 13, SEQ ID No. 15, SEQ ID No. 17 or SEQ ID No. 19.

As will be explained in the examples, the polypeptide of sequence SEQ ID No. 4 corresponds to a premature termination of the peptide of sequence SEQ ID No. 2, linked to an alternative splicing of the longer transcript (messenger RNA), coding for the polypeptide of SEQ ID No. 2, of the corresponding gene. Similarly, in humans, the polypeptides corresponding to the sequences SEQ ID No. 6, SEQ ID No. 13, SEQ ID No. 15, SEQ ID No. 17 and SEQ ID No. 19, diverge in their composition in respect of the N- and/or C-terminal portions, this being the outcome of alternative splicing of the same primary transcript. The N-terminal peptide sequence of the sequence SEQ ID No. 10 is deleted, this being linked to an alternative splicing of its coding transcript.

Advantageously, the invention relates to a polypeptide corresponding to the DNA binding domain of one of the above polypeptides.

This domain corresponds to the sequence lying between residue 110 and residue 310 for the sequences SEQ ID No. 2 or 6, and between residue 60 and residue 260 for the sequence SEQ ID No. 8.

A subject of the present invention is also nucleic acid sequences coding for a SR-p70 protein or biologically active fragments or derivatives of the latter.

More preferably, a subject of the invention is an isolated nucleic acid sequence selected from:
a) the sequence SEQ ID No. 1;
b) the sequence SEQ ID No. 3;
c) the sequence SEQ ID No. 5;
d) the sequence SEQ ID No. 7;
e) the sequence SEQ ID No. 9;
f) the sequence SEQ ID No. 11;
g) the sequence SEQ ID No. 12;
h) the sequence SEQ ID No. 14;
i) the sequence SEQ ID No. 16;
j) the sequence SEQ ID No. 18;
k) the nucleic acid sequences capable of hybridizing specifically with the sequence SEQ ID No. 1, SEQ ID No. 3, SEQ ID No. 5, SEQ ID No. 7, SEQ ID No. 9, SEQ ID No. 11, SEQ ID No. 12, SEQ ID No. 14, SEQ ID No. 16 or SEQ ID No. 18 or with the sequences complementary to them, or of hybridizing specifically with their proximal sequences;
l) the sequences derived from the sequences a), b), c), d), e), f), g), h), i), j) or k) as a result of the degeneracy of the genetic code.

According to a preferred embodiment, a subject of the invention is nucleotide sequences SEQ ID No. 5, SEQ ID No. 12, SEQ ID No. 14, SEQ ID No. 16 and SEQ ID No. 18, corresponding, respectively, to the cDNAs of the human proteins of the sequences SEQ ID No. 6, SEQ ID No. 13, SEQ ID No. 15, SEQ ID No. 17 and SEQ ID No. 19.

The different nucleotide sequences of the invention may be of artificial origin or otherwise. They can be DNA or RNA sequences obtained by the screening of libraries of sequences by means of probes prepared on the basis of the sequences SEQ ID No. 1, 3, 5, 7, 9, 11, 12, 14, 16 or 18. Such libraries may be prepared by traditional techniques of molecular biology which are known to a person skilled in the art.

The nucleotide sequences according to the invention may also be prepared by chemical synthesis, or alternatively by mixed methods including the chemical or enzymatic modification of sequences obtained by the screening of libraries.

These nucleotide sequences enable nucleotide probes to be produced which are capable of hybridizing strongly and specifically with a nucleic acid sequence, of a genomic DNA or of a messenger RNA, coding for a polypeptide according to the invention or a biologically active fragment of the latter. Such probes also form part of the invention. They may be used as an in vitro diagnostic tool for the detection, by hybridization experiments, of transcripts specific for the polypeptides of the invention in biological samples, or for the demonstration of aberrant syntheses or of genetic abnormalities such as loss of heterozygosity or genetic rearrangement resulting from a polymorphism, from mutations or from a different splicing.

The probes of the invention contain at least 10 nucleotides, and contain at most the whole of the sequence of the SR-p70 gene or of its cDNA contained, for example, in a cosmid.

Among the shortest probes, that is to say of approximately 10 to 20 nucleotides, the appropriate hybridization conditions correspond to the stringent conditions normally used by a person skilled in the art.

The temperature used is preferably between $T_m - 5° C.$ and $T_m - 30° C.$, and as a further preference between $T_m - 5° C.$ and $T_m - 10° C.$, $T_m$ being the melting temperature, the temperature at which 50% of the paired DNA strands separate.

The hybridization is preferably conducted in solutions of high ionic strength, such as, in particular, 6×SSC solutions.

Advantageously, the hybridization conditions used are as follows:
temperature: 42° C.,
hybridization buffer: 6×SSC, 5× Denhart's, 0.1% SDS, as described in Example III.

Advantageously, these probes are represented by the following oligonucleotides or the sequences complementary to them:

```
SEQ ID No. 20:   GCG AGC TGC CCT CGG AG

SEQ ID No. 21:   GGT TCT GCA GGT GAC TCA G

SEQ ID No. 22:   GCC ATG CCT GTC TAC AAG

SEQ ID No. 23:   ACC AGC TGG TTG ACG GAG

SEQ ID No. 24:   GTC AAC CAG CTG GTG GGC CAG

SEQ ID No. 25:   GTG GAT CTC GGC CTC C

SEQ ID No. 26:   AGG CCG GCG TGG GGA AG

SEQ ID No. 27:   CTT GGC GAT CTG GCA GTA G

SEQ ID No. 28:   GCG GCC ACG ACC GTG AC

SEQ ID No. 29:   GGC AGC TTG GGT CTC TGG

SEQ ID No. 30:   CTG TAC GTC GGT GAC CCC

SEQ ID No. 31:   TCA GTG GAT CTC GGC CTC

SEQ ID No. 32:   AGG GGA CGC AGC GAA ACC

SEQ ID No. 33:   CCA TCA GCT CCA GGC TCT C

SEQ ID No. 34:   CCA GGA CAG GCG CAG ATG

SEQ ID No. 35:   GAT GAG GTG GCT GGC TGG A

SEQ ID No. 36:   TGG TCA GGT TCT GCA GGT G

SEQ ID No. 37:   CAC CTA CTC CAG GGA TGC

SEQ ID No. 38:   AGG AAA ATA GAA GCG TCA GTC

SEQ ID No. 39:   CAG GCC CAC TTG CCT GCC

SEQ ID No. 40:   CTG TCC CCA AGC TGA TGA G
```

Preferably, the probes of the invention are labelled prior to their use. To this end, several techniques are within the capacity of a person skilled in the art (fluorescent, radioactive, chemoluminescence, enzyme, and the like, labelling).

The in vitro diagnostic methods in which these nucleotide probes are employed are included in the subject of the present invention.

These methods relate, for example, to the detection of abnormal syntheses (e.g. accumulation of transcription products) or of genetic abnormalities, such as loss of heterozygosity and genetic rearrangement, and point mutations in the nucleotide sequences of nucleic acids coding for an SR-p70 protein, according to the definition given above.

The nucleotide sequences of the invention are also useful for the manufacture and use of oligonucleotide primers for sequencing reactions or specific amplification reactions according to the so-called PCR technique or any variant of the latter (ligase chain reaction (LCR), etc).

Preferred primer pairs consist of primers selected from the nucleotide sequences: SEQ ID No. 1: monkey sequence of 2,874 nucleotides, and SEQ ID No. 5: human SR-p70a cDNA, in particular upstream of the ATG translation initiation codon and downstream of the TGA translation stop codon.

Advantageously, these primers are represented by the following pairs:

pair No. 1:

sense primer:      GCG AGC TGC CCT    (SEQ ID No. 20)
                   CGG AG antisense primer:  GGT TCT GCA GGT    (SEQ ID No. 21)
                   GAC TCA G pair No. 2:

sense primer:      GCC ATG CCT GTC    (SEQ ID No. 22)
                   TAC AAG antisense primer:  ACC AGC TGG TTG    (SEQ ID No. 23)
                   ACG GAG pair No. 3:

sense primer:      GTC AAC CAG CTG    (SEQ ID No. 24)
                   GTG GGC CAG antisense primer:  GTG GAT CTC GGC    (SEQ ID No. 25)
                   CTC C pair No. 4:

sense primer:      AGG CCG GCG TGG    (SEQ ID No. 26)
                   GGA AG antisense primer:  CTT GGC GAT CTG    (SEQ ID No. 27)
                   GCA GTA G pair No. 5:

sense primer:      GCG GCC ACG ACC    (SEQ ID No. 28)
                   GTG A antisense primer:  GGC AGC TTG GGT    (SEQ ID No. 29)
                   CTC TGG pair No. 6:

sense primer:      CTG TAC GTC GGT    (SEQ ID No. 30)
                   GAC CCC antisense primer:  TCA GTG GAT CTC    (SEQ ID No. 31)
                   GGC CTC pair No. 7:

sense primer:      AGG GGA CGC AGC    (SEQ ID No. 32)
                   GAA ACC antisense primer:  GGC AGC TTG GGT    (SEQ ID No. 29)
                   CTC TGG pair No. 8:

sense primer:      CCCCCCCCCCCCCCN    (SEQ ID No. 41)
                   (where N equals
                   G, A or T)

antisense primer:  CCA TCA GCT CCA    (SEQ ID No. 33)
                   GGC TCT C pair No. 9:

sense primer:      CCCCCCCCCCCCCCN    (SEQ ID No. 41)
                   (where N equals
                   G, A or T)

antisense primer:  CCA GGA CAG GCG    (SEQ ID No. 34)
                   CAG ATG pair No. 10:

sense primer:      CCCCCCCCCCCCCCCN   (SEQ ID No. 41)
                   (where N equals
                   G, A or T)

antisense primer:  CTT GGC GAT CTG    (SEQ ID No. 27)
                   GCA GTA G pair No. 11:

sense primer:      CAC CTA CTC CAG    (SEQ ID No. 37)
                   GGA TGC antisense primer:  AGG AAA ATA GAA    (SEQ ID No. 38)
                   GCG TCA GTC pair No. 12:

sense primer:      CAG GCC CAC TTG    (SEQ ID No. 39)
                   CCT GCC antisense primer:  CTG TCC CCA AGC    (SEQ ID No. 40)
                   TGA TGA G These primers correspond to the sequences extending, respectively:

- from nucleotide No. 124 to nucleotide No. 140 on SEQ ID No. 1 and from nucleotide No. 1 to nucleotide No. 17 on SEQ ID No. 5 for SEQ ID No. 20
- from nucleotide No. 2280 to nucleotide No. 2262 on SEQ ID No. 1 and from nucleotide No. 2156 to nucleotide 2138 on SEQ ID No. 5 for SEQ ID No. 21
- from nucleotide No. 684 to nucleotide No. 701 on SEQ ID No. 1 for SEQ ID No. 22
- from nucleotide No. 1447 to nucleotide No. 1430 on SEQ ID No. 1 and from nucleotide 1324 to nucleotide 1307 on SEQ ID No. 5 for SEQ ID No. 23
- from nucleotide 1434 to nucleotide 1454 on SEQ ID No. 1 and from nucleotide 1311 to nucleotide 1331 on SEQ ID No. 5 for SEQ ID No. 24
- from nucleotide 2066 to nucleotide 2051 on SEQ ID No. 1 and from nucleotide 1940 to nucleotide 1925 on SEQ ID No. 5 for SEQ ID No. 25
- from nucleotide 16 to nucleotide 32 on SEQ ID No. 5 for SEQ ID No. 26
- from nucleotide 503 to nucleotide 485 on SEQ ID No. 5 for SEQ ID No. 27
- from nucleotide 160 to nucleotide 176 on SEQ ID No. 11 for SEQ ID No. 28
- from nucleotide 1993 to nucleotide 1976 on SEQ ID No. 5 for SEQ ID No. 29 from nucleotide 263 to nucleotide 280 on SEQ ID No. 11 for SEQ ID No. 30 from nucleotide 1943 to nucleotide 1926 on SEQ ID No. 5 for SEQ ID No. 31 from nucleotide 128 to nucleotide 145 on the nucleotide sequence depicted in FIG. 22 for SEQ ID No. 32 from nucleotide 1167 to nucleotide 1149 on SEQ ID No. 5 for SEQ ID No. 33 from nucleotide 928 to nucleotide 911 on SEQ ID No. 5 for SEQ ID No. 34 from nucleotide 677 to nucleotide 659 on SEQ ID No. 5 for SEQ ID No. 35 from nucleotide 1605 to nucleotide 1587 on SEQ ID No. 5 for SEQ ID No. 36 from nucleotide 1 to nucleotide 18 on the nucleotide sequence depicted in FIG. 13 for SEQ ID No. 37 from nucleotide 833 to nucleotide 813 on the nucleotide sequence depicted in FIG. 13 for SEQ ID No. 38 from nucleotide 25 to nucleotide 42 on the nucleotide sequence depicted in FIG. 13 for SEQ ID No. 39 from nucleotide 506 to nucleotide 488 on the nucleotide sequence depicted in FIG. 13 for SEQ ID No. 40

The nucleotide sequences according to the invention can have, moreover, uses in gene therapy, in particular for controlling the phenomena of apoptosis and of reversion of transformation.

The nucleotide sequences according to the invention may, moreover, be used for the production of recombinant SR-p70 proteins, according to the definition which has been given to this term.

These proteins may be produced from the nucleotide sequences defined above, according to techniques of production of recombinant products which are known to a person skilled in the art. In this case, the nucleotide sequence used is placed under the control of signals permitting its expression in a cell host.

An effective system for production of a recombinant protein necessitates having at one's disposal a vector, for example of plasmid or viral origin, and a compatible host cell.

The cell host may be selected from prokaryotic systems such as bacteria, or eukaryotic systems such as, for example, yeasts, insect cells, CHO cells (Chinese hamster ovary cells) or any other system advantageously available. A preferred cell host for the expression of proteins of the invention consists of the E. coli bacterium, in particular the strain MC 1061 (Clontec).

The vector must contain a promoter, translation initiation and termination signals and also the appropriate transcription regulation regions. It must be capable of being maintained stably in the cell and can, where appropriate, possess particular signals specifying the secretion of the translated protein.

These various control signals are selected in accordance with the cell host used. To this end, the nucleotide sequences according to the invention may be inserted into vectors which are autonomously replicating within the selected host, or vectors which are integrative for the chosen host. Such vectors will be prepared according to methods commonly used by a person skilled in the art, and the clones resulting therefrom may be introduced into a suitable host by standard methods such as, for example, electroporation.

The cloning and/or expression vectors containing at least one of the nucleotide sequences defined above also form part of the present invention.

A preferred cloning and expression vector is the plasmid pSE1, which contains the elements necessary for its use both as a cloning vector in E. coli (origin of replication in E. coli and ampicillin resistance gene originating from the plasmid pTZ 18R) and as an expression vector in animal cells (promoter, intron, polyadenylation site, origin of replication of the SV40 virus), as well as the elements enabling it to be copied as a single strand with the object of sequencing (origin of replication of phage f1).

The characteristics of this plasmid are described in Application EP 0,506,574.

Its construction and also the integration of the cDNAs originating from the nucleic acid sequences of the invention are, moreover, described in the examples below. According to a preferred embodiment, the proteins of the invention are in the form of fusion proteins, in particular in the form of a protein fused with glutathione S-transferase (GST). A designated expression vector in this case is represented by the plasmid vector pGEX-4T-3 (Pharmacia ref-27.4583).

The invention relates, in addition, to the host cells transfected by these aforementioned vectors. These cells may be obtained by introducing into host cells a nucleotide sequence inserted into a vector as defined above, followed by culturing of the said cells under conditions permitting the replication and/or expression of the transfected nucleotide sequence.

These cells are usable in a method of production of a recombinant polypeptide of sequence SEQ ID No. 2, SEQ ID No. 4, SEQ ID No. 6, SEQ ID No. 8, SEQ ID No. 10, SEQ ID No. 12, SEQ ID No. 14, SEQ ID No. 16 or SEQ ID No. 18 or any biologically active fragment or derivative of the latter.

The method of production of a polypeptide of the invention in recombinant form is itself included in the present invention, and is characterized in that the transfected cells are cultured under conditions permitting the expression of a recombinant polypeptide of sequence SEQ ID No. 2, SEQ ID No. 4, SEQ ID No. 6, SEQ ID No. 8, SEQ ID No. 10, SEQ ID No. 12, SEQ ID No. 14, SEQ ID No. 16 or SEQ ID No. 18 or of any biologically active fragment or derivative of the latter, and in that the said recombinant polypeptide is recovered.

The purification methods used are known to a person skilled in the art. The recombinant polypeptide may be purified from lysates and cell extracts or from the culture medium supernatant, by methods used individually or in combination, such as fractionation, chromatographic methods, immunoaffinity techniques using specific mono- or polyclonal antibodies, and the like. A preferred variant consists in producing a recombinant polypeptide fused to a "carrier" protein (chimeric protein). The advantage of this system is that it permits a stabilization and a decrease in proteolysis of the recombinant product, an increase in solubility during in vitro renaturation and/or a simplification of the purification when the fusion partner possesses an affinity for a specific ligand.

Advantageously, the polypeptides of the invention are fused with glutathione S-transferase at the N-terminal position (Pharmacia "GST" system). The fusion product is, in this case, detected and quantified by means of the enzyme activity of the GST. The colorimetric reagent used is a glutathione acceptor, a substrate for GST. The recombinant product is purified on a chromatographic support to which glutathione molecules have been coupled beforehand.

The mono- or polyclonal antibodies capable of specifically recognizing an SR-p70 protein according to the definition given above also form part of the invention. Polyclonal antibodies may be obtained from the serum of an animal immunized against protein, produced, for example, by genetic recombination according to the method described above, according to standard procedures.

The monoclonal antibodies may be obtained according to the traditional hybridoma culture method described by Köhler and Milstein, Nature, 1975, 256, 495-497.

Advantageous antibodies are antibodies directed against the central region lying between residue 110 and residue 310 for the sequences SEQ ID No. 2 or 6, or between residue 60 and residue 260 for the sequence SEQ ID No. 8.

The antibodies according to the invention are, for example, chimeric antibodies, humanized antibodies or Fab and F(ab')$_2$ fragments. They may also take the form of immunoconjugates or labelled antibodies.

Moreover, besides their use for the purification of the recombinant polypeptides, the antibodies of the invention, especially the monoclonal antibodies, may also be used for detecting these polypeptides in a biological sample.

Thus they constitute a means of immunocytochemical or immunohistochemical analysis of the expression of SR-p70 proteins on sections of specific tissues, for example by immunofluorescence, gold labelling or enzyme immunoconjugates.

They make it possible, in particular, to demonstrate an abnormal accumulation of SR-p70 proteins in certain tissues or biological samples, which makes them useful for detecting cancers or monitoring the progression or remission of pre-existing cancers.

More generally, the antibodies of the invention may be advantageously employed in any situation where the expression of an SR-p70 protein has to be observed.

Hence the invention also relates to a method of in vitro diagnosis of pathologies correlated with an expression or an abnormal accumulation of SR-p70 proteins, in particular the phenomena of carcinogenesis, from a biological sample, characterized in that at least one antibody of the invention is brought into contact with the said biological sample under conditions permitting the possible formation of specific immunological complexes between an SR-p70 protein and the said antibody or antibodies, and in that the specific immunological complexes possibly formed are detected.

The invention also relates to a kit for the in vitro diagnosis of an expression or an abnormal accumulation of SR-p70 proteins in a biological sample and/or for measuring the level of expression of this protein in the said sample, comprising:

at least one antibody specific for an SR-p70 protein, optionally bound to a support, means of visualization of the formation of specific antigen-antibody complexes between an SR-p70 protein and the said antibody, and/or means of quantification of these complexes.

The invention also relates to a method of early diagnosis of tumour formation, by detecting autoantibodies directed against an SR-p70 protein in an individual's serum.

Such a method of early diagnosis is characterized in that a serum sample drawn from an individual is brought into contact with a polypeptide of the invention, optionally bound to a support, under conditions permitting the formation of specific immunological complexes between the said polypeptide and the autoantibodies possibly present in the serum sample, and in that the specific immunological complexes possibly formed are detected.

A subject of the invention is also a method of determination of an allelic variability, a mutation, a deletion, an insertion, a loss of heterozygosity or a genetic abnormality of the SR-p70 gene which may be involved in pathologies, characterized in that it utilizes at least one nucleotide sequence described above. Among the methods of determination of an allelic variability, a mutation, a deletion, an insertion, a loss of heterozygosity or a genetic abnormality of the SR-p70 gene, preference is given to the method which is characterized in that it comprises at least one step of PCR amplification of the target nucleic acid sequence of SR-p70 liable to exhibit a polymorphism, a mutation, a deletion or an insertion, using a pair of primers of nucleotide sequences defined above, a step during which the amplified products are treated using a suitable restriction enzyme and a step during which at least one of the products of the enzyme reaction is detected or assayed.

The invention also comprises pharmaceutical compositions comprising as active principle a polypeptide corresponding to the above definitions, preferably in soluble form, in combination with a pharmaceutically acceptable vehicle.

Such compositions afford a novel approach to treating the phenomena of carcinogenesis at the level of the control of multiplication and cell differentiation.

Preferably, these compositions can be administered systemically, preferably intravenously, intramuscularly, intradermally or orally.

Their optimal modes of administration, dosages and pharmaceutical dosage forms may be determined according to the criteria generally borne in mind in establishing a therapeutic treatment suitable for a patient, such as, for example, the patient's age or body weight, the severity of his or her general state, the tolerability of treatment and the observed side effects, and the like.

Lastly, the invention comprises a method of gene therapy, in which nucleotide sequences coding for an SR-p70 protein are transferred to target cells by means of inactivated viral vectors.

Other features and advantages of the invention are to be found in the remainder of the description, with the examples and the figures for which the legends are given below.

BRIEF DESCRIPTION OF THE DRAWINGS

| | |
|---|---|
| FIG. 1A and 1B: | Nucleic acid comparison of monkey SR-p70a cDNA (corresponding to nucleotides 1-1599 of SEQ ID No. 1) with the nucleic acid sequence of monkey p53 cDNA (SEQ ID No. 43). |
| FIG. 2: | Protein comparison of monkey SR-p70a amino acids 1-450 of SEQ ID No. I with monkey p53 protein (SEQ ID No. 44) (sw: p53-cerae). |
| FIG. 3A-C: | Comparison of the nucleic acid sequence of monkey SR-p70a and b cDNA (corresponding, respectively, to SEQ ID No. 1 and SEQ ID No. 3). |
| FIG. 4A and 4B: | Nucleic acid sequence (SEQ ID No. 1) and deduced protein sequence (SEQ ID No. 2) of monkey SR-p70a. |
| FIG. 5: | Partial nucleic acid sequence (SEQ ID No. 3) and complete deduced protein sequence (SEQ ID No. 4) of monkey SR-p70b. |

-continued

BRIEF DESCRIPTION OF THE DRAWINGS

Figure 10A:
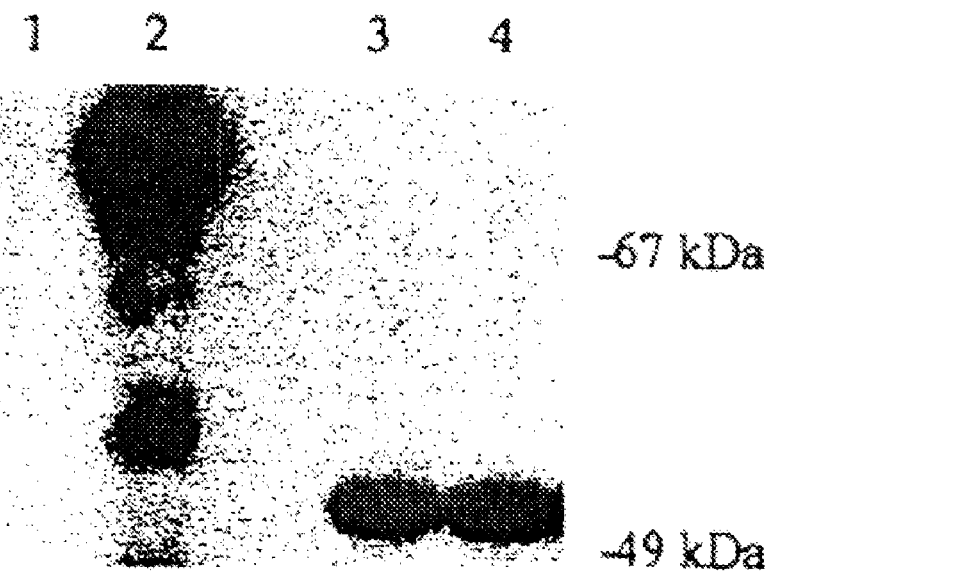
Figure 10B:
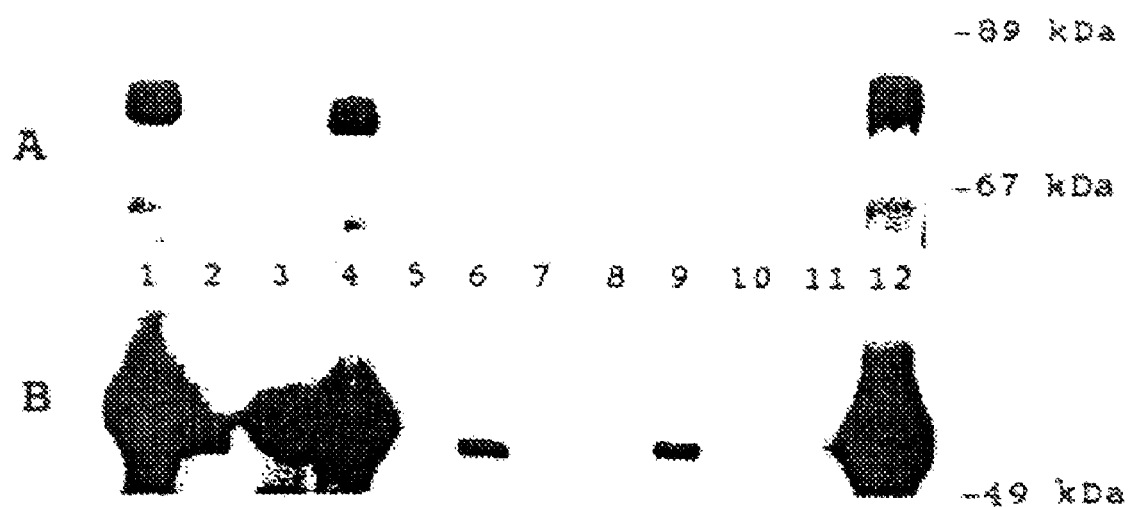
Figure 11:
Figure 15A:
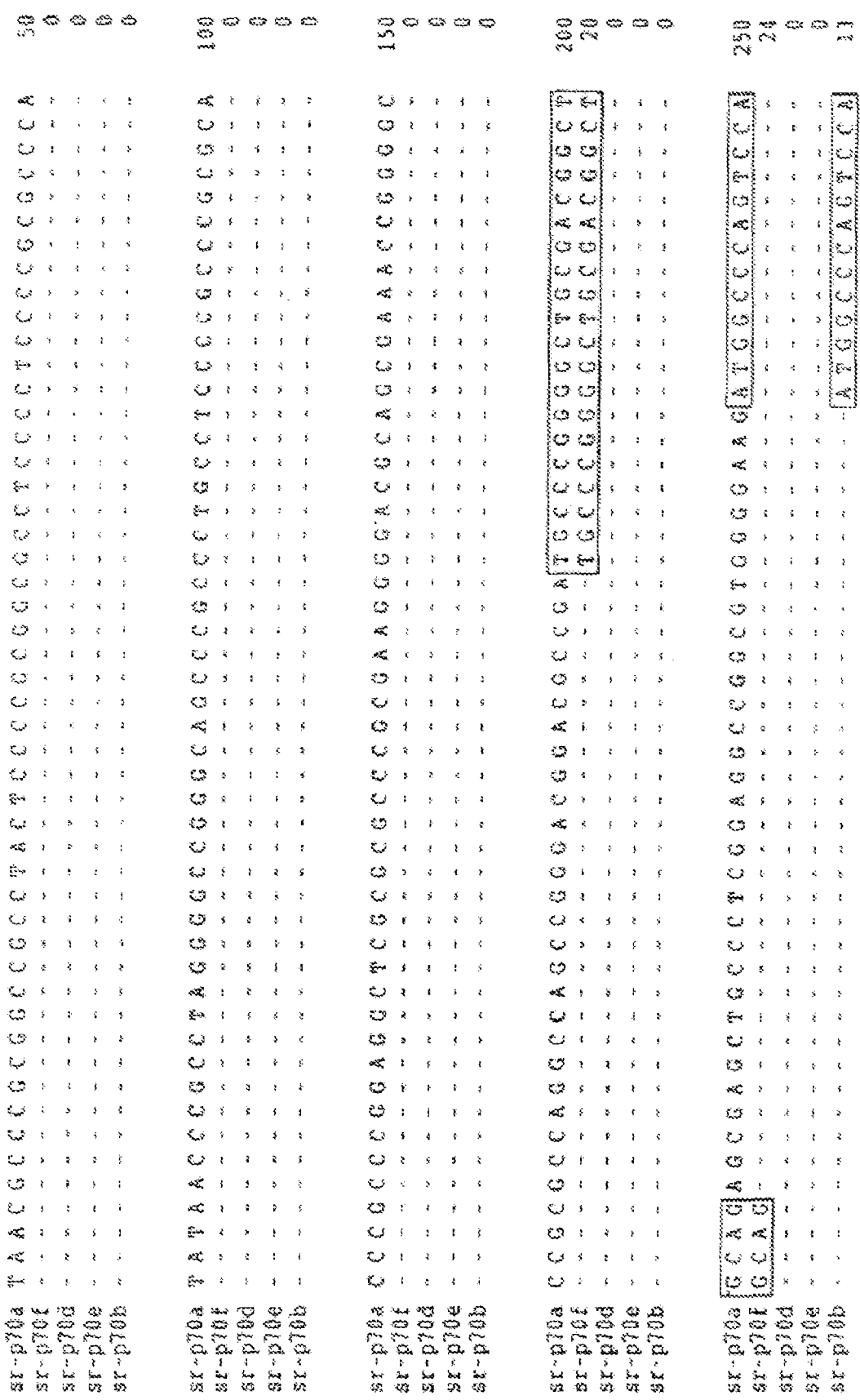
Figure 19A:
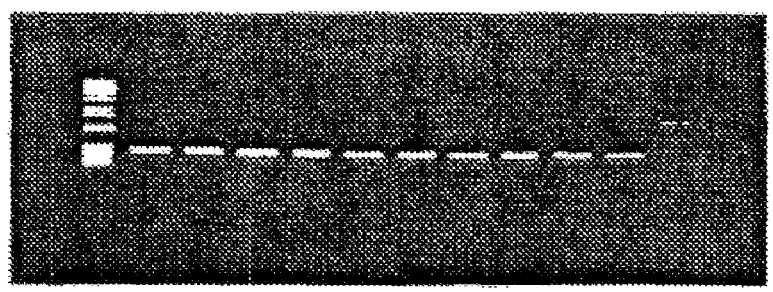
Figure 19B:
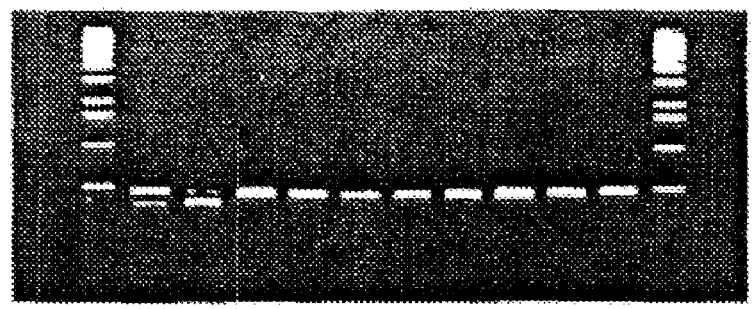
Figure 20:
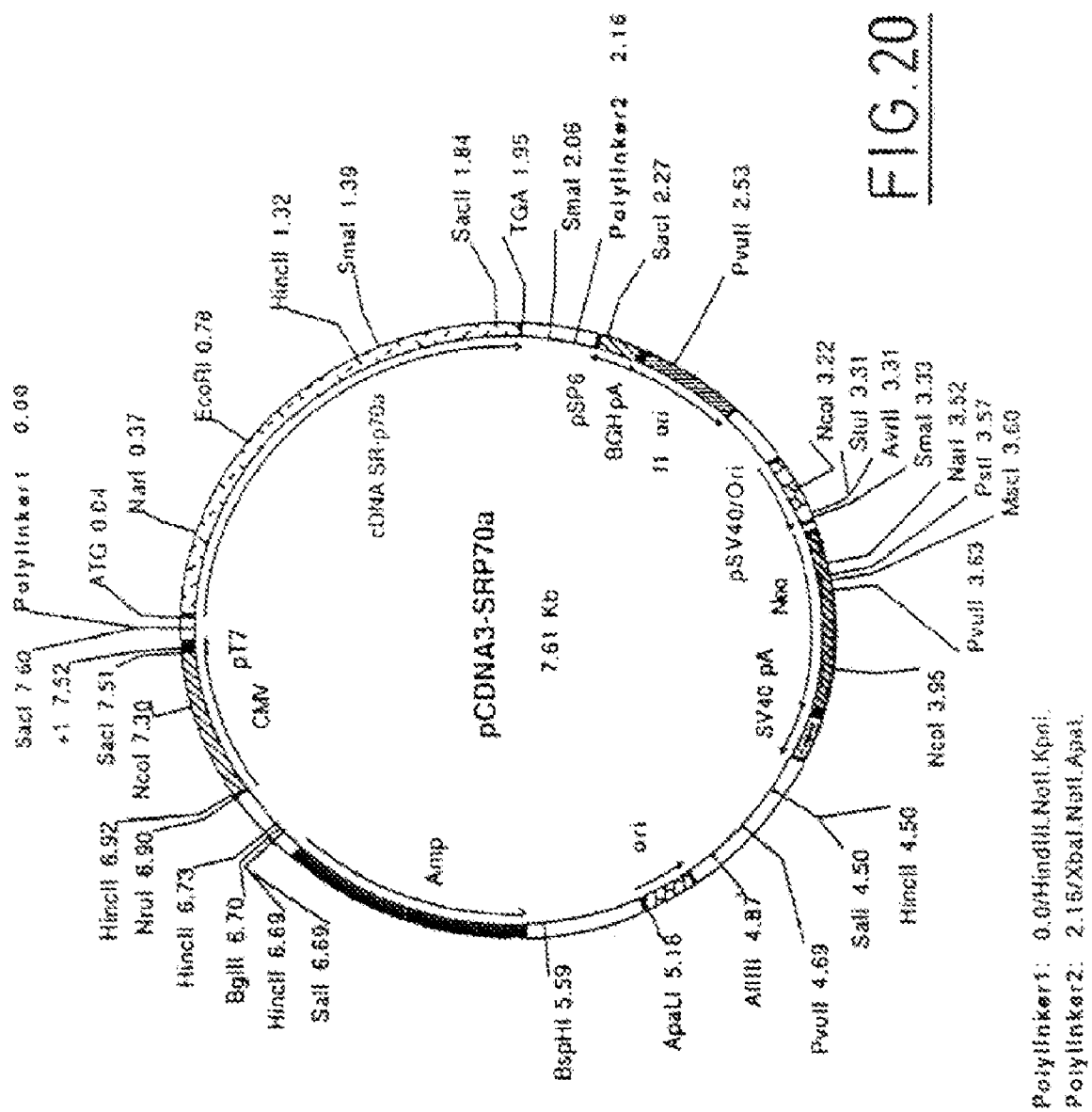

| | |
|---|---|
| FIG. 6A and 6B: | Partial nucleic acid sequence (SEQ ID No. 5) and deduced complete protein sequence (SEQ ID No. 6) of human SR-p70a. |
| FIG. 7: | Partial nucleic acid sequence (SEQ ID No. 7) and complete deduced protein sequence (SEQ ID No. 8) of mouse SR-p70c. |
| FIG. 8: | Partial nucleic acid sequence (SEQ ID No. 9) and partially deduced protein sequence (SEQ ID No. 10) of mouse SR-p70a. |
| FIG. 9A and 9B: | Multialignment of the proteins deduced from monkey (SR-p70a-cos3 and SR-p70b-cos3) (SEQ ID No. 2 and SEQ ID No. 4, respectively), human (SR-p70-ht29) and mouse (SR-p70c-att20 and sr-p70a-att20) (SEQ ID No. 10 and SEQ ID No. 8, respectively) SR-p70 cDNAs. |
| FIG. 10a: | Immunoblot of the SR-p70 protein. |
| FIG. 10b: | Detection of the endogenous SR-p70 protein. |
| FIG. 11: | Chromosomal localization of the human SR-p70 gene. The signal appears on chromosome 1, in the p36 region. |
| FIG. 12: | Genomic structure of the SR-p70 gene and comparison with that of the p53 gene. The human protein sequences of SR-p70a (SEQ ID No. 6) (upper line of the alignment) and of p53 (SEQ ID No. 45) (lower line) are divided up into peptides on the basis of the respective exons from which they are encoded. The figures beside the arrows correspond to the numbering of the corresponding exons. |
| FIG. 13: | Human genomic sequence of SR-p70 from the 3' end of intron 1 to the 5' end of exon 3 (SEQ ID No. 46). The introns are boxed. At positions 123 and 133, two variable nucleic acid positions are localized (G → A at 123 and C → T at 133). The restriction sites for the enzyme StyI are underlined (position 130 in the case where a T is present instead of a C at position 133, position 542 and position 610). The arrows indicate the positions of the nucleic acid primers used in Example XI. |
| FIG. 14: | Nucleic acid comparison of the 5' region of the human cDNAs of SR-p70d (SEQ ID No. 12) and of SR-p70a (SEQ ID No. 5). |
| FIG. 15A-J: | Multialignment of the nucleic acid sequences corresponding to human SR-p70a, b, d, e, and f (SEQ ID No. 5, SEQ ID No. 18, SEQ ID No. 12, SEQ ID No. 14 and SEQ ID No. 16, respectively). |
| FIG. 16A-C: | Multialignment of the proteins deduced from human SR-p70 (a, b, d, e and f) (SEQ ID No. 6, SEQ ID No. 19, SEQ ID No. 13, SEQ ID No. 15 and SEQ ID No. 17, respectively), cDNA's. |
| FIG. 17: | Partial nucleic acid sequence (SEQ ID No. 5) and partial deduced protein sequence (SEQ ID No. 6) of human SR-p70a. The two bases in bold characters correspond to two variable positions (see FIG. 6). This sequence possesses a more complete non-coding 5' region than the one presented in FIG. 6. |
| FIG. 18: | Analysis of the SR-p70a transcripts after PCR amplification.<br>lane M: 1 kb ladder (GIBCO-BRL) molecular weight markers<br>lane 1: line HT29<br>lane 3: line SK-N-AS<br>lane 5: line UMR-32<br>lane 7: line U-373 MG<br>lane 9: line SW 480<br>lane 11: line CHP 212<br>lane 13: line SK-N-MC<br>lanes 2, 4, 6, 8, 10, 12, 14: negative controls corresponding to lanes 1, 3, 5, 7, 9, 11 and 13, respectively (absence of inverse transcriptase in the RT-PCR reaction). |
| FIG. 19A and 19B: | A: Analysis by agarose gel electrophoresis of genomic fragments amplified by PCR (from the 3' end of intron 1 to the 5' end of exon 3). The numbering of the lanes corresponds to the numbering of the control population. Lane M: molecular weight markers (1 kb ladder).<br>B: Analysis identical to that of part A, after digestion of the same samples with the restriction enzyme StyI. |
| FIG. 20: | Diagrammatic representation with a partial restriction map of the plasmid pCDNA3 containing human SR-p70a. |

EXAMPLE I

Cloning of SR-p70 CDNA from COS-3 Cells

1. Culturing of COS-3 Cells

COS-3 cells (African green monkey kidney cells transformed with the SV 40 virus T antigen) are cultured in DMEM medium (GIBCO-BRL reference 41 965-047) containing 2 mM L-glutamine and supplemented with 50 mg/l of gentamicin and 5% of foetal bovine serum (GIBCO-BRL reference 10231-074) to semi-confluence.

2. Preparation of the Messenger RNA a) Extraction of the messenger RNA

The cells are recovered in the following manner:

the adherent cells are washed twice with PBS buffer (phosphate buffered saline, reference 04104040-GIBCO-BRL), then scraped off with a rubber scraper and centrifuged.

The cell pellet is suspended in the lysis buffer of the following composition: 4 M guanidine thiocyanate; 25 mM sodium citrate pH 7; 0.5% sarcosyl; 0.1 M β-mercaptoethanol. The suspension is sonicated using an Ultra-Turrax No. 231256 sonicator (Janke and Kundel) at maximum power for one minute. Sodium acetate pH 4 is added to a concentration of 0.2 M. The solution is extracted with one volume of a phenol/chloroform (5:1 v/v) mixture. The RNA contained in the aqueous phase is precipitated at −20° C. using one volume of isopropanol. The pellet is resuspended in the lysis buffer. The solution is extracted again with a phenol/chloroform mixture and the RNA is precipitated with isopropanol. After washing of the pellet with 70% and then 100% ethanol, the RNA is resuspended in water.

b) Purification of the poly(A)$^+$ fraction of the RNA

Purification of poly(A)$^+$ fraction of the RNA is carried out using the DYNAL Dynabeads oligo(dT)$_{25}$ kit (reference 610.05) according to the protocol recommended by the manufacturer. The principle is based on the use of superparamagnetic polystyrene beads to which an oligonucleotide poly(dT)$_{25}$ is attached. The poly(A)$^+$ fraction of the RNA is hybridized with the oligo(dT)$_{25}$ coupled to the beads, which are trapped on a magnetic support.

3. Production of the complementary DNA library a) Preparation of the Complementary DNA From 0.5 µg of the poly(A)$^+$ RNA from COS-3 cells obtained at the end of step 2, the [$^{32}$P]dCTP-labelled single-stranded complementary DNA is prepared (the complementary DNA obtained possesses a specific activity of 3000 dpm/ng) with the synthetic primer of the following sequence (comprising a BamHI site):

(SEQ ID No. 47)
5'<GATCCGGGCC CTTTTTTTTT TTT<3' in a volume of 30 µl of buffer of composition: 50 mM Tris-HCl pH 8.3, 6 mM MgCl$_2$, 10 mM DDT, 40 mM KCl, containing 0.5 mM each of the deoxynucleotide triphosphates, 30 µCi of [α-$^{32}$P]dCTP and 30 U of RNasin (Promega). After one hour of incubation at 37° C., then 10 minutes at 50° C., then 10 minutes again at 37° C., with 200 units of the enzyme reverse transcriptase RNase H$^-$ (GIBCO-BRL reference 8064A), 4 µl of EDTA are added.

b) Alkaline hydrolysis of the RNA template

6 µl of 2N NaOH solution are added and the mixture is then incubated for 5 minutes at 65° C.

c) Purification on a Sephacryl S-400 column

In order to remove the synthetic primer, the complementary DNA is purified on a column of 1 ml of Sephacryl S-400 (Pharmacia) equilibrated in TE buffer.

The first two radioactive fractions are pooled and precipitated with 1/10 volume of 10 M ammonium acetate solution and 2.5 volumes of ethanol, this being done after extraction with one volume of chloroform.

d) Homopolymer addition of dG

The complementary DNA is elongated at the 3' end with a dG tail with 20 units of the enzyme terminal transferase (Pharmacia 27073001). The mixture is incubated in 20 µl of buffer of composition: 30 mM Tris-HCl pH 7.6, 1 mM cobalt chloride, 140 mM cacodylic acid, 0.1 mM DTT, 1 mM dGTP, for 15 minutes at 37° C., and 2 µl of 0.5 M EDTA are then added.

e) Steps b) and c) are repeated again f) Pairing of the cloning vector pSE1 (EP 506,574) and the complementary DNA in the presence of the adaptor.

The mixture is centrifuged, the pellet is dissolved in 33 µl of TE buffer, 5 µl (125 ng) of cloning vector pSE1, 1 µl (120 ng) of the adaptor of the following sequence (comprising an ApaI site):

(SEQ ID No. 48)
5'AAAAAAAAAAAAAGGGCCCG3' and 10 µl of 200 mM NaCl solution are added, and the reaction mixture is incubated for 5 minutes at 65° C. and then allowed to cool to room temperature.

g) Ligation

The cloning vector and the single-stranded cDNA are ligated in a volume of 100 µl with 32.5 units of the enzyme phage T4 DNA ligase (Pharmacia reference 270 87002) overnight at 15° C. in a buffer of composition: 50 mM Tris-HCl pH 7.5, 10 mM MgCl$_2$, 1 mM ATP.

h) Synthesis of the second strand of the cDNA

The proteins are removed by phenol extraction followed by chloroform extraction, and 1/10 volume of 10 mM ammonium acetate solution and then 2.5 volumes of ethanol are then added. The mixture is centrifuged, the pellet is dissolved in a buffer of composition 33 mM Tris-acetate pH 7.9, 62.5 mM potassium acetate, 1 mM magnesium acetate and 1 mM dithiothreitol (DTT), and the second strand of complementary DNA is synthesized in a volume of 30 µl with 30 units of the enzyme phage T4 DNA polymerase (Pharmacia reference 270718) and a mixture of 1 mM the four deoxynucleotide triphosphates dATP, dCTP, dGTP and dTTP as well as two units of phage T4 gene 32 protein (Pharmacia reference 27-0213) for one hour at 37° C. The mixture is extracted with phenol and the traces of phenol are removed with a column of polyacrylamide P10 (Biogel P10-200-400 mesh—reference 15011050—Biorad).

i) Transformation by electroporation

E. coli MC 1061 cells are transformed with the recombinant DNA obtained above by electroporation using a Biorad Gene Pulser apparatus (Biorad) used at 2.5 kV under the conditions specified by the manufacturer, and the bacteria are then grown for one hour in the medium known as LB medium (Sambrook op. cit.) of composition: bactotryptone 10 g/l; yeast extract 5 g/l; NaCl 10 g/l.

The number of independent clones is determined by plating out a 1/1000 dilution of the transformation after the first hour of incubation on a dish of LB medium with the addition of 1.5% of agar (w/v) and 100 µg/ml of ampicillin, hereinafter referred to as LB agar medium. The number of independent clones is 1 million.

j) Analysis of the cDNAs of the Library

Figure 1A:
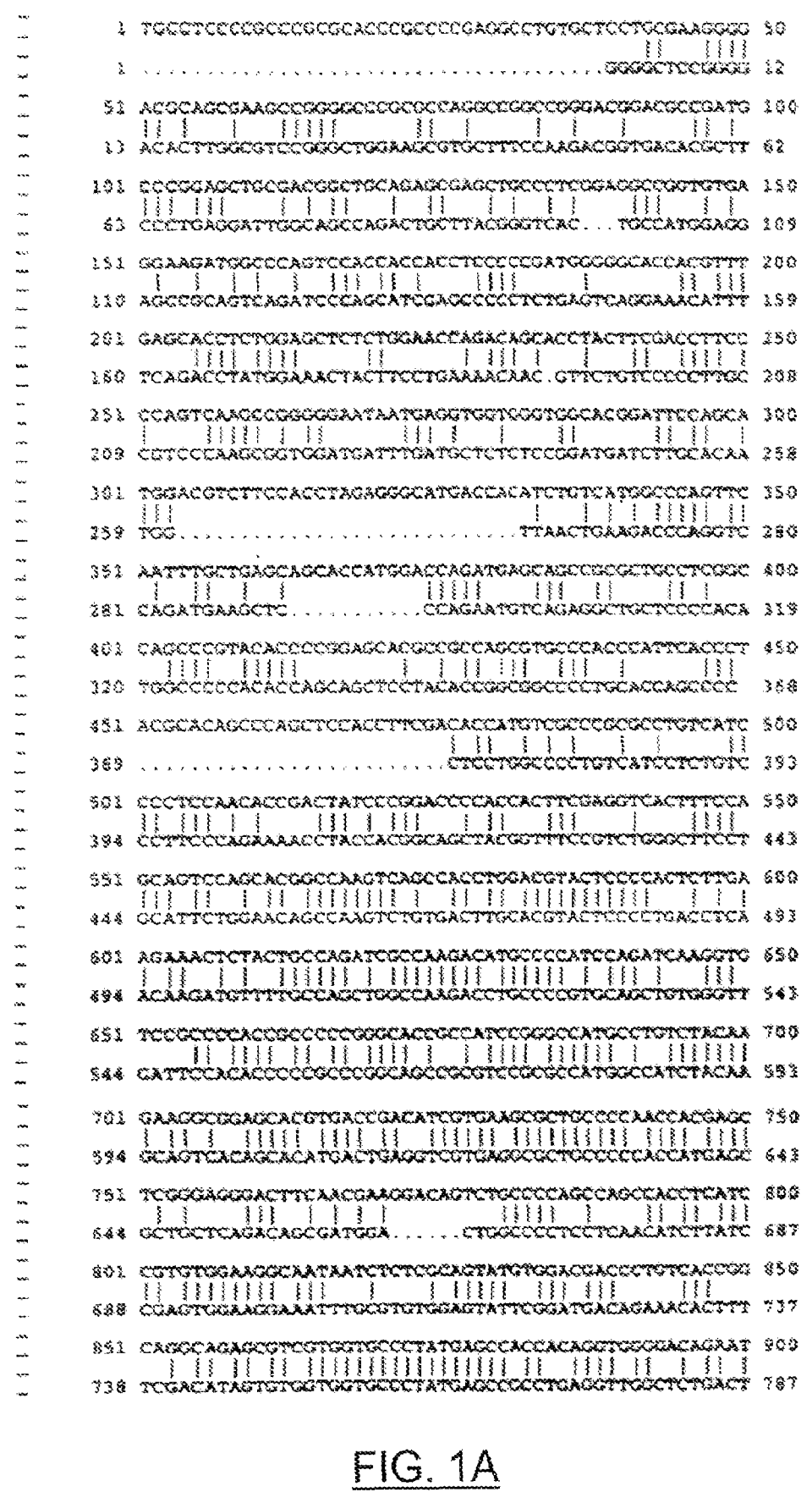

In the context of the analysis of individual clones of the library by nucleic acid sequencing of the 5' region of the cDNAs, one clone, designated SR-p70a, was shown to exhibit a partial homology with the cDNA of the already known protein, the p53 protein (Genbank X 02469 and X 16384) (FIG. 1). The sequences were produced with the United States Biochemical kit (reference 70770) and/or the Applied Biosystems kit (references 401434 and/or 401628), which use the method of Sanger et al., Proc. Natl. Acad. Sci. USA; 1977, 14, 5463-5467. The plasmid DNA is prepared from the WIZARD minipreparation kit (Promega reference A7510). The primers used are 16- to 22-mer oligonucleotides, complementary either to the vector pSE1 in the region immediately at the 5' end of the CDNA, or to the sequence of the cDNA.

A second cDNA was isolated from the same library by screening, in a manner similar to the technique described in EXAMPLE III.3) below, with a fragment of SR-p70a the DNA labelled with $^{32}$P with the BRL "Random Primers DNA labelling systems" kit (reference 18187-013). The hybridization and washing buffers are treated by adding 50% of formamide. The last wash is carried out in 0.1×SSC/0.1% SDS at 60° C. This second sequence (SR-p70b cDNA) is identical to the first but an internal fragment has been deleted from it (FIG. 3).

Figure 5:
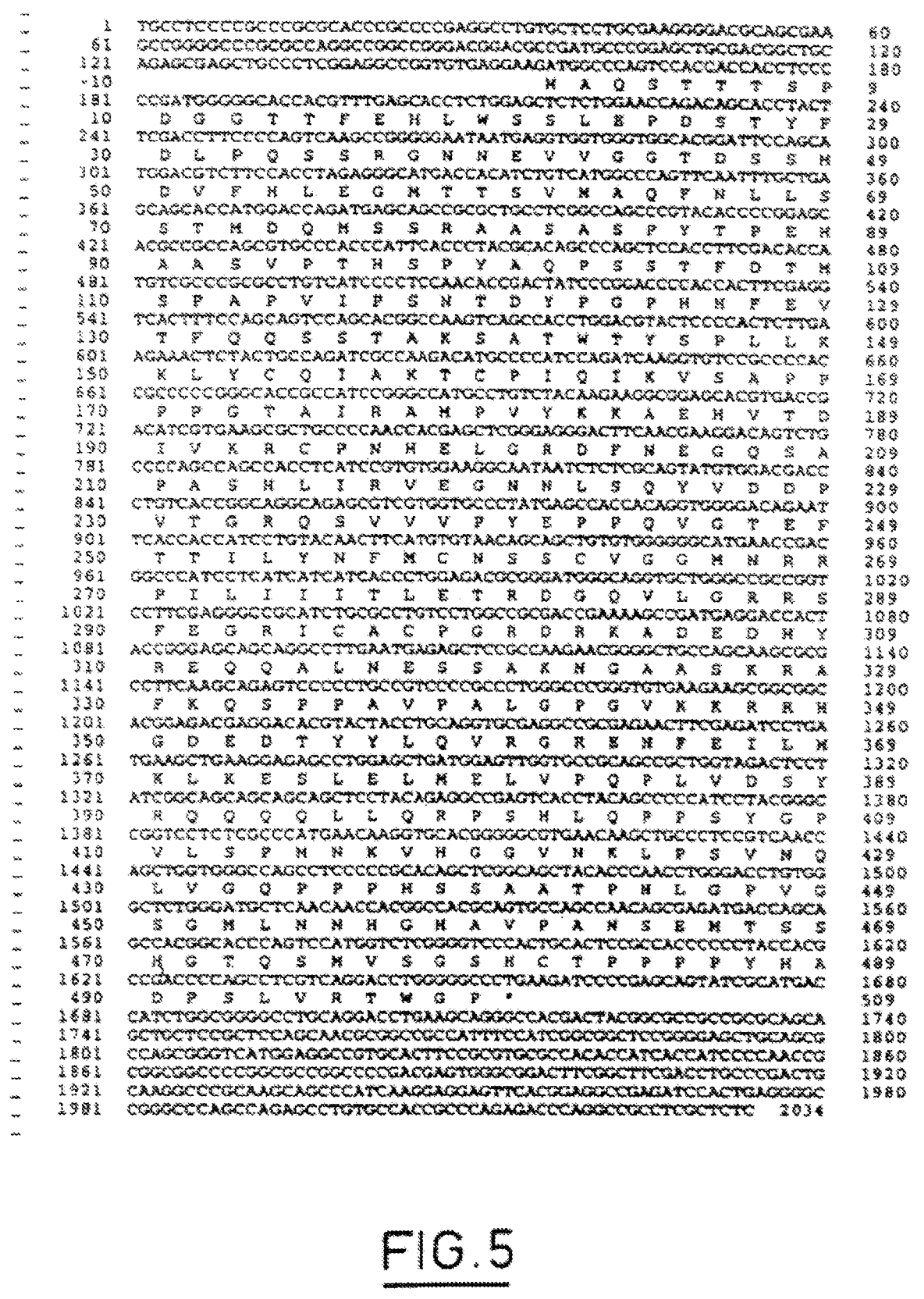

The two SR-p70 cDNAs, of length 2874 nucleotides (SR-p70a) and 2780 nucleotides (SR-p70b), correspond to the products of a single gene, an alternative splicing bringing about a deletion of 94 bases between nucleotides 1637 and 1732 and a premature termination of the corresponding encoded protein. The proteins deduced from the two cDNAs possess 637 amino acids and 499 amino acids, respectively (FIGS. 4 and 5).

EXAMPLE II

Obtaining of the Sequence and Cloning of the cDNA of the SR-p70a Protein from HT-29 (Human Colon Adenocarcinoma) Cells 1) Culturing of HT-29 Cells The cells are cultured in McCoy's 5 medium (GIBCO 26600-023) with the addition of 10% of foetal calf serum (GIBCO 10081-23) and 50 mg/l of gentamicin, to semi-confluence.

2) Preparation of the Complementary DNA

The messenger RNA is prepared as described in EXAMPLE I.2. The cDNA is prepared in a manner similar to that described in EXAMPLE I.3, with 5 µg of total messenger RNA, using a poly(T)$_{12}$ primer. The reaction is not interrupted with EDTA.

3) Specific Amplification of the Human cDNA by the So-Called PCR Technique

The polymerization is carried out with 4 µl of cDNA in 50 µl final with the buffer of the following composition: 10 mM Tris-HCl pH 8.3, 2.5 mM MgCl$_2$, 50 mM KC in the presence of 10% DMSO, 0.5 mM dNTP, 4 µg/ml of each of the two nucleic acid primers and 2.5 units of TAQ DNA polymerase (Boehringer). The primer pairs were selected on the basis of the nucleic acid sequence of the COS-3 SR-p70 clone, in particular upstream of the translation initiation ATG and downstream of the translation stop TGA, and are of the following compositions:

```
                                            (SEQ ID No. 49)
sense primer: ACT GGT ACC GCG AGC TGC CCT CGG AG
              Kpn I restriction site (SEQ ID No. 50)
antisense     GAC TCT AGA GGT TCT GCA GGT GAC TCA G
primer:       Xba I restriction site
```

The reaction is carried out for 30 cycles of 94° C./1 minute, 54-60° C./1 minute 30 seconds and 72° C./ 1 minute 30 seconds, followed by a final cycle of 72° C./6 minutes.

4) Obtaining of the Sequence of the Human cDNA

In a first step, the PCR product is removed from the oligonucleotides on a column of Sephacryl S-400, and then desalted by exclusion chromatography on a column of polyacrylamide P10 (Biorad reference 1504144). The sequencing reactions are carried out using the Applied Biosystems kit (reference 401628) with oligonucleotides specific for the cDNA. The sequence obtained is very similar to that of monkey SR-p70a, and the deduced protein contains 636 amino acids (FIG. 6).

In a similar manner, other sequences originating from human lines or tissues were obtained for the coding portion of human SR-p70, in particular from the lung or pancreas. The proteins deduced from these sequences are identical to those obtained for the HT-29 line.

5) Cloning of the Human CDNA into Plasmid pCDNA3 (Invitrogen V 790-20)

The PCR product obtained in 3) and also the plasmid are digested with the two restriction enzymes Kpn I and Xba I and then purified after migration on a 1% agarose gel using the Geneclean kit (Bio 101 reference 3105). After ligation with 100 ng of insert and 10 ng of vector and transformation (technique described in EXAMPLE I.3.g and i), the recombinant clones are verified by sequencing using the Applied Biosystems kit mentioned above.

EXAMPLE III

Cloning of Mouse SR-p70 cDNA from AtT-20 (Pituitary Tumour) Cells

1) Cell Culturing of the Line AtT-20

The cells are cultured in Ham F10 medium (GIBCO 31550-023) with the addition of 15% of horse serum (GIBCO 26050-047), 2.5% of foetal calf serum (GIBCO 10081-073) and 50 mg/l of gentamicin, to semi-confluence.

2) Preparation of the Complementary DNA Library

The library is produced as described in EXAMPLE I.2 and 3 from the cells cultured above.

3) Screening of the Library a) Preparation of the membranes

The clones of the library are plated out on LB agar medium (Petri dishes 150 mm in diameter) coated with Biodyne A membranes (PALL reference BNNG 132). After one night at 37° C., the clones are transferred by contact onto fresh membranes. The latter are treated by depositing them on 3 mm Whatman paper soaked with the following solutions: 0.5 N NaOH, 1.5 M NaCl for 5 minutes, then 0.5 M Tris-HCl pH 8, 1.5 M NaCl for 5 minutes. After treatment with proteinase K in the following buffer: 10 mM Tris-HCl pH 8, 10 mM EDTA, 50 mM NaCl, 0.1% SDS, 100 µg/ml proteinase K, for one hour at room temperature, the membranes are washed copiously in 2×SSC (sodium citrate, NaCl), dried and then incubated in an oven under vacuum at 80° C. for 20 minutes.

b) Preparation of the Probe

On the basis of monkey and human SR-p70 cDNA sequences, a first sequence was produced on a fragment amplified from line AtT-20 mRNA as described in EXAMPLE II.3 and 4, with the oligomers of the following compositions:

```
                                       (SEQ ID No. 22)
sense primer:      GCC ATG CCT GTC TAC AAG (SEQ ID No. 23)
antisense primer:  ACC AGC TGG TTG ACG GAG.
```

On the basis of this sequence, an oligomeric probe specific for mouse was chosen and possesses the following composition:

(SEQ ID No. 51)
GAG CAT GTG ACC GAC ATT G.

100 ng of the probe are labelled at the 3' end with 10 units of terminal transferase (Pharmacia) and 100 µCi of [α-$^{32}$P] dCTP 3000 Ci/mmol (Amersham reference PB 10205) in 10 µl of the following buffer: 30 mM Tris-HCl pH 7.6, 140 mM cacodylic acid, 1 mM CoCl$_2$, 0.1 mM DTT for 15 minutes at 37° C. The radiolabelled nucleotides not incorporated are removed on a column of polyacrylamide P10 (Biorad, reference 1504144). The probe obtained has a specific activity of approximately 5×10$^8$ dpm/µg.

c) Prehybridization and hybridization

The membranes prepared in a) are prehybridized for 30 minutes at 42° C. in 6×SSC, 5× Denhart's, 0.1% SDS, and then hybridized for a few hours in the same buffer with the addition of the probe prepared in b) in the proportion of 10$^6$ dpm/ml.

d) Washing and exposure of the membranes

The membranes are washed twice at room temperature in 2×SSC/0.1% SDS buffer and then for one hour at 56° C. in 6×SSC/0.1% SDS. The hybridized clones are visualized with KODAK XOMAT films. A positive clone containing the mouse SR-p70 is selected and hereinafter designated as SR-p70c.

4) Sequencing of Mouse SR-p70 and Analysis of the Sequence

The sequence is obtained using the Applied Biosystem kit (reference 401628). The protein sequence deduced from mouse SR-p70c cDNA (FIG. 7) exhibits a very strong homology with the human and monkey sequences, except in the N-terminal portion which diverges strongly (see FIG. 9). Using the so-called PCR technique in a similar manner to that described in EXAMPLE II.3 and 4, a second 5' sequence (originating from the same AtT-20 library) was obtained (FIG. 8). The deduced N-terminal protein sequence (sequence designated SR-p70a) is very similar to that deduced from human and monkey SR-p70 cDNAs (SR-p70a) (FIG. 9). The line AtT-20 hence affords at least two SR-p70 transcripts. The latter 2 diverge in the N-terminal portion through different splicings.

EXAMPLE IV

1) Production of Recombinant SR-p70 Protein in *E. coli* a) Construction of the expression plasmid

This consists in placing the COOH-terminal portion of the monkey SR-p70a protein, from the valine at position 427 to the COOH-terminal histidine at position 637, in fusion with the glutathione S-transferase (GST) of the plasmid vector pGEX-4T-3 (Pharmacia reference 27-4583). For this purpose, the corresponding insert of SR-p70a (position 1434 to 2066) was amplified by PCR with 10 ng of plasmid containing monkey SR-p70a cDNA. The nucleic acid primers are of the following composition:

```
                                          (SEQ ID No. 52)
sense      TTT GGA TCC GTC AAC CAG CTG GTG GGC CAG
primer:    BamHI restriction site (SEQ ID No. 52)
antisense  AAA GTC GAC GTG GAT CTC GGC CTC C
primer:    Sal I site
```

The fragment obtained and also the vector are digested with the restriction enzymes BamHI and Sal I and cloning is carried out as described in EXAMPLE II.5. The selected clone is referred to as pG SR-p70.

b) Expression and purification of the GST-pSR-p70 fusion protein

This step was carried out using the "bulk GST purification module" kit (Pharmacia Reference 27-4570-01).

In outline, the recombinant clone was cultured at 37° C. in one liter of 2×YTA medium+100 µg/ml ampicillin. At OD 0.8, expression is induced with 0.5 mM IPTG for 2 hours at 37° C. After centrifugation, the cell pellet is taken up in cold PBS and then sonicated by ultrasound. After the addition of 1% Triton X-100, the preparation is incubated for 30 minutes with agitation at room temperature. After centrifugation at 12,000 g for 10 minutes at 4° C., the supernatant is recovered. Purification is then carried out on a glutathione-Sepharose 4B affinity chromatography column. Binding and washing are carried out in PBS buffer and elution is carried out by competition with reduced glutathione. The final concentration is brought to 300 µg/ml of fusion protein.

2) Production of SR-p70a Protein in COS-3 Cells

COS-3 cells are transfected with pSE1 plasmid DNA into which monkey SR-p70a cDNA has been cloned (EXAMPLE I.1), or with the vector pSE1 plasmid DNA as control, by the DEAE-dextran technique: the COS-3 cells are inoculated at 5×10$^5$ cells per 6 cm dish in culture medium containing 5% of foetal bovine serum (EXAMPLE I.1). After culture, the cells are rinsed with PBS. 1 ml of the following mixture is added: medium containing 6.5 µg of DNA, 250 µg/ml of DEAE-dextran and 100 µM chloroquine. The cells are incubated at 37° C. in 5% CO$_2$ for 4 to 5 hours. The medium is aspirated off, 2 ml of PBS containing 10% of DMSO are added and the cells are incubated for one minute, shaking the dishes gently. The medium is aspirated off again and the cells are rinsed twice with PBS. The cells are then incubated at 37° C. with medium containing 2% of foetal bovine serum for the period during which expression takes place, which is generally 3 days.

The SR-p70a protein is then analysed as described in EXAMPLE IV by immunoblotting.

EXAMPLE V

Preparation of Specific Antibodies

150 µg of proteins of the sample prepared according to EXAMPLE IV were used to immunize a rabbit (New Zealand male weighing 1.5 to 2 kg approximately). The immunizations were performed every 15 days according to the protocol described by Vaitukaitis, Methods in Enzymology, 1981, 73, 46. At the first injection, one volume of antigenic solution is emulsified with one volume of Freund's complete adjuvant (Sigma reference 4258). Five boosters were administered in Freund's incomplete adjuvant (Sigma reference 5506).

EXAMPLE VI

Detection of the SR-p70 Protein: Western Immunoblotting

1) Materials used for Immunoblotting a) Cell lines used for immunoblotting

The following cell lines were cultured as described in the catalogue "Catalogue of cell lines and hybridomas, 7th edition, 1992" of the ATCC (American Type Culture Collection): COS-3, CV-1 (monkey kidney cell line), HT-29, U-373MG (human glioblastoma), MCF7 (human mammary adenocarcinoma), SKNAS (human neuroblastoma cultured under the same conditions as COS-3), SK-N-MC (human neuroblastoma), IMR-32 (human neuroblastoma), CHP212 (human neuroblastoma cultured under the same conditions as CV-1), Saos-2 (osteosarcoma), SK-OV-3 (ovarian adenocarcinoma) and SW 480 (human colon adenocarcinoma).

b) COS-3 Cells Transfected by SR-p70a cDNA

COS-3 cells were transfected as described in EXAMPLE IV.2. As a control, the cells were transfected with pSE1 plasmid DNA not containing recombinant SR-p70a cDNA.

2) Preparation of Protein Samples from a Eukaryotic Cell Culture or from Transfected Cells After culture, the cells are washed with PBS and then taken up in RIPA buffer (PBS with 1% NP40, 0.5% sodium deoxycholate, 0.5% SDS) supplemented with 10 μg/ml RNAse A, 20 μg/ml DNAse 1, 2 μg/ml aprotinin, 0.5 μg/ml leupeptin, 0.7 μg/ml pepstatin and 170 μg/ml PMSF. The cells are sonicated by ultrasound at 4° C. and left for 30 minutes at 4° C. After microcentrifugation at 12,000 rpm, the supernatant is recovered. The protein concentration is measured by the Bradford method.

3) Western Blotting 5 or 50 μg of proteins (50 μg for the cell lines and 5 82 g for transfected cells) are placed in 0.2 volume of the following 6× electrophoresis buffer: 0.35 mM Tris-HCl pH 6.8, 10.3% SDS, 36% glycerol, 0.6 mM DTT, 0.012% bromophenol blue. The samples are applied and run in a 10% SDS-PAGE gel (30:0.8 Bis) and then electrotransferred onto a nitrocellulose membrane.

4) Visualization with the Antibody

The membrane is incubated for 30 minutes in TBST blocking buffer (10 mM Tris-HCl pH 8, 150 mM NaCl, 0.2% Tween 20) with the addition of 5% of milk (GIBCO—SKIM MILK) at room temperature. The membrane is brought into contact successively with the anti-SR-p70 (αSR-p70) antibody in the same buffer for 16 hours at 4° C., washed 3 times for 10 minutes with TBST and then incubated for one hour at 37° C. with a second, anti-rabbit immunoglobulin antibody coupled to peroxidase (SIGMA A055). After three washes of 15 minutes, the visualization is performed using the ECL kit (Amersham RPN2106) by chemiluminescence.

In parallel, the same samples were subjected to visualization with an anti-p53 (αp53) antibody (Sigma BP5312) followed by a second, anti-mouse immunoglobulin antibody.

5) Figures and Results

FIG. 10: Immunoblot of the SR-p70 Protein

FIG. 10a: Detection of the Recombinant SR-p70 Protein
  columns 1 and 3: COS-3 transfected by the vector pSE1.
  columns 2 and 4: COS-3 transfected by plasmid pSE1 containing SR-p70a cDNA.
  columns 1 and 2: visualization with the anti-SR-p70 (αSR-p70) antibody.
  columns 3 and 4: visualization with the anti-p53 (αp53) antibody.

FIG. 10b: Detection of the Endogenous SR-p70 Protein
  columns 1: COS-3; 2: CV-1; 3: HT-29; 4: U-373 MG; 5: MCF7; 6: SKNAS; 7: SK-N-MC; 8: IMR-32; 9: CHP212; 10: Saos-2; 11: SK-OV-3 and 12: SW480.

A: Visualization with the αSR-p70 Antibody

B: Visualization with the αp53 Antibody.

The αSR-p70 antibody specifically recognizes the recombinant proteins (FIG. 10a) and endogenous proteins (FIG. 10b) and does not cross with p53. The analysis of human or monkey cell lines shows the SR-p70 protein, like p53, is generally weakly detectable. In contrast, when an accumulation of p53 exists, SR-p70 becomes, for its part also, more readily detectable (FIG. 10b). A study by RT-PCR of the distribution of SR-p70 transcripts shows that the gene is expressed in all the cell types tested.

EXAMPLE VII

Cloning of the SR-p70 Gene and Chromosomal Localization

1) Cloning of SR-p70 Gene

The library used is a cosmid library prepared with purified human genomic DNA from placenta and marketed by Stratagene (reference 95 1202).

Screening of the gene is carried out as described in the EXAMPLE III.3, with an SR-p70 DNA fragment labelled with $^{32}P$ with the BRL "Random Primers DNA Labelling Systems" kit (reference 18187-013). The hybridization and washing buffers are treated by adding 50% of formaldehyde. The last wash is carried out in 0.1×SSC/0.1% SDS at 60° C. In a similar manner, the SR-p70 gene was isolated from a library prepared with C57 black mouse genomic DNA.

An analysis and a partial sequencing of the clones demonstrate the presence of 14 exons with a structure close to that of the p53 gene, in particular in the central portion where the size and positioning of the exons are highly conserved (FIG. 12). This structure was partially defined in mouse and in man.

As an example, the human genomic sequences of the 3' region of intron 1, of exon 2, of intron 3 and of the 5' region of exon 3 are presented in FIG. 13.

2) Chromosomal Localization of the SR-p70 Gene in Man

This was carried out with human SR-70 gene DNA using the technique described by R. Slim et al., Hum. Genet., 1991, 88, 21-26. Fifty mitoses were analysed, more than 80% of which had double spots localized at 1p36 on both chromosomes and more especially at 1p36.2-1p36.3 (FIG. 11). The identification of chromosome 1 and its orientation are based on the heterochromatin of the secondary constriction. The pictures were produced on a Zeiss Axiophot microscope, taken with a LHESA cooled CCD camera and treated with Optilab.

EXAMPLE VIII

A) Demonstration of an mRNA Coding for a Deduced Human SR-p70 Protein Possessing Both a Shorter N-terminal End and a Divergence.

1) Culturing of IMR-32 (Human Neuroblastoma) Cells

The cells were cultured as described in the catalogue "Catalogue of cell lines and hybridomas, 7th edition, 1992" of the ATCC (American Type Culture Collection).

2) Preparation of the CDNA

The RNA is prepared as described in Example I.2.a. The cDNA is prepared in a manner similar to that described in Example I.3, with 5 µg total RNA in a final volume of 20 µl using a poly(T)$_{12}$ primer and with cold nucleotides. The reaction is not interrupted with EDTA.

3) Specific Amplification of SR-p70 CDNA by the So-Called PCR Technique

The polymerization is carried out with 2 µl of cDNA in 50 µl final with the buffer of the following composition: 50 mM Tris-HCl pH 9.2, 16 mM (NH$_4$)$_2$SO$_4$, 1.75 mM MgCl$_2$, in the presence of 10% DMSO, 0.4 mM NTP, 100 ng of each of the two nucleic acid primers and 3.5 units of the mixture of TAQ and PWO polymerases (Boehringer Mannheim, ref. 1681 842).

The primer pair is of the following composition:

```
sense primer:                         (SEQ ID No. 26)
AGGCCGGCGTGGGGAAG (position 16 to 32, FIG. 6)

antisense primer:                     (SEQ ID No. 27)
CTTGGCGATCTGGCAGTAG (position 503 to 485, FIG. 6).
```

The reaction is carried out for 30 cycles at 95° C./30 seconds, 58° C./1 minute and 68° C./2 minutes 30 seconds, followed by a final cycle of 68° C./10 minutes.

The PCR product is subjected to electrophoresis on a 1% agarose gel (TAE buffer). After ethidium bromide staining, two major bands are revealed: a band approximately 490 bp in size (expected size (see FIG. 6)) and an additional band approximately 700 bp in size. The latter is extracted from the gel using the "Geneclean" kit (Bio 101, ref 1001 400). After a desalting on a column of polyacrylamide P10 (Biorad, ref 15011050), the fragment is subjected to a further PCR amplification for 10 cycles as described above.

4) Determination of the Sequence of the Amplified Product

In a first step, the PCR product is removed from the oligo-nucleotides on a column of Sephacryl S-400 (Pharmacia 17-0609-01) and then desalted on a column of P10. The sequencing reaction is carried out using the Applied Biosystems kit (ref. 401 628) (373 DNA sequencer) with the antisense primer.

The sequence obtained is identical to the SR-p70 cDNA sequence (Example II.4) with an insertion of 198 bp between positions 217 and 218 (FIG. 14). The deduced N-terminal protein sequence (sequence designated SR-p70d) is 49 amino acids shorter, with a divergence of the first 13 amino acids (sequence ID No. 13). There is hence coexistence of at least two different SR-p70 transcripts as already described for the mouse AtT-20 line.

B) Cloning of Human SR-p70 and Demonstration of an mRNA Coding for a Deduced Human SR-p70 Protein Possessing the Same N-terminal End as SR-p70d and a Divergence in the C-terminal Portion 1) Specific Amplification of SR-p70 cDNA by the So-Called PCR Technique The amplification was carried out as described in EXAMPLE VIII.A from purified RNA of IMR-32 cells with the primer pair of the following composition:

```
sense primer:                         (SEQ ID No. 28)
GCG GCC ACG ACC GTG AC (position 160 to 176,
sequence ID No. 11)

antisense primer:                     (SEQ ID No. 29)
GGC AGC TTG GGT CTC TGG (position 1993 to 1976,
FIG. 6).
```

After removal of the excess primers on an S400 column and desalting on a P10 column, 1 µl of the sample is subjected again to a PCR with the primer pair of the following composition:

```
                                      (SEQ ID No. 54)
sense primer:   TAT CTC GAG CTG TAC GTC GGT GAC CCC
                    XhoI                  (position
                263 to 280, sequence ID No. 11)

(SEQ ID No. 55)
antisense       ATA TCT AGA TCA GTG GAT CTC GGC CTC
primer:             XbaI                  (position
                1943 to 1926, FIG. 6).
```

2) Cloning of the Amplified Product into Plasmid pCDNA3

The PCR product obtained in 1) is desalted on a P10 column, digested with the restriction enzymes XhoI and XbaI and then cloned into plasmid pCDNA3 as described in EXAMPLE II.5. Two recombinant clones are sequenced using the Applied Biosystems kit with the oligonu-cleotides specific for SR-p70 cDNA.

The first sequence obtained corresponds to the complete sequence of the mRNA coding for SR-p70 described in EXAMPLE VIII.a. The deduced protein contains 587 amino acids (sequence ID No. 13 and FIG. 16).

The second sequence obtained is identical to the SR-p70d cDNA sequence described above, but with two deletions, of 149 bp and of 94 bp between positions 1049 and 1050 on the one hand, and between positions 1188 and 1189 on the other hand (sequence ID No. 14 and FIG. 15). The protein sequence deduced from this second sequence reveals a protein having an N-terminal portion 49 amino acids shorter, with a divergence in the first 13 amino acids as well as a divergence of protein sequence between amino acids 350 and 397 (sequence ID No. 15 and FIG. 16) (sequence designated SR-p70e). The deduced protein contains 506 amino acids.

C) Demonstration of an mRNA Coding for a Deduced Human SR-p70 Protein Possessing a Shorter N-terminal End 1) Culturing of SK-N-SH (Human Neuroblastoma) Cells The cells are cultivated as described in the "Catalogue of cell lines and hybridomas, 7th edition, 1992" of the ATCC (American Type Culture Collection).

2) Preparation of the CDNA and Amplification of SR-p70 cDNA by the So-Called PCR Technique These steps are carried out as described in EXAMPLE VIII.A with the primer pair of the following composition:

```
                                      (SEQ ID No. 32)
sense primer: AGG GGA CGC AGC GAA ACC (position 128
              to 145, FIG. 17)

(SEQ ID No. 29)
antisense     GGC AGC TTG GGT CTC TGG (position
primer:       1993 to 1976, FIG. 6).
```

The sequencing is carried out with the Applied Biosystem kit with primers specific for SR-p70 cDNA, and reveals two cDNAs:

a first cDNA corresponding to the mRNA coding for SR-p70a a second cDNA having a deletion of 98 bp between positions 24 and 25 (sequence ID No. 16 and FIG. 15).

This deletion comprises the translation initiation ATG of SR-p70a. The protein deduced (designated SR-p70f) from this second cDNA possesses a translation initiation ATG downstream corresponding to an internal ATG of SR-p70a. The deduced protein hence contains 588 amino acids (sequence ID No. 17 and FIG. 16) and is truncated with respect to the 48 N-terminal amino acids of SR-p70a.

D) Demonstration of an mRNA Coding for Human SR-p70b

1) Culturing of K562 Cells

The cells are cultured as described in the "Catalogue of cell lines and hybridomas, 7th edition, 1992" of ATCC (American Type Culture Collection).

2) Preparation of the cDNA, Amplification of SR-p70 cDNA by the So-Called PCR Technique and Sequencing These steps are carried out as described in EXAMPLE VIII.C.

The sequencing reveals two cDNAs:

A first cDNA corresponding to the mRNA coding for SR-p70a, and a second cDNA having a deletion of 94 bp between positions 1516 and 1517 (sequence ID No. 18 and FIG. 15). The deduced protein (designated SR-p70b) contains 199 amino acids and possesses a C-terminal sequence truncated by 137 amino acids relative to SR-p70a, with the last 4 amino acids divergent (sequence ID No. 19 and FIG. 21).

This cDNA is similar to the one described in EXAMPLE I relating to monkey SR-p70b.

The molecules described in this example (EXAMPLE VIII.A, B, C and D) reveal SR-p70 variants which are the outcome of differential splicings of the primary mRNA, transcribed by the SR-p70 gene.

The SR-p70a is encoded by an mRNA composed of 14 exons (see EXAMPLE VII). This is the reference protein. SR-p70b is the outcome of an insertion between exons 3 and 4 and of the absence of exons 11 and 13. SR-p70f is the outcome of the absence of exon 2. This example describes the existance of SR-p70 variants non-exhaustively, with a strong probability of existence of other variants. Similarly, the existence of these variants described in this example, as well as SR-p70a, is not limited to the lines in which they have been demonstrated. In effect, studies performed by RT-PCR showed that these variants are to be found in the various lines studied.

Furthermore, the initiation methionine of SR-p70f corresponds to an internal methionine of SR-p70a, suggesting the possibility of initiation downstream on the mRNA coding for SR-p70a.

EXAMPLE IX

Obtaining a 5' Sequence of Human SR-p70a mRNA

1) Amplification of the 5' End of SR-p70 CDNA by PCR

The cell culturing and the preparations of total RNA and of cDNA are carried out as described in EXAMPLE VIII.1 and 2. The RNA template is hydrolysed by incubation for 5 minutes at 65° C. after the addition of 4 µl of 500 mM EDTA and 4 µl of 2 N NaOH. The sample is then desalted on a P10 column. The cDNA is elongated at the 3' end with a dG tail as described in EXAMPLE I.3.d, in a final volume of 40 µl. After the addition of 4 µl of 500 mM EDTA and 4 µl of 2 N NaOH, the cDNA is incubated at 65° C. for 3 minutes and then desalted on a P10 column. PCR amplification is carried out as described in EXAMPLE VIII.3 with 8 µl of cDNA and for 30 cycles with the primer pair of the following composition:

```
                                            (SEQ ID No. 41)
sense primer:    C C C C C C C C C C C C C C N (where
                 N equals G, A or T)

(SEQ ID No. 33)
antisense        CCATCAGCTCCAGGCTCTC (position 1167
primer:          to 1149, FIG. 6).
```

After removal of the excess primers on an S-400 column and desalting on a P10 column, 1 µl of the sample is subjected again to a PCR with the pair of the following composition.

```
                                            (SEQ ID No. 41)
sense primer:    C C C C C C C C C C C C C C N (SEQ ID No. 34)
antisense primer: CCAGGACAGGCGCAGATG (position 928
                  to 911, FIG. 6).
```

The sample, passed again through an S-400 column and a P10 column, is subjected to a third amplification for 20 cycles with the following pair:

```
sense primer:    C C C C C C C C C C C C C C N antisense        CTTGGCGATCTGGCAGTAG (position 503
primer:          to 485, FIG. 6).
```

2) Determination of the SR-p70 CDNA 5' Sequence

The sequence is produced as described in EXAMPLE VIII.4.

Figure 17:
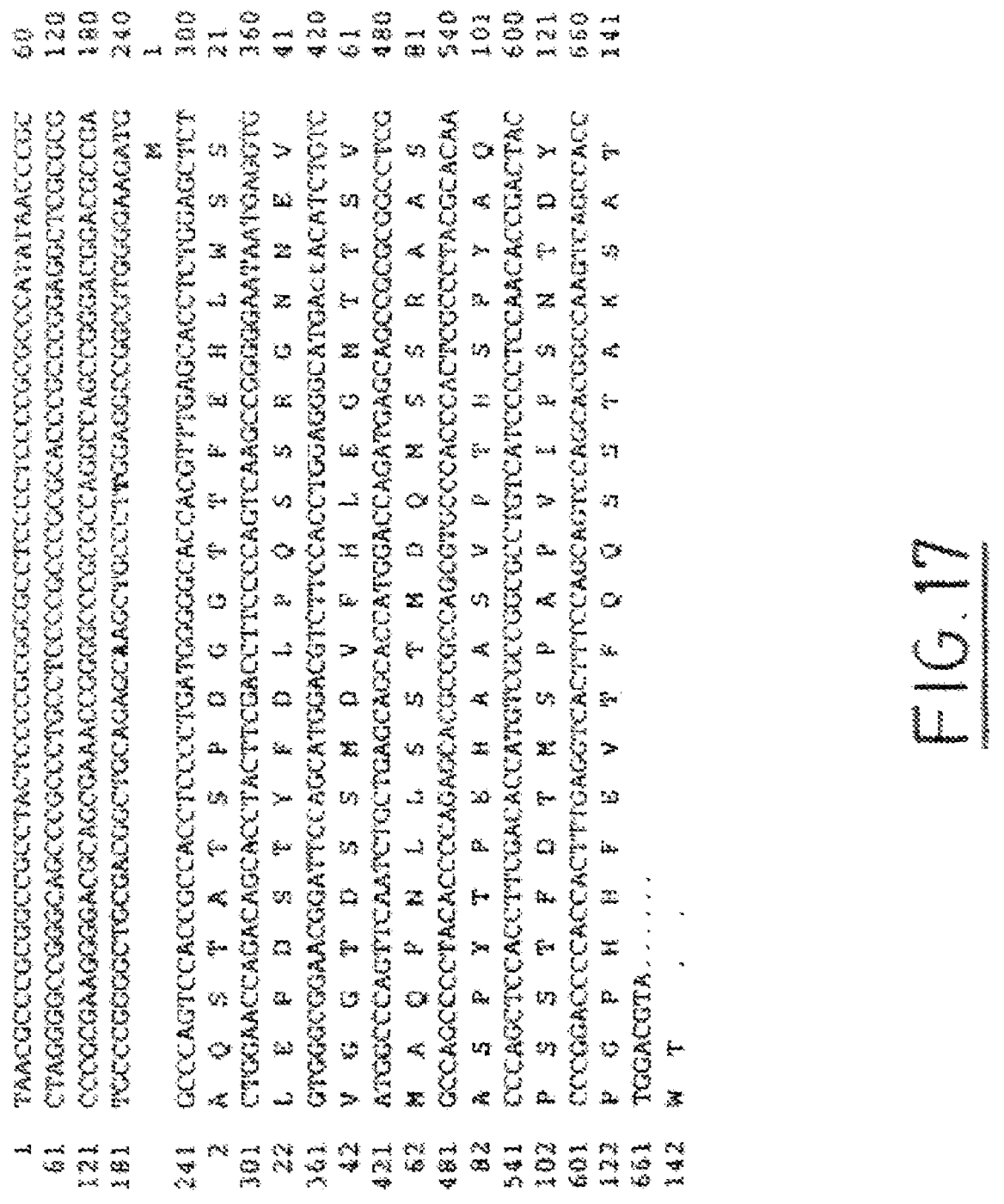

This sequence reveals a non-coding 5' region of at least 237 bases upstream of the initiation ATG of SR-p70a (FIG. 17). By comparison of this sequence (obtained from the line IMR-32) with the one obtained from the line HT-29 in particular (FIG. 6), two point differences (FIG. 17: see bold characters) are revealed (G→A and C→T), positioned, respectively, at −20 and −30 from the initiation ATG of SR-p70a (FIGS. 6 and 17). This variability is located in exon 2 (FIG. 13). It is not ruled out that this variability is also to be found within a coding frame as the outcome of an alternative splicing as described in EXAMPLES III in mouse and VIII in man, or alternatively as the outcome of a translation initiation on a CTG (as has been demonstrated for FGFb (Proc. Natl. Acad. Sci USA, 1989, 86, 1836-1840)).

Similarly, it is not ruled out that this variability has a repercussion on the translation of SR-p70 or on the splicing of the primary RNA.

At all events, this variability, probably of allelic origin, may serve as a marker, either at genomic level (see EXAMPLE XI) or at mRNA level (see EXAMPLE X).

EXAMPLE X

1) Analysis by PCR of the Transcriptional Expression of SR-p70a in Cell Samples (RT-PCR)

Cell culturing (SK-N-AS, SK-N-MC, HT-29, U-373MG, SW480, IMR-32, CHP212) is carried out as described in Example VI.1.a (referred to the catalogue "Catalogue of cell lines and hybridomas, 7th edition 1992" of the ATCC).

The preparation of the cDNA and the PCR amplification are carried out as described in EXAMPLE VIII.2 and 3. The primer pair used is of the following composition:

```
sense primer:      AGGGGACGCAGCGAAACC  (SEQ ID No. 32)
                   (position 128 to
                   145, FIG. 17)

antisense          GGCAGCTTGGGTCTCTGG  (SEQ ID No. 29)
primer:            (position 1993
                   to 1976, FIG. 6).
```

Figure 18:
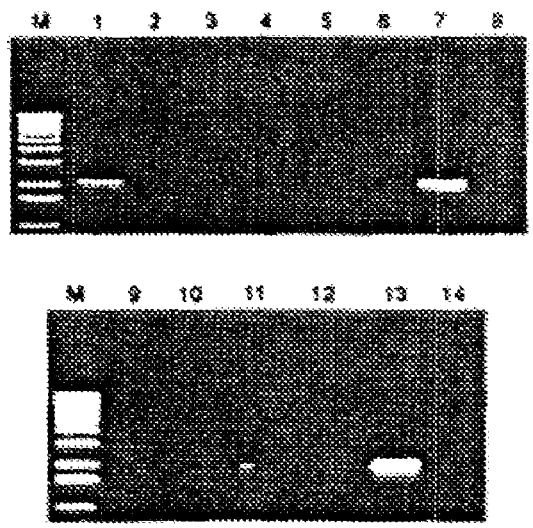

The samples are analysed by electrophoresis on a 1% agarose gel and visualization with ethidium bromide (FIG. 18).

The size of the band obtained in the samples corresponds to the expected size (approximately 2 kb, FIGS. 6 and 17). The intensity of the bands obtained is reproducible. A reamplification of 1 μl of the sample under the same conditions for 20 cycles reveals a band in each of the samples.

2) Determination of the Sequence of the Amplified Products

After passage of the samples through S-400 and P10 columns, sequencing is carried out on an Applied Biosystems sequencer 373 with the reference kit 401 628. The primers used are, inter alia, the following:

|  | position | Figure |
|---|---|---|
| AGGGGACGCAGCGAAACC (SEQ ID No. 32) | 128 to 145 | 22 |
| CTTGGCGATCTGGCAGTAG (SEQ ID No. 27) | 503 to 485 | 6 |
| GATGAGGTGGCTGGCTGGA (SEQ ID No. 35) | 677 to 659 | 6 |
| CCATCAGCTCCAGGCTCTC (SEQ ID No. 33) | 1167 to 1149 | 6 |
| TGGTCAGGTTCTGCAGGTG (SEQ ID No. 36) | 1605 to 1587 | 6 |
| GGCAGCTTGGGTCTCTGG (SEQ ID No. 29) | 1993 to 1976 | 6 |

No protein difference in the SR-p70a was detected. However, sequences obtained reveal a double variability at positions −20 and −30 upstream of the initiation ATG of SR-p70a (FIGS. 6 and 17). This variability, probably of allelic origin, enables two classes of transcripts to be defined: a first class possessing a G at position −30 and a C at position −20 (class $G^{-30}/C^{-20}$) and a second class possessing a difference at two positions: an A at −30 and a T at −20 (class $A^{-30}/T^{-20}$).

First class: SK-N-AS, SK-N-MC, HT-29, U-373MG, SW480.
Second class: IMR-32, CHP212.

EXAMPLE XI

Analytical Method of Determination of the Allelic Distribution of the SR-p70 Gene in a Population of 10 Persons This allelic distribution is based on the allelic variability demonstrated in EXAMPLES IX and X:

$G^{-30}/C^{-20}$ allele possessing, respectively, a G and a C at positions −30 and −20 upstream of the initiation ATG of SR-p70a.

$A^{-30}/T^{-20}$ allele possessing, respectively, an A and a T at the same positions.

This variability may be demonstrated by the use of restriction enzymes that differentiate the two alleles (FIG. 13). As an example:

Enzyme BpI I having a cleavage site only on the $G^{-30}/C^{-20}$ allele in the zone of interest (this site encompasses both variable positions).

Enzyme StyI having a cleavage site only on the $A^{-30}/T^{-20}$ allele in the zone of interest.

1) Genomic Amplification of Exon 2 by PCR

The polymerization reaction is carried out with 500 ng of purified genomic DNA, in 50 μl final with the conditions described in Example VIII.3.

The primer pair is of the following position:

```
                                      (SEQ ID No. 37)
Sense primer: CACCTACTCCAGGGATGC (position 1 to 18,
                                   FIG. 13)

(SEQ ID No. 38)
Antisense     AGGAAAATAGAAGCGTCAGTC (position 833
primer:                              to 813, FIG. 13).
```

The Reaction is Carried out for 30 Cycles as Described in EXAMPLE VIII.3.

After removal of the excess primer on an S-400 column and desalting on a P10 column, 1 μl of the sample is amplified again for 25 cycles under the same conditions with the following primer pair:

```
                                      (SEQ ID No. 39)
Sense primer: CAGGCCCACTTGCCTGCC (position 25 to
                                   32, FIG. 13)

(SEQ ID No. 40)
Antisense     CTGTCCCCAAGCTGATGAG (position 506 to
primer:                            488, FIG. 13).
```

The amplified products are subjected to electrophoresis on a 1% agarose gel (FIG. 19-A).

2) Digestion with the Restriction Enzyme StyI

The samples are desalted beforehand on a P10 column and then digested with the restriction enzyme StyI (BRL 15442-015) in the buffer of the following composition: 50 mM Tris-HCl pH 8, 100 mM NaCl, 10 mM $MgCl_2$, at 37° C. for 30 min. The digestion products are analysed by electrophoresis on a 1% agarose gel (TAE buffer). Visualization is carried out by ethidium bromide staining (FIG. 19-B).

A band of 482 base pairs characterizes the $G^{-30}/C^{-20}$ allele (FIGS. 13 and 19). The presence of a band of 376 base pairs and a band of 106 base pairs characterize the $A^{-30}/T^{-20}$ allele (allele possessing a StyI cleavage site).

On the population of 10 persons, 2 persons exhibit the $G^{-30}/C^{-20}$ and $A^{-30}/T^{-20}$ alleles, the other 8 persons being homozygous with the $G^{-30}/C^{-20}$ allele. The study of a fresh population of 9 persons demonstrated 3 heterozygous persons exhibiting the $G^{-30}/C^{-20}$ and $A^{-30}/T^{-20}$ alleles, the other 6 persons being homozygous for the $G^{-30}/C^{-20}$ allele.

EXAMPLE XII

Test of Reversion of Transformation of the Line SK-N-AS by Transfection with SR-p70 cDNA The expression vector used is described in EXAMPLE II.5 and shown diagrammatically in FIG. 15. The method used is the so-called calcium phosphate method described by Graham et al. (Virology 1973, 54, 2, 536-539). The line is inoculated in the proportion of $5 \times 10^5$ cells per dish 6 cm in diameter in 5 ml of the medium described in Example I.1. The cells are cultured at 37° C. and with 5% $CO_2$ overnight. The transfection medium is prepared in the following manner: the following mixture is prepared by adding, in order, 1 ml of HEBS buffer (8 mg/ml NaCl, 370 µg/ml KCl, 125 µg/ml Na$_2$HPO$_4$.2H$_2$O, 1 mg/ml dextrose, 5 mg/ml Hepes pH 7.05), 10 µg of the plasmid to be transfected and 50 µl of 2.5 M CaCl$_2$ added dropwise. The transfection medium is left for 30 min at room temperature and then added dropwise to the medium contained in the culture dish. The cells are incubated for 5 to 6 hours at 37° C./5% CO$_2$. After the medium is aspirated off, 5 ml of fresh medium containing 2% of foetal bovine serum are added. After 48 hours at 37° C./5% CO$_2$, the cells are rinsed with PBS, detached by trypsinization, diluted in 10 ml of culture medium (5% foetal bovine serum) and plated out in a dish 10 cm in diameter (the dilution may be adjusted in accordance with the efficiency of transfection). After a further incubation for 10 hours (the time for the cells to adhere), the cells are subjected to selection by adding G418 at a final concentration of 600 µg/ml Geneticin equivalent for 15 to 21 days (the medium is changed every day). The clones obtained are then rinsed with PBS, fixed in 70% ethanol, dried, stained with 1% crystal violet and then counted.

Four plasmid transfections were carried out in duplicate:
plasmid pCDNA3 without insert
plasmid pCDNA3/SR-p70 containing human SR-p70a cDNA
plasmid pCDNA3/SR-p70 Mut containing SR-p70a cDNA possessing a mutation at position 293 AA (R→H) which is analogous to the mutation 273 (R→H) in the DNA-binding domain of p53
control without plasmid.
The result is expressed as the number of clones per dish.

|  | Experiment 1 | Experiment 2 | Mean |
|---|---|---|---|
| pCDNA3 | 172 | 353 | 262 |
| pCDNA3/SR-p70 | 13 | 8 | 10 |
| pCDNA3/SR-p70 Mut | 92 | 87 | 89 |
| Absence of plasmid | 1 | 3 | 2 |

The number of clones obtained by transfection with plasmid pCDNA3/SR-p70 is 254-fold less than the number of clones obtained with the control pCDNA3 and 9-fold less than the number of clones obtained with pCDNA3/SR-p70 Mut, indicating a mortality or an arrest of cell division of the cells transfected with SR-p70 CDNA. This result is not the consequence of a toxicity in view of the clones obtained with the mutated SR-p70 cDNA, but probably of an apoptosis as has been demonstrated for the p53 protein (Koshland et al., Sciences, 1993, 262, 1953-1981).

EXAMPLE XIII

Biological Role of the SR-p70 Protein

The structural homology between the DNA-binding domain of p53 and the central region of the SR-p70 protein enables it to be inferred that SR-p70 is a transcription factor (see FIGS. 1 and 2). In effect, p53 (393 amino acids) consists of several functional domains. The N-terminal region (1-91 amino acids) is involved in the activation of transcription, and contains sites for interaction with different cellular and viral proteins. The central portion (amino acids 92 to 292) permits binding to the specific DNA sequences located in the promoter regions of certain genes (the majority of point mutations that inactivate p53 are localized in this region), and also possesses numerous sites for interaction with viral proteins which inhibit its activity. Finally, the last 100 amino acids of p53 are responsible for its oligomerization as well as for the regulation of the latter (Hainaut P., Current Opinion in Oncology, 1995, 7, 76-82; Prokocimer M., Blood, 1994, 84 No. 8, 2391-2411).

The sequence homology between p53 and SR-p70 is significant, in particular as regards the amino acids involved directly in the interaction with DNA, suggesting that SR-p70 binds to the p53 sites on DNA. These amino acids correspond very exactly to what are referred to as the "hot spots", amino acids frequently mutated in human tumours (SWISS PROT: SW: P53_human and Prokocimer M., Blood, 1994, 84 No. 8, 2391-2411). From this homology, it may be deduced that the SR-p70 protein exerts a control over the activity of the genes regulated by p53, either independently of the latter or by forming heterooligomers with it.

Consequently, like p53, the products of the SR-p70 gene must be involved in the control and regulation of the cell cycle, causing the cycle to stop (momentarily or permanently), and the implementation of programmes such as DNA repair, differentiation or cell death. The likelihood of the existence of "p53-like" activities had been strongly felt with the demonstration in p534$^{-/-}$ mice of activities of DNA repair and cell death in response to ionizing radiations (Strasser et al., Cell, 1994, 79, 329-339). The authors of the present invention have localized the human SR-p70 gene in the telomeric region of the short arm of chromosome 1, precisely at 1p36.2-36.3, the smallest deleted region (SRO) common to a majority of neuroblastomas and of other types of tumours (melanomas and sarcomas) (White et al., PNAS, 1995, 92, 5520-5524). This region of loss of heterozygosity (LOH) defines the locus of a tumour-suppressing gene whose loss of activity is considered to be the cause of tumour formation. It is important to recall that this region is also subject to "maternal imprinting"; the maternal allele is preferentially lost in neuroblastomas having the 1p36 deletion (without amplification of N-Myc) (Caron et al., Hum. Mol. Gen., 1995, 4, 535-539). The wide-type SR-p70 gene introduced into neuroblastoma cells and expressed therein permits the reversion of their transformation. The loss of this anti-oncogenic activity is hence associated with the development of the tumour. The 1p36 region possesses a syngeneic homology with the distal segment of the mouse chromosome 4. In this region, the curly tail (Ct) gene (Beier et al., Mammalian Genome, 1995, 6, 269-272) involved in congenital malformations of the neural tube (NTM: spina bifida, anencephaly, etc). The ct mouse is the best animal model for studying these malformations. It is accepted that these malformations result from abnormalities of cell proliferation. Bearing in mind the nature of the SR-p70 gene and its chromosomal localization, one of the hypotheses is that SR-p70 could be the human homologue of ct and that, on this basis, the detection of early mutations and chromosomal abnormalities affecting this gene should permit, for example, as an application, the identification of persons at risk (0.5-1% of newborn babies affected by NTM) and the implementation of preventive treatments (Neumann et al., Nature Genetics, 1994, 6, 357-362; Di Vinci et al., Int. J. Cancer, 1994, 59, 422-426; Moll et al., PNAS, 1995, 92, 4407-4411; Chen et al., Development, 1995, 121, 681-691).

EXAMPLE XIV

Allelic Study of the SR-p70 Gene

The GC and AT alleles are readily identified by StyI restriction of the PCR products of exon 2 (see Example XI). Hence it was possible to determine in this way, in GC/AT heterozygous individuals bearing neuroblastoma tumours, the lost SR-p70 allele (GC or AT), in spite of the presence-of contaminating healthy tissue.

Surprisingly, when the same analysis is carried out on the RNA, a single allele is demonstrated independently of the presence or otherwise of a deletion and, still more surprisingly, in spite of the presence of healthy tissue. This suggests that the imprint (differential expression of the two alleles) would also exist in the contaminating tissue.

In order to verify this, the same analysis was repeated on the RNA originating from blood cells of healthy GC/AT heterozygous individuals. Only one of the two types of transcript was detected also in these cells. This result confirms the observation made on the tumour samples regarding the existence of a generalized genetic imprint for the SR-p70 gene.

The implications of this discovery are important, since it enables it to be postulated that a single sporadic mutation inactivating the active SR-p70 allele will give rise to a loss of activity, this potentially occurring in all the tissues.

The absence of precise data on the biological function of SR-p70 does not enable the consequences of this loss of SR-p70 activity for the cell to be measured. Nevertheless, its strong homology with the p53 tumour-suppressing protein, as well as the demonstration that SR-p70 is a transcription factor capable of utilizing the P21$^{waf}$ promoter, suggests a role of this protein in the control of the cell cycle and in differentiation.

Knudson and Meadows, 1980 (New Eng. J. Med. 302: 1254-56), consider the IV-S neuroblastomas to be a collection of non-malignant cells from the neural crest carrying a mutation which interferes with their normal differentiation.

It is conceivable that the loss of SR-p70 activity, like the loss of p53 control over the cell cycle, favours the appearance of cellular abnormalities such as aneuploidy, amplification (described in the case of neuroblastomas) and other genetic reorganizations capable of causing cell transformation (Livingstone et al., 1992, Cell 71:923-25; Yin et al. 1992, Cell 72:937-48; Cross et al. 1995, Science 267:1353-56; Fukasawa et al. 1996, Science 271:1744-47). Neuroblastomas might hence arise originally from a temporary or permanent loss of activity of SR-p70, thereby favouring the occurrence of oncogenic events and hence tumour progression.

In the case of the 1p36 constitutional deletion described by Biegel et al., 1993 (Am. J. Hum. Genet. 52:176-82), IV-S neuroblastoma does indeed occur and the gene affected is NBS-1 (SR-p70).

In conclusion, what is described for neuroblastomas might also apply to other types of tumours, in particular those associated with reorganization of the end of the short arm of chromosome 1 (Report 2 international workshop on human chr 1 mapping 1995, Cytogenetics and Cell Genet. 72:113-154). From a therapeutic standpoint, the involvement of SR-p70 in the occurrence of tumours should lead to the avoidance of the use of mutagenic agents in chemotherapy, bearing in mind the risks of cell transformation by these products, and to the use, in preference to these products, of non-mutagenic substances which stimulate differentiation.

Moreover, the frequency of occurrence of the GC and AT alleles is as follows: in the population, Frequency(AT)=0.15, and on a sample of 25 (neuroblastoma) patients, F(AT)=0.30. These statistics indicate that the AT allele could be a predisposing factor.

The invention claimed is:

1. A purified polypeptide consisting essentially of amino acid sequence SEQ ID NO: 6.

2. A purified DNA binding domain polypeptide, comprising the amino acid sequence from residue 111 to residue 309 of SEQ ID NO: 6.

3. The polypeptide according to claim 2, which is produced from an alternative splicing of messenger RNA of a gene coding for said polypeptide.

4. The polypeptide according to claim 2 that is a recombinant polypeptide produced in the form of a fusion protein.

5. A composition comprising SEQ ID NO: 6 and a pharmaceutically acceptable vehicle.

6. A purified polypeptide comprising amino acid sequence SEQ ID NO: 6.

* * * * *

SEQUENCE LISTING

```
<160> NUMBER OF SEQ ID NOS: 55

<210> SEQ ID NO 1
<211> LENGTH: 2874
<212> TYPE: DNA
<213> ORGANISM: Cebus apella
<220> FEATURE:
<221> NAME/KEY: CDS
<222> LOCATION: 156..2066

<400> SEQUENCE: 1
tgcctccccg cccgcgcacc cgccccgagg cctgtgctcc tgcgaagggg acgcagcgaa      60
gccggggccc gcgccaggcc ggccgggacg gacgccgatg cccggagctg cgacggctgc     120
agagcgagct gccctcggag gccggtgtga ggaag atg gcc cag tcc acc acc        173
                                    Met Ala Gln Ser Thr Thr
                                     1               5 acc tcc ccc gat ggg ggc acc acg ttt gag cac ctc tgg agc tct ctg       221
Thr Ser Pro Asp Gly Gly Thr Thr Phe Glu His Leu Trp Ser Ser Leu
             10                  15                  20 gaa cca gac agc acc tac ttc gac ctt ccc cag tca agc cgg ggg aat       269
Glu Pro Asp Ser Thr Tyr Phe Asp Leu Pro Gln Ser Ser Arg Gly Asn
         25                  30                  35 aat gag gtg gtg ggt ggc acg gat tcc agc atg gac gtc ttc cac cta       317
Asn Glu Val Val Gly Gly Thr Asp Ser Ser Met Asp Val Phe His Leu
     40                  45                  50 gag ggc atg acc aca tct gtc atg gcc cag ttc aat ttg ctg agc agc       365
Glu Gly Met Thr Thr Ser Val Met Ala Gln Phe Asn Leu Leu Ser Ser
 55                  60                  65                  70
```

```
                                                 -continued
acc atg gac cag atg agc agc cgc gct gcc tcg gcc agc ccg tac acc     413
Thr Met Asp Gln Met Ser Ser Arg Ala Ala Ser Ala Ser Pro Tyr Thr
            75                  80                  85 ccg gag cac gcc gcc agc gtg ccc acc cat tca ccc tac gca cag ccc     461
Pro Glu His Ala Ala Ser Val Pro Thr His Ser Pro Tyr Ala Gln Pro
        90                  95                 100 agc tcc acc ttc gac acc atg tcg ccc gcg cct gtc atc ccc tcc aac     509
Ser Ser Thr Phe Asp Thr Met Ser Pro Ala Pro Val Ile Pro Ser Asn
    105                 110                 115 acc gac tat ccc gga ccc cac cac ttc gag gtc act ttc cag cag tcc     557
Thr Asp Tyr Pro Gly Pro His His Phe Glu Val Thr Phe Gln Gln Ser
120                 125                 130 agc acg gcc aag tca gcc acc tgg acg tac tcc cca ctc ttg aag aaa     605
Ser Thr Ala Lys Ser Ala Thr Trp Thr Tyr Ser Pro Leu Leu Lys Lys
135                 140                 145                 150 ctc tac tgc cag atc gcc aag aca tgc ccc atc cag atc aag gtg tcc     653
Leu Tyr Cys Gln Ile Ala Lys Thr Cys Pro Ile Gln Ile Lys Val Ser
                155                 160                 165 gcc cca ccg ccc ccg ggc acc gcc atc cgg gcc atg cct gtc tac aag     701
Ala Pro Pro Pro Pro Gly Thr Ala Ile Arg Ala Met Pro Val Tyr Lys
            170                 175                 180 aag gcg gag cac gtg acc gac atc gtg aag cgc tgc ccc aac cac gag     749
Lys Ala Glu His Val Thr Asp Ile Val Lys Arg Cys Pro Asn His Glu
        185                 190                 195 ctc ggg agg gac ttc aac gaa gga cag tct gcc cca gcc agc cac ctc     797
Leu Gly Arg Asp Phe Asn Glu Gly Gln Ser Ala Pro Ala Ser His Leu
    200                 205                 210 atc cgt gtg gaa ggc aat aat ctc tcg cag tat gtg gac gac cct gtc     845
Ile Arg Val Glu Gly Asn Asn Leu Ser Gln Tyr Val Asp Asp Pro Val
215                 220                 225                 230 acc ggc agg cag agc gtc gtg gtg ccc tat gag cca cca cag gtg ggg     893
Thr Gly Arg Gln Ser Val Val Val Pro Tyr Glu Pro Pro Gln Val Gly
                235                 240                 245 aca gaa ttc acc acc atc ctg tac aac ttc atg tgt aac agc agc tgt     941
Thr Glu Phe Thr Thr Ile Leu Tyr Asn Phe Met Cys Asn Ser Ser Cys
            250                 255                 260 gtg ggg ggc atg aac cga cgg ccc atc ctc atc atc acc ctg gag         989
Val Gly Gly Met Asn Arg Arg Pro Ile Leu Ile Ile Thr Leu Glu
        265                 270                 275 acg cgg gat ggg cag gtg ctg ggc cgc cgg tcc ttc gag ggc cgc atc    1037
Thr Arg Asp Gly Gln Val Leu Gly Arg Arg Ser Phe Glu Gly Arg Ile
    280                 285                 290 tgc gcc tgt cct ggc cgc gac cga aaa gcc gat gag gac cac tac cgg    1085
Cys Ala Cys Pro Gly Arg Asp Arg Lys Ala Asp Glu Asp His Tyr Arg
295                 300                 305                 310 gag cag cag gcc ttg aat gag agc tcc gcc aag aac ggg gct gcc agc    1133
Glu Gln Gln Ala Leu Asn Glu Ser Ser Ala Lys Asn Gly Ala Ala Ser
                315                 320                 325 aag cgc gcc ttc aag cag agt ccc cct gcc gtc ccc gcc ctg ggc ccg    1181
Lys Arg Ala Phe Lys Gln Ser Pro Pro Ala Val Pro Ala Leu Gly Pro
            330                 335                 340 ggt gtg aag aag cgg cgg cac gga gac gag gac acg tac tac ctg cag    1229
Gly Val Lys Lys Arg Arg His Gly Asp Glu Asp Thr Tyr Tyr Leu Gln
        345                 350                 355 gtg cga ggc cgc gag aac ttc gag atc ctg atg aag ctg aag gag agc    1277
Val Arg Gly Arg Glu Asn Phe Glu Ile Leu Met Lys Leu Lys Glu Ser
    360                 365                 370 ctg gag ctg atg gag ttg gtg ccg cag ccg ctg gta gac tcc tat cgg    1325
Leu Glu Leu Met Glu Leu Val Pro Gln Pro Leu Val Asp Ser Tyr Arg
375                 380                 385                 390
```

```
cag cag cag cag ctc cta cag agg ccg agt cac cta cag ccc cca tcc      1373
Gln Gln Gln Gln Leu Leu Gln Arg Pro Ser His Leu Gln Pro Pro Ser
                395                 400                 405 tac ggg ccg gtc ctc tcg ccc atg aac aag gtg cac ggg ggc gtg aac      1421
Tyr Gly Pro Val Leu Ser Pro Met Asn Lys Val His Gly Gly Val Asn
            410                 415                 420 aag ctg ccc tcc gtc aac cag ctg gtg ggc cag cct ccc ccg cac agc      1469
Lys Leu Pro Ser Val Asn Gln Leu Val Gly Gln Pro Pro Pro His Ser
        425                 430                 435 tcg gca gct aca ccc aac ctg gga cct gtg ggc tct ggg atg ctc aac      1517
Ser Ala Ala Thr Pro Asn Leu Gly Pro Val Gly Ser Gly Met Leu Asn
    440                 445                 450 aac cac ggc cac gca gtg cca gcc aac agc gag atg acc agc agc cac      1565
Asn His Gly His Ala Val Pro Ala Asn Ser Glu Met Thr Ser Ser His
455                 460                 465                 470 ggc acc cag tcc atg gtc tcg ggg tcc cac tgc act ccg cca ccc ccc      1613
Gly Thr Gln Ser Met Val Ser Gly Ser His Cys Thr Pro Pro Pro Pro
                475                 480                 485 tac cac gcc gac ccc agc ctc gtc agt ttt tta aca gga ttg ggg tgt      1661
Tyr His Ala Asp Pro Ser Leu Val Ser Phe Leu Thr Gly Leu Gly Cys
            490                 495                 500 cca aac tgc atc gag tat ttc acg tcc cag ggg tta cag agc att tac      1709
Pro Asn Cys Ile Glu Tyr Phe Thr Ser Gln Gly Leu Gln Ser Ile Tyr
        505                 510                 515 cac ctg cag aac ctg acc atc gag gac ctg ggg gcc ctg aag atc ccc      1757
His Leu Gln Asn Leu Thr Ile Glu Asp Leu Gly Ala Leu Lys Ile Pro
    520                 525                 530 gag cag tat cgc atg acc atc tgg cgg ggc ctg cag gac ctg aag cag      1805
Glu Gln Tyr Arg Met Thr Ile Trp Arg Gly Leu Gln Asp Leu Lys Gln
535                 540                 545                 550 ggc cac gac tac ggc gcc gcg cag cag ctg ctc cgc tcc agc aac      1853
Gly His Asp Tyr Gly Ala Ala Gln Gln Leu Leu Arg Ser Ser Asn
                555                 560                 565 gcg gcc gcc att tcc atc ggc ggc tcc ggg gag ctg cag cgc cag cgg      1901
Ala Ala Ala Ile Ser Ile Gly Gly Ser Gly Glu Leu Gln Arg Gln Arg
            570                 575                 580 gtc atg gag gcc gtg cac ttc cgc gtg cgc cac acc atc acc atc ccc      1949
Val Met Glu Ala Val His Phe Arg Val Arg His Thr Ile Thr Ile Pro
        585                 590                 595 aac cgc ggc ggc ccc ggc gcc ggc ccc gac gag tgg gcg gac ttc ggc      1997
Asn Arg Gly Gly Pro Gly Ala Gly Pro Asp Glu Trp Ala Asp Phe Gly
    600                 605                 610 ttc gac ctg ccc gac tgc aag gcc cgc aag cag ccc atc aag gag gag      2045
Phe Asp Leu Pro Asp Cys Lys Ala Arg Lys Gln Pro Ile Lys Glu Glu
615                 620                 625                 630 ttc acg gag gcc gag atc cac tgaggggccg ggcccagcca gagcctgtgc         2096
Phe Thr Glu Ala Glu Ile His
                635 caccgcccag agacccaggc cgcctcgctc tccttcctgt gtccaaaact gcctccggag    2156 gcagggcctc caggctgtgc ccggggaaag gcaaggtccg gcccatgccc cggcacctca    2216 ccggcccag gagaggccca gccaccaaag ccgcctgcgg acagcctgag tcacctgcag     2276 aaccttctgg agctgcccta atgctgggct tgcggggcag gggccggccc actctcagcc    2336 ctgccactgc cgggcgtgct ccatggcagg cgtgggtggg gaccgcagtg tcagctccga    2396 cctccaggcc tcatcctaga gactctgtca tctgccgatc aagcaaggtc cttccagagg    2456 aaagaatcct cttcgctggt ggactgccaa aaagtatttt cgacatcttt ttggttctgg    2516
```

```
agagtggtga gcagccaagc gactgtgtct gaaacaccgt gcattttcag ggaatgtccc   2576
taacgggctg gggactctct ctgctggact tgggagtggc ctttgccccc agcacactgt   2636
attctgcggg accgcctcct tcctgcccct aacaaccacc aaagtgttgc tgaaattgga   2696
gaaaactggg gaaggcgcaa cccctcccag gtgcgggaag catctggtac cgcctcggcc   2756
agtgcccctc agcctggcca cagtcacctc tccttgggga accctgggca gaaagggaca   2816
gcctgtcctt agaggaccgg aaattgtcaa tatttgataa aatgataccc ttttctac    2874
```

<210> SEQ ID NO 2
<211> LENGTH: 637
<212> TYPE: PRT
<213> ORGANISM: Cebus apella

<400> SEQUENCE: 2

```
Met Ala Gln Ser Thr Thr Thr Ser Pro Asp Gly Gly Thr Thr Phe Glu
  1               5                  10                  15

His Leu Trp Ser Ser Leu Glu Pro Asp Ser Thr Tyr Phe Asp Leu Pro
             20                  25                  30

Gln Ser Ser Arg Gly Asn Asn Glu Val Val Gly Gly Thr Asp Ser Ser
         35                  40                  45

Met Asp Val Phe His Leu Glu Gly Met Thr Thr Ser Val Met Ala Gln
     50                  55                  60

Phe Asn Leu Leu Ser Ser Thr Met Asp Gln Met Ser Ser Arg Ala Ala
 65                  70                  75                  80

Ser Ala Ser Pro Tyr Thr Pro Glu His Ala Ala Ser Val Pro Thr His
                 85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160

Ile Gln Ile Lys Val Ser Ala Pro Pro Pro Gly Thr Ala Ile Arg
                165                 170                 175

Ala Met Pro Val Tyr Lys Lys Ala Glu His Val Thr Asp Ile Val Lys
            180                 185                 190

Arg Cys Pro Asn His Glu Leu Gly Arg Asp Phe Asn Glu Gly Gln Ser
        195                 200                 205

Ala Pro Ala Ser His Leu Ile Arg Val Glu Gly Asn Asn Leu Ser Gln
    210                 215                 220

Tyr Val Asp Asp Pro Val Thr Gly Arg Gln Ser Val Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
            260                 265                 270

Ile Ile Ile Thr Leu Glu Thr Arg Asp Gly Gln Val Leu Gly Arg Arg
        275                 280                 285

Ser Phe Glu Gly Arg Ile Cys Ala Cys Pro Gly Arg Asp Arg Lys Ala
    290                 295                 300

Asp Glu Asp His Tyr Arg Glu Gln Gln Ala Leu Asn Glu Ser Ser Ala
305                 310                 315                 320
```

```
Lys Asn Gly Ala Ala Ser Lys Arg Ala Phe Lys Gln Ser Pro Pro Ala
                325                 330                 335

Val Pro Ala Leu Gly Pro Gly Val Lys Lys Arg Arg His Gly Asp Glu
            340                 345                 350

Asp Thr Tyr Tyr Leu Gln Val Arg Gly Arg Glu Asn Phe Glu Ile Leu
        355                 360                 365

Met Lys Leu Lys Glu Ser Leu Glu Leu Met Glu Leu Val Pro Gln Pro
370                 375                 380

Leu Val Asp Ser Tyr Arg Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415

Val His Gly Gly Val Asn Lys Leu Pro Ser Val Asn Gln Leu Val Gly
            420                 425                 430

Gln Pro Pro Pro His Ser Ser Ala Ala Thr Pro Asn Leu Gly Pro Val
        435                 440                 445

Gly Ser Gly Met Leu Asn Asn His Gly His Ala Val Pro Ala Asn Ser
450                 455                 460

Glu Met Thr Ser Ser His Gly Thr Gln Ser Met Val Ser Gly Ser His
465                 470                 475                 480

Cys Thr Pro Pro Pro Tyr His Ala Asp Pro Ser Leu Val Ser Phe
                485                 490                 495

Leu Thr Gly Leu Gly Cys Pro Asn Cys Ile Glu Tyr Phe Thr Ser Gln
            500                 505                 510

Gly Leu Gln Ser Ile Tyr His Leu Gln Asn Leu Thr Ile Glu Asp Leu
        515                 520                 525

Gly Ala Leu Lys Ile Pro Glu Gln Tyr Arg Met Thr Ile Trp Arg Gly
530                 535                 540

Leu Gln Asp Leu Lys Gln Gly His Asp Tyr Gly Ala Ala Ala Gln Gln
545                 550                 555                 560

Leu Leu Arg Ser Ser Asn Ala Ala Ala Ile Ser Ile Gly Gly Ser Gly
                565                 570                 575

Glu Leu Gln Arg Gln Arg Val Met Glu Ala Val His Phe Arg Val Arg
            580                 585                 590

His Thr Ile Thr Ile Pro Asn Arg Gly Pro Gly Ala Gly Pro Asp
        595                 600                 605

Glu Trp Ala Asp Phe Gly Phe Asp Leu Pro Asp Cys Lys Ala Arg Lys
610                 615                 620

Gln Pro Ile Lys Glu Glu Phe Thr Glu Ala Glu Ile His
625                 630                 635

<210> SEQ ID NO 3
<211> LENGTH: 2034
<212> TYPE: DNA
<213> ORGANISM: Cebus apella
<220> FEATURE:
<221> NAME/KEY: CDS
<222> LOCATION: 156..1652

<400> SEQUENCE: 3
tgcctccccg cccgcgcacc cgccccgagg cctgtgctcc tgcgaagggg acgcagcgaa      60
gccggggccc gcgccaggcc ggccgggacg gacgccgatg cccggagctg cgacggctgc     120
agagcgagct gccctcggag gccggtgtga ggaag atg gcc cag tcc acc acc        173
                                     Met Ala Gln Ser Thr Thr
                                       1               5
```

```
acc tcc ccc gat ggg ggc acc acg ttt gag cac ctc tgg agc tct ctg     221
Thr Ser Pro Asp Gly Gly Thr Thr Phe Glu His Leu Trp Ser Ser Leu
         10                  15                  20 gaa cca gac agc acc tac ttc gac ctt ccc cag tca agc cgg ggg aat     269
Glu Pro Asp Ser Thr Tyr Phe Asp Leu Pro Gln Ser Ser Arg Gly Asn
             25                  30                  35 aat gag gtg gtg ggt ggc acg gat tcc agc atg gac gtc ttc cac cta     317
Asn Glu Val Val Gly Gly Thr Asp Ser Ser Met Asp Val Phe His Leu
     40                  45                  50 gag ggc atg acc aca tct gtc atg gcc cag ttc aat ttg ctg agc agc     365
Glu Gly Met Thr Thr Ser Val Met Ala Gln Phe Asn Leu Leu Ser Ser
 55                  60                  65                  70 acc atg gac cag atg agc agc cgc gct gcc tcg gcc agc ccg tac acc     413
Thr Met Asp Gln Met Ser Ser Arg Ala Ala Ser Ala Ser Pro Tyr Thr
                 75                  80                  85 ccg gag cac gcc gcc agc gtg ccc acc cat tca ccc tac gca cag ccc     461
Pro Glu His Ala Ala Ser Val Pro Thr His Ser Pro Tyr Ala Gln Pro
             90                  95                 100 agc tcc acc ttc gac acc atg tcg ccc gcg cct gtc atc ccc tcc aac     509
Ser Ser Thr Phe Asp Thr Met Ser Pro Ala Pro Val Ile Pro Ser Asn
        105                 110                 115 acc gac tat ccc gga ccc cac cac ttc gag gtc act ttc cag cag tcc     557
Thr Asp Tyr Pro Gly Pro His His Phe Glu Val Thr Phe Gln Gln Ser
    120                 125                 130 agc acg gcc aag tca gcc acc tgg acg tac tcc cca ctc ttg aag aaa     605
Ser Thr Ala Lys Ser Ala Thr Trp Thr Tyr Ser Pro Leu Leu Lys Lys
135                 140                 145                 150 ctc tac tgc cag atc gcc aag aca tgc ccc atc cag atc aag gtg tcc     653
Leu Tyr Cys Gln Ile Ala Lys Thr Cys Pro Ile Gln Ile Lys Val Ser
                155                 160                 165 gcc cca ccg ccc ccg ggc acc gcc atc cgg gcc atg cct gtc tac aag     701
Ala Pro Pro Pro Pro Gly Thr Ala Ile Arg Ala Met Pro Val Tyr Lys
            170                 175                 180 aag gcg gag cac gtg acc gac atc gtg aag cgc tgc ccc aac cac gag     749
Lys Ala Glu His Val Thr Asp Ile Val Lys Arg Cys Pro Asn His Glu
        185                 190                 195 ctc ggg agg gac ttc aac gaa gga cag tct gcc cca gcc agc cac ctc     797
Leu Gly Arg Asp Phe Asn Glu Gly Gln Ser Ala Pro Ala Ser His Leu
    200                 205                 210 atc cgt gtg gaa ggc aat aat ctc tcg cag tat gtg gac gac cct gtc     845
Ile Arg Val Glu Gly Asn Asn Leu Ser Gln Tyr Val Asp Asp Pro Val
215                 220                 225                 230 acc ggc agg cag agc gtc gtg gtg ccc tat gag cca cca cag gtg ggg     893
Thr Gly Arg Gln Ser Val Val Val Pro Tyr Glu Pro Pro Gln Val Gly
                235                 240                 245 aca gaa ttc acc acc atc ctg tac aac ttc atg tgt aac agc agc tgt     941
Thr Glu Phe Thr Thr Ile Leu Tyr Asn Phe Met Cys Asn Ser Ser Cys
            250                 255                 260 gtg ggg ggc atg aac cga cgg ccc atc ctc atc atc acc ctg gag        989
Val Gly Gly Met Asn Arg Arg Pro Ile Leu Ile Ile Thr Leu Glu
        265                 270                 275 acg cgg gat ggg cag gtg ctg ggc cgc cgg tcc ttc gag ggc cgc atc    1037
Thr Arg Asp Gly Gln Val Leu Gly Arg Arg Ser Phe Glu Gly Arg Ile
    280                 285                 290 tgc gcc tgt cct ggc cgc gac cga aaa gcc gat gag gac cac tac cgg    1085
Cys Ala Cys Pro Gly Arg Asp Arg Lys Ala Asp Glu Asp His Tyr Arg
295                 300                 305                 310 gag cag cag gcc ttg aat gag agc tcc gcc aag aac ggg gct gcc agc    1133
Glu Gln Gln Ala Leu Asn Glu Ser Ser Ala Lys Asn Gly Ala Ala Ser
```

```
aag cgc gcc ttc aag cag agt ccc cct gcc gtc ccc gcc ctg ggc ccg    1181
Lys Arg Ala Phe Lys Gln Ser Pro Pro Ala Val Pro Ala Leu Gly Pro
            330                 335                 340 ggt gtg aag aag cgg cgg cac gga gac gag gac acg tac tac ctg cag    1229
Gly Val Lys Lys Arg Arg His Gly Asp Glu Asp Thr Tyr Tyr Leu Gln
        345                 350                 355 gtg cga ggc cgc gag aac ttc gag atc ctg atg aag ctg aag gag agc    1277
Val Arg Gly Arg Glu Asn Phe Glu Ile Leu Met Lys Leu Lys Glu Ser
    360                 365                 370 ctg gag ctg atg gag ttg gtg ccg cag ccg ctg gta gac tcc tat cgg    1325
Leu Glu Leu Met Glu Leu Val Pro Gln Pro Leu Val Asp Ser Tyr Arg
375                 380                 385                 390 cag cag cag cag ctc cta cag agg ccg agt cac cta cag ccc cca tcc    1373
Gln Gln Gln Gln Leu Leu Gln Arg Pro Ser His Leu Gln Pro Pro Ser
                395                 400                 405 tac ggg ccg gtc ctc tcg ccc atg aac aag gtg cac ggg ggc gtg aac    1421
Tyr Gly Pro Val Leu Ser Pro Met Asn Lys Val His Gly Gly Val Asn
            410                 415                 420 aag ctg ccc tcc gtc aac cag ctg gtg ggc cag cct ccc ccg cac agc    1469
Lys Leu Pro Ser Val Asn Gln Leu Val Gly Gln Pro Pro Pro His Ser
        425                 430                 435 tcg gca gct aca ccc aac ctg gga cct gtg ggc tct ggg atg ctc aac    1517
Ser Ala Ala Thr Pro Asn Leu Gly Pro Val Gly Ser Gly Met Leu Asn
    440                 445                 450 aac cac ggc cac gca gtg cca gcc aac agc gag atg acc agc agc cac    1565
Asn His Gly His Ala Val Pro Ala Asn Ser Glu Met Thr Ser Ser His
455                 460                 465                 470 ggc acc cag tcc atg gtc tcg ggg tcc cac tgc act ccg cca ccc ccc    1613
Gly Thr Gln Ser Met Val Ser Gly Ser His Cys Thr Pro Pro Pro Pro
                475                 480                 485 tac cac gcc gac ccc agc ctc gtc agg acc tgg ggg ccc tgaagatccc    1662
Tyr His Ala Asp Pro Ser Leu Val Arg Thr Trp Gly Pro
            490                 495 cgagcagtat cgcatgacca tctggcgggg cctgcaggac ctgaagcagg gccacgacta   1722
cggcgccgcc gcgcagcagc tgctccgctc cagcaacgcg gccgccattt ccatcggcgg   1782
ctccggggag ctgcagcgcc agcgggtcat ggaggccgtg cacttccgcg tgcgccacac   1842
catcaccatc cccaaccgcg gcgggccccgg cgccggcccc gacgagtggg cggacttcgg   1902
cttcgacctg cccgactgca aggcccgcaa gcagcccatc aaggaggagt tcacggaggc   1962
cgagatccac tgaggggccg ggcccagcca gagcctgtgc caccgcccag agacccaggc   2022
cgcctcgctc tc                                                      2034

<210> SEQ ID NO 4
<211> LENGTH: 499
<212> TYPE: PRT
<213> ORGANISM: Cebus apella

<400> SEQUENCE: 4

Met Ala Gln Ser Thr Thr Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
    50                  55                  60
```

-continued

```
Phe Asn Leu Leu Ser Ser Thr Met Asp Gln Met Ser Ser Arg Ala Ala
 65                  70                  75                  80

Ser Ala Ser Pro Tyr Thr Pro Glu His Ala Ala Ser Val Pro Thr His
                 85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160

Ile Gln Ile Lys Val Ser Ala Pro Pro Pro Gly Thr Ala Ile Arg
                165                 170                 175

Ala Met Pro Val Tyr Lys Lys Ala Glu His Val Thr Asp Ile Val Lys
            180                 185                 190

Arg Cys Pro Asn His Glu Leu Gly Arg Asp Phe Asn Glu Gly Gln Ser
        195                 200                 205

Ala Pro Ala Ser His Leu Ile Arg Val Glu Gly Asn Asn Leu Ser Gln
    210                 215                 220

Tyr Val Asp Asp Pro Val Thr Gly Arg Gln Ser Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
            260                 265                 270

Ile Ile Ile Thr Leu Glu Thr Arg Asp Gly Gln Val Leu Gly Arg Arg
        275                 280                 285

Ser Phe Glu Gly Arg Ile Cys Ala Cys Pro Gly Arg Asp Arg Lys Ala
    290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                325                 330                 335

Val Pro Ala Leu Gly Pro Gly Val Lys Lys Arg Arg His Gly Asp Glu
            340                 345                 350

Asp Thr Tyr Tyr Leu Gln Val Arg Gly Arg Glu Asn Phe Glu Ile Leu
        355                 360                 365

Met Lys Leu Lys Glu Ser Leu Glu Leu Met Glu Leu Val Pro Gln Pro
    370                 375                 380

Leu Val Asp Ser Tyr Arg Gln Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415

Val His Gly Gly Val Asn Lys Leu Pro Ser Val Asn Gln Leu Val Gly
            420                 425                 430

Gln Pro Pro Pro His Ser Ser Ala Ala Thr Pro Asn Leu Gly Pro Val
        435                 440                 445

Gly Ser Gly Met Leu Asn Asn His Gly His Ala Val Pro Ala Asn Ser
    450                 455                 460

Glu Met Thr Ser Ser His Gly Thr Gln Ser Met Val Ser Gly Ser His
465                 470                 475                 480
```

```
Cys Thr Pro Pro Pro Tyr His Ala Asp Pro Ser Leu Val Arg Thr
            485                 490                 495

Trp Gly Pro

<210> SEQ ID NO 5
<211> LENGTH: 2156
<212> TYPE: DNA
<213> ORGANISM: Homo sapiens
<220> FEATURE:
<221> NAME/KEY: CDS
<222> LOCATION: 33..1940

<400> SEQUENCE: 5
gcgagctgcc ctcggaggcc ggcgtgggga ag atg gcc cag tcc acc gcc acc      53
                                   Met Ala Gln Ser Thr Ala Thr
                                     1               5 tcc cct gat ggg ggc acc acg ttt gag cac ctc tgg agc tct ctg gaa     101
Ser Pro Asp Gly Gly Thr Thr Phe Glu His Leu Trp Ser Ser Leu Glu
         10                  15                  20 cca gac agc acc tac ttc gac ctt ccc cag tca agc cgg ggg aat aat     149
Pro Asp Ser Thr Tyr Phe Asp Leu Pro Gln Ser Ser Arg Gly Asn Asn
     25                  30                  35 gag gtg gtg ggc gga acg gat ccc agc atg gac gtc ttc cac ctg gag     197
Glu Val Val Gly Gly Thr Asp Ser Ser Met Asp Val Phe His Leu Glu
 40                  45                  50                  55 ggc atg act aca tct gtc atg gcc cag ttc aat ctg ctg agc agc acc     245
Gly Met Thr Thr Ser Val Met Ala Gln Phe Asn Leu Leu Ser Ser Thr
                 60                  65                  70 atg gac cag atg agc agc cgc gcg gcc tcg gcc agc ccc tac acc cca     293
Met Asp Gln Met Ser Ser Arg Ala Ala Ser Ala Ser Pro Tyr Thr Pro
             75                  80                  85 gag cac gcc gcc agc gtg ccc acc cac tcg ccc tac gca caa ccc agc     341
Glu His Ala Ala Ser Val Pro Thr His Ser Pro Tyr Ala Gln Pro Ser
         90                  95                 100 tcc acc ttc gac acc atg tcg ccg gcg cct gtc atc ccc tcc aac acc     389
Ser Thr Phe Asp Thr Met Ser Pro Ala Pro Val Ile Pro Ser Asn Thr
    105                 110                 115 gac tac ccc gga ccc cac cac ttt gag gtc act ttc cag cag tcc agc     437
Asp Tyr Pro Gly Pro His His Phe Glu Val Thr Phe Gln Gln Ser Ser
120                 125                 130                 135 acg gcc aag tca gcc acc tgg acg tac tcc ccg ctc ttg aag aaa ctc     485
Thr Ala Lys Ser Ala Thr Trp Thr Tyr Ser Pro Leu Leu Lys Lys Leu
                140                 145                 150 tac tgc cag atc gcc aag aca tgc ccc atc cag atc aag gtg tcc acc     533
Tyr Cys Gln Ile Ala Lys Thr Cys Pro Ile Gln Ile Lys Val Ser Thr
            155                 160                 165 ccg cca ccc cca ggc act gcc atc cgg gcc atg cct gtt tac aag aaa     581
Pro Pro Pro Pro Gly Thr Ala Ile Arg Ala Met Pro Val Tyr Lys Lys
        170                 175                 180 gcg gag cac gtg acc gac gtc gtg aaa cgc tgc ccc aac cac gag ctc     629
Ala Glu His Val Thr Asp Val Val Lys Arg Cys Pro Asn His Glu Leu
    185                 190                 195 ggg agg gac ttc aac gaa gga cag tct gct cca gcc agc cac ctc atc     677
Gly Arg Asp Phe Asn Glu Gly Gln Ser Ala Pro Ala Ser His Leu Ile
200                 205                 210                 215 cgc gtg gaa ggc aat aat ctc tcg cag tat gtg gat gac cct gtc acc     725
Arg Val Glu Gly Asn Asn Leu Ser Gln Tyr Val Asp Asp Pro Val Thr
                220                 225                 230 ggc agg cag agc gtc gtg gtg ccc tat gag cca cca cag gtg ggg acg     773
Gly Arg Gln Ser Val Val Val Pro Tyr Glu Pro Pro Gln Val Gly Thr
            235                 240                 245
```

-continued

| | | |
|---|---|---|
| gaa ttc acc acc atc ctg tac aac ttc atg tgt aac agc agc tgt gta<br>Glu Phe Thr Thr Ile Leu Tyr Asn Phe Met Cys Asn Ser Ser Cys Val<br>250                        255                  260 | 821 |
| ggg ggc atg aac cgg cgg ccc atc ctc atc atc atc acc ctg gag atg<br>Gly Gly Met Asn Arg Arg Pro Ile Leu Ile Ile Ile Thr Leu Glu Met<br>265                        270                  275 | 869 |
| cgg gat ggg cag gtg ctg ggc cgc cgg tcc ttt gag ggc cgc atc tgc<br>Arg Asp Gly Gln Val Leu Gly Arg Arg Ser Phe Glu Gly Arg Ile Cys<br>280                        285                  290                  295 | 917 |
| gcc tgt cct ggc cgc gac cga aaa gct gat gag gac cac tac cgg gag<br>Ala Cys Pro Gly Arg Asp Arg Lys Ala Asp Glu Asp His Tyr Arg Glu<br>                      300                  305                  310 | 965 |
| cag cag gcc ctg aac gag agc tcc gcc aag aac ggg gcc gcc agc aag<br>Gln Gln Ala Leu Asn Glu Ser Ser Ala Lys Asn Gly Ala Ala Ser Lys<br>315                        320                  325 | 1013 |
| cgt gcc ttc aag cag agc ccc cct gcc gtc ccc gcc ctt ggt gcc ggt<br>Arg Ala Phe Lys Gln Ser Pro Pro Ala Val Pro Ala Leu Gly Ala Gly<br>330                        335                  340 | 1061 |
| gtg aag aag cgg cgg cat gga gac gag gac acg tac tac ctt cag gtg<br>Val Lys Lys Arg Arg His Gly Asp Glu Asp Thr Tyr Tyr Leu Gln Val<br>345                        350                  355 | 1109 |
| cga ggc cgg gag aac ttt gag atc ctg atg aag ctg aaa gag agc ctg<br>Arg Gly Arg Glu Asn Phe Glu Ile Leu Met Lys Leu Lys Glu Ser Leu<br>360                        365                  370                  375 | 1157 |
| gag ctg atg gag ttg gtg ccg cag cca ctg gtg gac tcc tat cgg cag<br>Glu Leu Met Glu Leu Val Pro Gln Pro Leu Val Asp Ser Tyr Arg Gln<br>                      380                  385                  390 | 1205 |
| cag cag cag ctc cta cag agg ccg agt cac cta cag ccc ccg tcc tac<br>Gln Gln Gln Leu Leu Gln Arg Pro Ser His Leu Gln Pro Pro Ser Tyr<br>395                        400                  405 | 1253 |
| ggg ccg gtc ctc tcg ccc atg aac aag gtg cac ggg ggc atg aac aag<br>Gly Pro Val Leu Ser Pro Met Asn Lys Val His Gly Gly Met Asn Lys<br>410                        415                  420 | 1301 |
| ctg ccc tcc gtc aac cag ctg gtg ggc cag cct ccg cac agt tcg<br>Leu Pro Ser Val Asn Gln Leu Val Gly Gln Pro Pro His Ser Ser<br>425                        430                  435 | 1349 |
| gca gct aca ccc aac ctg ggg ccc gtg ggc ccc ggg atg ctc aac aac<br>Ala Ala Thr Pro Asn Leu Gly Pro Val Gly Pro Gly Met Leu Asn Asn<br>440                        445                  450                  455 | 1397 |
| cat ggc cac gca gtg cca gcc aac ggc gag atg agc agc agc cac agc<br>His Gly His Ala Val Pro Ala Asn Gly Glu Met Ser Ser Ser His Ser<br>                      460                  465                  470 | 1445 |
| gcc cag tcc atg gtc tcg ggg tcc cac tgc act ccg cca ccc ccc tac<br>Ala Gln Ser Met Val Ser Gly Ser His Cys Thr Pro Pro Pro Pro Tyr<br>475                        480                  485 | 1493 |
| cac gcc gac ccc agc ctc gtc agt ttt tta aca gga ttg ggg tgt cca<br>His Ala Asp Pro Ser Leu Val Ser Phe Leu Thr Gly Leu Gly Cys Pro<br>490                        495                  500 | 1541 |
| aac tgc atc gag tat ttc acc tcc caa ggg tta cag agc att tac cac<br>Asn Cys Ile Glu Tyr Phe Thr Ser Gln Gly Leu Gln Ser Ile Tyr His<br>505                        510                  515 | 1589 |
| ctg cag aac ctg acc att gag gac ctg ggg gcc ctg aag atc ccc gag<br>Leu Gln Asn Leu Thr Ile Glu Asp Leu Gly Ala Leu Lys Ile Pro Glu<br>520                        525                  530                  535 | 1637 |
| cag tac cgc atg acc atc tgg cgg ggc ctg cag gac ctg aag cag ggc<br>Gln Tyr Arg Met Thr Ile Trp Arg Gly Leu Gln Asp Leu Lys Gln Gly<br>                      540                  545                  550 | 1685 |
| cac gac tac agc acc gcg cag cag ctg ctc cgc tct agc aac gcg gcc<br>His Asp Tyr Ser Thr Ala Gln Gln Leu Leu Arg Ser Ser Asn Ala Ala | 1733 |

-continued

```
                555                 560                 565
acc atc tcc atc ggc ggc tca ggg gaa ctg cag cgc cag cgg gtc atg        1781
Thr Ile Ser Ile Gly Gly Ser Gly Glu Leu Gln Arg Gln Arg Val Met
            570                 575                 580 gag gcc gtg cac ttc cgc gtg cgc cac acc atc acc atc ccc aac cgc        1829
Glu Ala Val His Phe Arg Val Arg His Thr Ile Thr Ile Pro Asn Arg
        585                 590                 595 ggc ggc cca ggc ggc ggc cct gac gag tgg gcg gac ttc ggc ttc gac        1877
Gly Gly Pro Gly Gly Gly Pro Asp Glu Trp Ala Asp Phe Gly Phe Asp
600                 605                 610                 615 ctg ccc gac tgc aag gcc cgc aag cag ccc atc aag gag gag ttc acg        1925
Leu Pro Asp Cys Lys Ala Arg Lys Gln Pro Ile Lys Glu Glu Phe Thr
                620                 625                 630 gag gcc gag atc cac tgagggcctc gcctggctgc agcctgcgcc accgcccaga        1980
Glu Ala Glu Ile His
                635 gacccaagct gcctcccctc tccttcctgt gtgtccaaaa ctgcctcagg aggcaggacc      2040 ttcgggctgt gcccggggaa aggcaaggtc cggcccatcc ccaggcacct cacaggcccc      2100 aggaaaggcc cagccaccga agccgcctgt ggacagcctg agtcacctgc agaacc          2156
```

<210> SEQ ID NO 6
<211> LENGTH: 636
<212> TYPE: PRT
<213> ORGANISM: Homo sapiens

<400> SEQUENCE: 6

```
Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
    50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
    130                 135                 140

Ser Pro Leu Leu Lys Lys Leu Tyr Cys Gln Ile Ala Lys Thr Cys Pro
145                 150                 155                 160

Ile Gln Ile Lys Val Ser Thr Pro Pro Pro Gly Thr Ala Ile Arg
                165                 170                 175

Ala Met Pro Val Tyr Lys Lys Ala Glu His Val Thr Asp Val Val Lys
            180                 185                 190

Arg Cys Pro Asn His Glu Leu Gly Arg Asp Phe Asn Glu Gly Gln Ser
        195                 200                 205

Ala Pro Ala Ser His Leu Ile Arg Val Glu Gly Asn Asn Leu Ser Gln
    210                 215                 220

Tyr Val Asp Asp Pro Val Thr Gly Arg Gln Ser Val Val Val Pro Tyr
```

```
            225                 230                 235                 240
Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
        260                 265                 270

Ile Ile Ile Thr Leu Glu Met Arg Asp Gly Gln Val Leu Gly Arg Arg
            275                 280                 285

Ser Phe Glu Gly Arg Ile Cys Ala Cys Pro Gly Arg Asp Arg Lys Ala
        290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                325                 330                 335

Val Pro Ala Leu Gly Ala Gly Val Lys Lys Arg Arg His Gly Asp Glu
            340                 345                 350

Asp Thr Tyr Tyr Leu Gln Val Arg Gly Arg Glu Asn Phe Glu Ile Leu
        355                 360                 365

Met Lys Leu Lys Glu Ser Leu Glu Leu Met Glu Leu Val Pro Gln Pro
    370                 375                 380

Leu Val Asp Ser Tyr Arg Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415

Val His Gly Gly Met Asn Lys Leu Pro Ser Val Asn Gln Leu Val Gly
            420                 425                 430

Gln Pro Pro Pro His Ser Ser Ala Ala Thr Pro Asn Leu Gly Pro Val
        435                 440                 445

Gly Pro Gly Met Leu Asn Asn His Gly His Ala Val Pro Ala Asn Gly
    450                 455                 460

Glu Met Ser Ser Ser His Ser Ala Gln Ser Met Val Ser Gly Ser His
465                 470                 475                 480

Cys Thr Pro Pro Pro Tyr His Ala Asp Pro Ser Leu Val Ser Phe
                485                 490                 495

Leu Thr Gly Leu Gly Cys Pro Asn Cys Ile Glu Tyr Phe Thr Ser Gln
            500                 505                 510

Gly Leu Gln Ser Ile Tyr His Leu Gln Asn Leu Thr Ile Glu Asp Leu
        515                 520                 525

Gly Ala Leu Lys Ile Pro Glu Gln Tyr Arg Met Thr Ile Trp Arg Gly
    530                 535                 540

Leu Gln Asp Leu Lys Gln Gly His Asp Tyr Ser Thr Ala Gln Gln Leu
545                 550                 555                 560

Leu Arg Ser Ser Asn Ala Ala Thr Ile Ser Ile Gly Ser Gly Glu
                565                 570                 575

Leu Gln Arg Gln Arg Val Met Glu Ala Val His Phe Arg Val Arg His
            580                 585                 590

Thr Ile Thr Ile Pro Asn Arg Gly Gly Pro Gly Gly Pro Asp Glu
        595                 600                 605

Trp Ala Asp Phe Gly Phe Asp Leu Pro Asp Cys Lys Ala Arg Lys Gln
    610                 615                 620

Pro Ile Lys Glu Glu Phe Thr Glu Ala Glu Ile His
625                 630                 635

<210> SEQ ID NO 7
```

```
<211> LENGTH: 2040
<212> TYPE: DNA
<213> ORGANISM: Mus musculus
<220> FEATURE:
<221> NAME/KEY: CDS
<222> LOCATION: 124..1890

<400> SEQUENCE: 7
tgatctccct gtggcctgca ggggactgag ccagggagta gatgccctga gaccccaagg      60
gacacccaag gaaaccttgc tggctttgag aagggatcg tctctctcct gcccaagaga      120 agc atg tgt atg ggc cct gtg tat gaa tcc ttg ggg cag gcc cag ttc      168
    Met Cys Met Gly Pro Val Tyr Glu Ser Leu Gly Gln Ala Gln Phe
    1               5                  10                 15 aat ttg ctc agc agt gcc atg gac cag atg ggc agc cgt gcg gcc ccg      216
Asn Leu Leu Ser Ser Ala Met Asp Gln Met Gly Ser Arg Ala Ala Pro
            20                  25                  30 gcg agc ccc tac acc ccg gag cac gcc gcc agc gcg ccc acc cac tcg      264
Ala Ser Pro Tyr Thr Pro Glu His Ala Ala Ser Ala Pro Thr His Ser
        35                  40                  45 ccc tac gcg cag ccc agc tcc acc ttc gac acc atg tct ccg gcg cct      312
Pro Tyr Ala Gln Pro Ser Ser Thr Phe Asp Thr Met Ser Pro Ala Pro
    50                  55                  60 gtc atc cct tcc aat acc gac tac ccc ggc ccc cac cac ttc gag gtc      360
Val Ile Pro Ser Asn Thr Asp Tyr Pro Gly Pro His His Phe Glu Val
65                  70                  75 acc ttc cag cag tcg agc act gcc aag tcg gcc acc tgg aca tac tcc      408
Thr Phe Gln Gln Ser Ser Thr Ala Lys Ser Ala Thr Trp Thr Tyr Ser
            80                  85                  90                  95 cca ctc ttg aag aag ttg tac tgt cag att gct aag aca tgc ccc atc      456
Pro Leu Leu Lys Lys Leu Tyr Cys Gln Ile Ala Lys Thr Cys Pro Ile
                100                 105                 110 cag atc aaa gtg tcc aca cca cca ccc ccg ggc acg gcc atc cgg gcc      504
Gln Ile Lys Val Ser Thr Pro Pro Pro Pro Gly Thr Ala Ile Arg Ala
            115                 120                 125 atg cct gtc tac aag aag gca gag cat gtg acc gac att gtt aag cgc      552
Met Pro Val Tyr Lys Lys Ala Glu His Val Thr Asp Ile Val Lys Arg
        130                 135                 140 tgc ccc aac cac gag ctt gga agg gac ttc aat gaa gga cag tct gcc      600
Cys Pro Asn His Glu Leu Gly Arg Asp Phe Asn Glu Gly Gln Ser Ala
    145                 150                 155 ccg gct agc cac ctc atc cgt gta gaa ggc aac aac ctc gcc cag tac      648
Pro Ala Ser His Leu Ile Arg Val Glu Gly Asn Asn Leu Ala Gln Tyr
160                 165                 170                 175 gtg gat gac cct gtc acc gga agg cag agt gtg gtt gtg ccg tat gaa      696
Val Asp Asp Pro Val Thr Gly Arg Gln Ser Val Val Val Pro Tyr Glu
                180                 185                 190 ccc cca cag gtg gga aca gaa ttt acc acc atc ctg tac aac ttc atg      744
Pro Pro Gln Val Gly Thr Glu Phe Thr Thr Ile Leu Tyr Asn Phe Met
            195                 200                 205 tgt aac agc agc tgt gtg ggg ggc atg aat cgg agg ccc atc ctt gtc      792
Cys Asn Ser Ser Cys Val Gly Gly Met Asn Arg Arg Pro Ile Leu Val
        210                 215                 220 atc atc acc ctg gag acc cgg gat gga cag gtc ctg ggc cgc cgg tct      840
Ile Ile Thr Leu Glu Thr Arg Asp Gly Gln Val Leu Gly Arg Arg Ser
    225                 230                 235 ttc gag ggt cgc atc tgt gcc tgt cct ggc cgt gac cgc aaa gct gat      888
Phe Glu Gly Arg Ile Cys Ala Cys Pro Gly Arg Asp Arg Lys Ala Asp
240                 245                 250                 255 gaa gac cat tac cgg gag caa cag gct ctg aat gaa agt acc acc aaa      936
Glu Asp His Tyr Arg Glu Gln Gln Ala Leu Asn Glu Ser Thr Thr Lys
```

-continued

```
                  260                 265                 270
aat gga gct gcc agc aaa cgt gca ttc aag cag agc ccc cct gcc atc      984
Asn Gly Ala Ala Ser Lys Arg Ala Phe Lys Gln Ser Pro Pro Ala Ile
            275                 280                 285 cct gcc ctg ggt acc aac gtg aag aag aga cgc cac ggg gac gag gac     1032
Pro Ala Leu Gly Thr Asn Val Lys Lys Arg Arg His Gly Asp Glu Asp
            290                 295                 300 atg ttc tac atg cac gtg cga ggc cgg gag aac ttt gag atc ttg atg     1080
Met Phe Tyr Met His Val Arg Gly Arg Glu Asn Phe Glu Ile Leu Met
            305                 310                 315 aaa gtc aag gag agc cta gaa ctg atg gag ctt gtg ccc cag cct ttg     1128
Lys Val Lys Glu Ser Leu Glu Leu Met Glu Leu Val Pro Gln Pro Leu
320                 325                 330                 335 gtt gac tcc tat cga cag cag cag cag cag ctc cta cag agg ccg         1176
Val Asp Ser Tyr Arg Gln Gln Gln Gln Gln Leu Leu Gln Arg Pro
                340                 345                 350 agt cac ctg cag cct cca tcc tat ggg ccc gtg ctc tcc cca atg aac     1224
Ser His Leu Gln Pro Pro Ser Tyr Gly Pro Val Leu Ser Pro Met Asn
            355                 360                 365 aag gta cac ggt ggt gtc aac aaa ctg ccc tcc gtc aac cag ctg gtg     1272
Lys Val His Gly Gly Val Asn Lys Leu Pro Ser Val Asn Gln Leu Val
            370                 375                 380 ggc cag cct ccc ccg cac agc tca gca gct ggg ccc aac ctg ggg ccc     1320
Gly Gln Pro Pro Pro His Ser Ser Ala Ala Gly Pro Asn Leu Gly Pro
385                 390                 395 atg ggc tcc ggg atg ctc aac agc cac ggc cac agc atg ccg gcc aat     1368
Met Gly Ser Gly Met Leu Asn Ser His Gly His Ser Met Pro Ala Asn
400                 405                 410                 415 ggt gag atg aat gga ggc cac agc tcc cag acc atg gtt tcg gga tcc     1416
Gly Glu Met Asn Gly Gly His Ser Ser Gln Thr Met Val Ser Gly Ser
                420                 425                 430 cac tgc acc ccg cca ccc ccc tat cat gca gac ccc agc ctc gtc agt     1464
His Cys Thr Pro Pro Pro Pro Tyr His Ala Asp Pro Ser Leu Val Ser
            435                 440                 445 ttt ttg aca ggg ttg ggg tgt cca aac tgc atc gag tgc ttc act tcc     1512
Phe Leu Thr Gly Leu Gly Cys Pro Asn Cys Ile Glu Cys Phe Thr Ser
            450                 455                 460 caa ggg ttg cag agc atc tac cac ctg cag aac ctt acc atc gag gac     1560
Gln Gly Leu Gln Ser Ile Tyr His Leu Gln Asn Leu Thr Ile Glu Asp
465                 470                 475 ctt ggg gct ctg aag gtc cct gac cag tac cgt atg acc atc tgg agg     1608
Leu Gly Ala Leu Lys Val Pro Asp Gln Tyr Arg Met Thr Ile Trp Arg
480                 485                 490                 495 ggc cta cag gac ctg aag cag agc cat gac tgc ggc cag caa ctg cta     1656
Gly Leu Gln Asp Leu Lys Gln Ser His Asp Cys Gly Gln Gln Leu Leu
                500                 505                 510 cgc tcc agc agc aac gcg gcc acc atc tcc atc ggc ggc tct ggc gag     1704
Arg Ser Ser Ser Asn Ala Ala Thr Ile Ser Ile Gly Gly Ser Gly Glu
            515                 520                 525 ctg cag cgg cag cgg gtc atg gaa gcc gtg cat ttc cgt gtg cgc cac     1752
Leu Gln Arg Gln Arg Val Met Glu Ala Val His Phe Arg Val Arg His
            530                 535                 540 acc atc aca atc ccc aac cgt gga ggc gca ggt gcg gtg aca ggt ccc     1800
Thr Ile Thr Ile Pro Asn Arg Gly Gly Ala Gly Ala Val Thr Gly Pro
545                 550                 555 gac gag tgg gcg gac ttt ggc ttt gac ctg cct gac tgc aag tcc cgt     1848
Asp Glu Trp Ala Asp Phe Gly Phe Asp Leu Pro Asp Cys Lys Ser Arg
560                 565                 570                 575 aag cag ccc atc aaa gag gag ttc aca gag aca gag agc cac                1890
Lys Gln Pro Ile Lys Glu Glu Phe Thr Glu Thr Glu Ser His
```

-continued

```
Lys Gln Pro Ile Lys Glu Glu Phe Thr Glu Thr Glu Ser His
                580                 585 tgaggaacgt accttcttct cctgtccttc ctctgtgaga aactgctctt ggaagtggga    1950
cctgttggct gtgcccacag aaaccagcaa ggaccttctg ccggatgcca ttcctgaagg    2010
gaagtcgctc atgaactaac tccctcttgg                                    2040

<210> SEQ ID NO 8
<211> LENGTH: 589
<212> TYPE: PRT
<213> ORGANISM: Mus musculus

<400> SEQUENCE: 8

Met Cys Met Gly Pro Val Tyr Glu Ser Leu Gly Gln Ala Gln Phe Asn
 1               5                  10                  15

Leu Leu Ser Ser Ala Met Asp Gln Met Gly Ser Arg Ala Ala Pro Ala
            20                  25                  30

Ser Pro Tyr Thr Pro Glu His Ala Ala Ser Ala Pro Thr His Ser Pro
        35                  40                  45

Tyr Ala Gln Pro Ser Ser Thr Phe Asp Thr Met Ser Pro Ala Pro Val
    50                  55                  60

Ile Pro Ser Asn Thr Asp Tyr Pro Gly Pro His His Phe Glu Val Thr
65                  70                  75                  80

Phe Gln Gln Ser Ser Thr Ala Lys Ser Ala Thr Trp Thr Tyr Ser Pro
                85                  90                  95

Leu Leu Lys Lys Leu Tyr Cys Gln Ile Ala Lys Thr Cys Pro Ile Gln
            100                 105                 110

Ile Lys Val Ser Thr Pro Pro Pro Gly Thr Ala Ile Arg Ala Met
        115                 120                 125

Pro Val Tyr Lys Lys Ala Glu His Val Thr Asp Ile Val Lys Arg Cys
    130                 135                 140

Pro Asn His Glu Leu Gly Arg Asp Phe Asn Glu Gly Gln Ser Ala Pro
145                 150                 155                 160

Ala Ser His Leu Ile Arg Val Glu Gly Asn Asn Leu Ala Gln Tyr Val
                165                 170                 175

Asp Asp Pro Val Thr Gly Arg Gln Ser Val Val Pro Tyr Glu Pro
            180                 185                 190

Pro Gln Val Gly Thr Glu Phe Thr Thr Ile Leu Tyr Asn Phe Met Cys
        195                 200                 205

Asn Ser Ser Cys Val Gly Gly Met Asn Arg Arg Pro Ile Leu Val Ile
    210                 215                 220

Ile Thr Leu Glu Thr Arg Asp Gly Gln Val Leu Gly Arg Arg Ser Phe
225                 230                 235                 240

Glu Gly Arg Ile Cys Ala Cys Pro Gly Arg Asp Arg Lys Ala Asp Glu
                245                 250                 255

Asp His Tyr Arg Glu Gln Gln Ala Leu Asn Glu Ser Thr Thr Lys Asn
            260                 265                 270

Gly Ala Ala Ser Lys Arg Ala Phe Lys Gln Ser Pro Pro Ala Ile Pro
        275                 280                 285

Ala Leu Gly Thr Asn Val Lys Lys Arg Arg His Gly Asp Glu Asp Met
    290                 295                 300

Phe Tyr Met His Val Arg Gly Arg Glu Asn Phe Glu Ile Leu Met Lys
305                 310                 315                 320

Val Lys Glu Ser Leu Glu Leu Met Glu Leu Val Pro Gln Pro Leu Val
                325                 330                 335
```

Asp Ser Tyr Arg Gln Gln Gln Gln Gln Leu Leu Gln Arg Pro Ser
            340                 345                 350

His Leu Gln Pro Pro Ser Tyr Gly Pro Val Leu Ser Pro Met Asn Lys
            355                 360                 365

Val His Gly Gly Val Asn Lys Leu Pro Ser Val Asn Gln Leu Val Gly
            370                 375                 380

Gln Pro Pro His Ser Ala Ala Gly Pro Asn Leu Gly Pro Met
385                 390                 395                 400

Gly Ser Gly Met Leu Asn Ser His Gly His Ser Met Pro Ala Asn Gly
            405                 410                 415

Glu Met Asn Gly Gly His Ser Ser Gln Thr Met Val Ser Gly Ser His
            420                 425                 430

Cys Thr Pro Pro Pro Tyr His Ala Asp Pro Ser Leu Val Ser Phe
            435                 440                 445

Leu Thr Gly Leu Gly Cys Pro Asn Cys Ile Glu Cys Phe Thr Ser Gln
            450                 455                 460

Gly Leu Gln Ser Ile Tyr His Leu Gln Asn Leu Thr Ile Glu Asp Leu
465                 470                 475                 480

Gly Ala Leu Lys Val Pro Asp Gln Tyr Arg Met Thr Ile Trp Arg Gly
            485                 490                 495

Leu Gln Asp Leu Lys Gln Ser His Asp Cys Gly Gln Gln Leu Leu Arg
            500                 505                 510

Ser Ser Ser Asn Ala Ala Thr Ile Ser Ile Gly Gly Ser Gly Glu Leu
            515                 520                 525

Gln Arg Gln Arg Val Met Glu Ala Val His Phe Arg Val Arg His Thr
            530                 535                 540

Ile Thr Ile Pro Asn Arg Gly Gly Ala Gly Ala Val Thr Gly Pro Asp
545                 550                 555                 560

Glu Trp Ala Asp Phe Gly Phe Asp Leu Pro Asp Cys Lys Ser Arg Lys
            565                 570                 575

Gln Pro Ile Lys Glu Glu Phe Thr Glu Thr Glu Ser His
            580                 585

<210> SEQ ID NO 9
<211> LENGTH: 758
<212> TYPE: DNA
<213> ORGANISM: Mus musculus
<220> FEATURE:
<221> NAME/KEY: CDS
<222> LOCATION: 389..757

<400> SEQUENCE: 9
tggtcccgct cgaccaaga ctccggctac cagcttgcgg gccccgcgga ggaggagacc    60 ccgctgggc tagctggcg acgcgcgcca agcggcggcg ggaaggaggc gggaggagcg   120
gggcccgaga ccccgactcg gcagagcca gctggggagg cggggcgcgc gtgggagcca   180
ggggcccggg tggccggccc tcctccgcca cggctgagtg cccgcgctgc cttccgccg   240 gtccgccaag aaaggcgcta agcctgcggc agtcccctcg ccgccgcctc cctgctccgc   300
acccttataa cccgccgtcc cgcatccagg cgaggaggca acgctgcagc ccagccctcg   360
ccgacgccga cgcccggccc ggagcaga atg agc ggc agc gtt ggg gag atg      412
                                Met Ser Gly Ser Val Gly Glu Met
                                1               5 gcc cag acc tct tct tcc tcc tcc acc ttc gag cac ctg tgg agt       460
Ala Gln Thr Ser Ser Ser Ser Ser Thr Phe Glu His Leu Trp Ser
   10              15                  20

```
tct cta gag cca gac agc acc tac ttt gac ctc ccc cag ccc agc caa      508
Ser Leu Glu Pro Asp Ser Thr Tyr Phe Asp Leu Pro Gln Pro Ser Gln
 25                  30                  35                  40 ggg act agc gag gca tca ggc agc gag gag tcc aac atg gat gtc ttc      556
Gly Thr Ser Glu Ala Ser Gly Ser Glu Glu Ser Asn Met Asp Val Phe
                 45                  50                  55 cac ctg caa ggc atg gcc cag ttc aat ttg ctc agc agt gcc atg gac      604
His Leu Gln Gly Met Ala Gln Phe Asn Leu Leu Ser Ser Ala Met Asp
             60                  65                  70 cag atg ggc agc cgt gcg gcc ccg gcg agc ccc tac acc ccg gag cac      652
Gln Met Gly Ser Arg Ala Ala Pro Ala Ser Pro Tyr Thr Pro Glu His
         75                  80                  85 gcc gcc agc gcg ccc acc cac tcg ccc tac gcg cag ccc agc tcc acc      700
Ala Ala Ser Ala Pro Thr His Ser Pro Tyr Ala Gln Pro Ser Ser Thr
     90                  95                 100 ttc gac acc atg tct ccg gcg cct gtc atc cct tcc aat acc gac tac      748
Phe Asp Thr Met Ser Pro Ala Pro Val Ile Pro Ser Asn Thr Asp Tyr
105                 110                 115                 120 ccc ggc ccc c                                                         758
Pro Gly Pro <210> SEQ ID NO 10
<211> LENGTH: 123
<212> TYPE: PRT
<213> ORGANISM: Mus musculus

<400> SEQUENCE: 10

Met Ser Gly Ser Val Gly Glu Met Ala Gln Thr Ser Ser Ser Ser Ser
 1               5                  10                  15

Ser Thr Phe Glu His Leu Trp Ser Ser Leu Glu Pro Asp Ser Thr Tyr
             20                  25                  30

Phe Asp Leu Pro Gln Pro Ser Gln Gly Thr Ser Glu Ala Ser Gly Ser
         35                  40                  45

Glu Glu Ser Asn Met Asp Val Phe His Leu Gln Gly Met Ala Gln Phe
     50                  55                  60

Asn Leu Leu Ser Ser Ala Met Asp Gln Met Gly Ser Arg Ala Ala Pro
 65                  70                  75                  80

Ala Ser Pro Tyr Thr Pro Glu His Ala Ala Ser Ala Pro Thr His Ser
                 85                  90                  95

Pro Tyr Ala Gln Pro Ser Ser Thr Phe Asp Thr Met Ser Pro Ala Pro
            100                 105                 110

Val Ile Pro Ser Asn Thr Asp Tyr Pro Gly Pro
        115                 120

<210> SEQ ID NO 11
<211> LENGTH: 559
<212> TYPE: DNA
<213> ORGANISM: Homo sapiens

<400> SEQUENCE: 11
cgaccttccc cagtcaagcc gggggaataa tgaggtggtg ggcggaacgg attccagcat      60
ggacgtcttc cacctggagg gcatgactac atctgtcatg catcctcggc tcctgcctca     120
ctagctgcgg agcctctccc gctcggtcca cgctgccggg cggccacgac cgtgacccct     180 ccctcgggc cgcccagatc catgcctcgt cccacgggac accagttccc tggcgtgtgc      240 agacccccg cgcctaccat gctgtacgt cggtgacccc gcacggcacc tcgccacggc      300
ccagttcaat ctgctgagca gcaccatgga ccagatgagc agccgcgcgg cctcggccag     360
```

```
cccctacacc ccagagcacg ccgccagcgt gcccacccac tcgccctacg cacaacccag    420
ctccaccttc gacaccatgt cgccggcgcc tgtcatcccc tccaacaccg actaccccgg    480
accccaccac tttgaggtca ctttccagca gtccagcacg gccaagtcag ccacctggac    540
gtactccccg ctcttgaag                                                 559

<210> SEQ ID NO 12
<211> LENGTH: 1764
<212> TYPE: DNA
<213> ORGANISM: Homo sapiens

<400> SEQUENCE: 12
atgctgtacg tcggtgaccc cgcacggcac ctcgccacgg cccagttcaa tctgctgagc     60
agcaccatgg accagatgag cagccgcgcg gcctcggcca gccctacac cccagagcac    120 gccgccagcg tgcccaccca ctcgccctac gcacaaccca gctccacctt cgacaccatg    180
tcgccggcgc ctgtcatccc ctccaacacc gactaccccg accccacca ctttgaggtc    240 actttccagc agtccagcac ggccaagtca gccacctgga cgtactcccc gctcttgaag    300
aaactctact gccagatcgc caagacatgc cccatccaga tcaaggtgtc caccccgcca    360
cccccaggca ctgccatccg ggccatgcct gtttacaaga agcggagca cgtgaccgac    420 gtcgtgaaac gctgccccaa ccacgagctc ggggaggact caacgaagg acagtctgct    480 ccagccagcc acctcatccg cgtggaaggc aataatctct cgcagtatgt ggatgaccct    540
gtcaccggca ggcagagcgt cgtggtgccc tatgagccac acaggtggg gacggaattc    600 accaccatcc tgtacaactt catgtgtaac agcagctgtg tagggggcat gaaccggcgg    660
cccatcctca tcatcatcac cctggagatg cgggatgggc aggtgctggg ccgccggtcc    720
tttgagggcc gcatctgcgc ctgtcctggc cgcgaccgaa aagctgatga ggaccactac    780
cgggagcagc aggccctgaa cgagagctcc gccaagaacg gggccgccag caagcgtgcc    840
ttcaagcaga gccccctgc cgtcccgcc cttggtgccg gtgtgaagaa gcggcggcat    900
ggagacgagg acacgtacta ccttcaggtg cgaggccggg agaactttga gatcctgatg    960
aagctgaaag agagcctgga gctgatggag ttggtgccgc agccactggt ggactcctat   1020
cggcagcagc agcagctcct acagaggccg agtcacctac agccccgtc ctacgggccg   1080 gtcctctcgc ccatgaacaa ggtgcacggg gcatgaaca agctgccctc cgtcaaccag   1140
ctggtgggcc agcctccccc gcacagttcg gcagctacac ccaacctggg gcccgtgggc   1200
cccgggatgc tcaacaacca tggccacgca gtgccagcca acggcgagat gagcagcagc   1260
cacagcgccc agtccatggt ctcggggtcc cactgcactc cgccaccccc ctaccacgcc   1320
gaccccagcc tcgtcagttt tttaacagga ttggggtgtc caaactgcat cgagtatttc   1380
acctcccaag ggttacagag catttaccac ctgcagaacc tgaccattga ggacctgggg   1440
gccctgaaga tccccgagca gtaccgcatg accatctggc ggggcctgca ggacctgaag   1500
cagggccacg actacagcac cgcgcagcag ctgctccgct ctagcaacgc ggccaccatc   1560
tccatcggcg gctcagggga actgcagcgc cagcgggtca tggaggccgt gcacttccgc   1620
gtgcgccaca ccatcaccat ccccaaccgc ggcggcccag gcggcggccc tgacgagtgg   1680
gcggacttcg gcttcgacct gcccgactgc aaggcccgca agcagcccat caaggaggag   1740
ttcacggagg ccgagatcca ctga                                          1764

<210> SEQ ID NO 13
```

<211> LENGTH: 587
<212> TYPE: PRT
<213> ORGANISM: Homo sapiens

<400> SEQUENCE: 13

```
Met Leu Tyr Val Gly Asp Pro Ala Arg His Leu Ala Thr Ala Gln Phe
1               5                   10                  15

Asn Leu Leu Ser Ser Thr Met Asp Gln Met Ser Ser Arg Ala Ala Ser
            20                  25                  30

Ala Ser Pro Tyr Thr Pro Glu His Ala Ala Ser Val Pro Thr His Ser
        35                  40                  45

Pro Tyr Ala Gln Pro Ser Ser Thr Phe Asp Thr Met Ser Pro Ala Pro
    50                  55                  60

Val Ile Pro Ser Asn Thr Asp Tyr Pro Gly Pro His His Phe Glu Val
65                  70                  75                  80

Thr Phe Gln Gln Ser Ser Thr Ala Lys Ser Ala Thr Trp Thr Tyr Ser
                85                  90                  95

Pro Leu Leu Lys Lys Leu Tyr Cys Gln Ile Ala Lys Thr Cys Pro Ile
            100                 105                 110

Gln Ile Lys Val Ser Thr Pro Pro Pro Gly Thr Ala Ile Arg Ala
        115                 120                 125

Met Pro Val Tyr Lys Lys Ala Glu His Val Thr Asp Val Val Lys Arg
130                 135                 140

Cys Pro Asn His Glu Leu Gly Arg Asp Phe Asn Glu Gly Gln Ser Ala
145                 150                 155                 160

Pro Ala Ser His Leu Ile Arg Val Glu Gly Asn Asn Leu Ser Gln Tyr
                165                 170                 175

Val Asp Asp Pro Val Thr Gly Arg Gln Ser Val Val Pro Tyr Glu
            180                 185                 190

Pro Pro Gln Val Gly Thr Glu Phe Thr Thr Ile Leu Tyr Asn Phe Met
        195                 200                 205

Cys Asn Ser Ser Cys Val Gly Gly Met Asn Arg Arg Pro Ile Leu Ile
    210                 215                 220

Ile Ile Thr Leu Glu Met Arg Asp Gly Gln Val Leu Gly Arg Arg Ser
225                 230                 235                 240

Phe Glu Gly Arg Ile Cys Ala Cys Pro Gly Arg Asp Arg Lys Ala Asp
                245                 250                 255

Glu Asp His Tyr Arg Glu Gln Gln Ala Leu Asn Glu Ser Ser Ala Lys
            260                 265                 270

Asn Gly Ala Ala Ser Lys Arg Ala Phe Lys Gln Ser Pro Pro Ala Val
        275                 280                 285

Pro Ala Leu Gly Ala Gly Val Lys Lys Arg Arg His Gly Asp Glu Asp
    290                 295                 300

Thr Tyr Tyr Leu Gln Val Arg Gly Arg Glu Asn Phe Glu Ile Leu Met
305                 310                 315                 320

Lys Leu Lys Glu Ser Leu Glu Leu Met Glu Leu Val Pro Gln Pro Leu
                325                 330                 335

Val Asp Ser Tyr Arg Gln Gln Gln Leu Leu Gln Arg Pro Ser His
            340                 345                 350

Leu Gln Pro Pro Ser Tyr Gly Pro Val Leu Ser Pro Met Asn Lys Val
        355                 360                 365

His Gly Gly Met Asn Lys Leu Pro Ser Val Asn Gln Leu Val Gly Gln
    370                 375                 380

Pro Pro Pro His Ser Ser Ala Ala Thr Pro Asn Leu Gly Pro Val Gly
```

```
                385                 390                 395                 400
Pro Gly Met Leu Asn Asn His Gly His Ala Val Pro Ala Asn Gly Glu
                    405                 410                 415
Met Ser Ser Ser His Ser Ala Gln Ser Met Val Ser Gly Ser His Cys
                    420                 425                 430
Thr Pro Pro Pro Tyr His Ala Asp Pro Ser Leu Val Ser Phe Leu
            435                 440                 445
Thr Gly Leu Gly Cys Pro Asn Cys Ile Glu Tyr Phe Thr Ser Gln Gly
        450                 455                 460
Leu Gln Ser Ile Tyr His Leu Gln Asn Leu Thr Ile Glu Asp Leu Gly
465                 470                 475                 480
Ala Leu Lys Ile Pro Glu Gln Tyr Arg Met Thr Ile Trp Arg Gly Leu
                485                 490                 495
Gln Asp Leu Lys Gln Gly His Asp Tyr Ser Thr Ala Gln Gln Leu Leu
                500                 505                 510
Arg Ser Ser Asn Ala Ala Thr Ile Ser Ile Gly Gly Ser Gly Glu Leu
            515                 520                 525
Gln Arg Gln Arg Val Met Glu Ala Val His Phe Arg Val Arg His Thr
        530                 535                 540
Ile Thr Ile Pro Asn Arg Gly Gly Pro Gly Gly Gly Pro Asp Glu Trp
545                 550                 555                 560
Ala Asp Phe Gly Phe Asp Leu Pro Asp Cys Lys Ala Arg Lys Gln Pro
                565                 570                 575
Ile Lys Glu Glu Phe Thr Glu Ala Glu Ile His
                580                 585

<210> SEQ ID NO 14
<211> LENGTH: 1521
<212> TYPE: DNA
<213> ORGANISM: Homo sapiens

<400> SEQUENCE: 14
atgctgtacg tcggtgaccc cgcacggcac ctcgccacgg cccagttcaa tctgctgagc     60
agcaccatgg accagatgag cagccgcgcg gcctcggcca gccctacac cccagagcac    120 gccgccagcg tgcccaccca ctcgccctac gcacaaccca gctccacctt cgacaccatg    180
tcgccggcgc ctgtcatccc ctccaacacc gactacccg acccccacca ctttgaggtc    240
actttccagc agtccagcac ggccaagtca gccacctgga cgtactcccc gctcttgaag    300
aaactctact gccagatcgc caagacatgc cccatccaga tcaaggtgtc caccccgcca    360
cccccaggca ctgccatccg ggccatgcct gtttacaaga aagcggagca cgtgaccgac    420
gtcgtgaaac gctgccccaa ccacgagctc ggggagggact caacgaagg acagtctgct    480 ccagccagcc acctcatccg cgtggaaggc aataatctct cgcagtatgt ggatgaccct    540
gtcaccggca ggcagagcgt cgtggtgccc tatgagccac acaggtggg gacggaattc    600 accaccatcc tgtacaactt catgtgtaac agcagctgtg tagggggcat gaaccggcgg    660
cccatcctca tcatcatcac cctggagatg cgggatgggc aggtgctggg ccgccggtcc    720
tttgagggcc gcatctgcgc ctgtcctggc gcgaccgaa agctgatga ggaccactac    780 cgggagcag aggccctgaa cgagagctcc gccaagaacg gggccgccag caagcgtgcc    840
ttcaagcaga gccccctgc cgtccccgcc cttggtgccg tgtgaagaa gcggcggcat    900 ggagacgagg acacgtacta ccttcaggtg cgaggccggg agaactttga gatcctgatg    960
aagctgaaag agagcctgga gctgatggag ttggtgccgc agccactggt ggactcctat   1020
```

-continued

```
cggcagcagc agcagctcct acagaggccg ccccgggatg ctcaacaacc atggccacgc    1080
agtgccagcc aacggcgaga tgagcagcag ccacagcgcc cagtccatgg tctcggggtc    1140
ccactgcact ccgccacccc cctaccacgc cgacccagc ctcgtcagga cctgggggcc     1200
ctgaagatcc ccgagcagta ccgcatgacc atctggcggg gcctgcagga cctgaagcag    1260
ggccacgact acagcaccgc gcagcagctg ctccgctcta gcaacgcggc caccatctcc    1320
atcggcggct caggggaact gcagcgccag cgggtcatgg aggccgtgca cttccgcgtg    1380
cgccacacca tcaccatccc caaccgcggc ggcccaggcg gcggccctga cgagtgggcg    1440
gacttcggct tcgacctgcc cgactgcaag gcccgcaagc agcccatcaa ggaggagttc    1500
acggaggccg agatccactg a                                              1521
```

<210> SEQ ID NO 15
<211> LENGTH: 506
<212> TYPE: PRT
<213> ORGANISM: Homo sapiens

<400> SEQUENCE: 15

```
Met Leu Tyr Val Gly Asp Pro Ala Arg His Leu Ala Thr Ala Gln Phe
1               5                   10                  15

Asn Leu Leu Ser Ser Thr Met Asp Gln Met Ser Ser Arg Ala Ala Ser
            20                  25                  30

Ala Ser Pro Tyr Thr Pro Glu His Ala Ala Ser Val Pro Thr His Ser
        35                  40                  45

Pro Tyr Ala Gln Pro Ser Ser Thr Phe Asp Thr Met Ser Pro Ala Pro
    50                  55                  60

Val Ile Pro Ser Asn Thr Asp Tyr Pro Gly Pro His His Phe Glu Val
65                  70                  75                  80

Thr Phe Gln Gln Ser Ser Thr Ala Lys Ser Ala Thr Trp Thr Tyr Ser
                85                  90                  95

Pro Leu Leu Lys Lys Leu Tyr Cys Gln Ile Ala Lys Thr Cys Pro Ile
            100                 105                 110

Gln Ile Lys Val Ser Thr Pro Pro Pro Gly Thr Ala Ile Arg Ala
        115                 120                 125

Met Pro Val Tyr Lys Lys Ala Glu His Val Thr Asp Val Val Lys Arg
    130                 135                 140

Cys Pro Asn His Glu Leu Gly Arg Asp Phe Asn Glu Gly Gln Ser Ala
145                 150                 155                 160

Pro Ala Ser His Leu Ile Arg Val Glu Gly Asn Asn Leu Ser Gln Tyr
                165                 170                 175

Val Asp Asp Pro Val Thr Gly Arg Gln Ser Val Val Pro Tyr Glu
            180                 185                 190

Pro Pro Gln Val Gly Thr Glu Phe Thr Thr Ile Leu Tyr Asn Phe Met
        195                 200                 205

Cys Asn Ser Ser Cys Val Gly Gly Met Asn Arg Arg Pro Ile Leu Ile
    210                 215                 220

Ile Ile Thr Leu Glu Met Arg Asp Gly Gln Val Leu Gly Arg Arg Ser
225                 230                 235                 240

Phe Glu Gly Arg Ile Cys Ala Cys Pro Gly Arg Asp Arg Lys Ala Asp
                245                 250                 255

Glu Asp His Tyr Arg Glu Gln Gln Ala Leu Asn Glu Ser Ser Ala Lys
            260                 265                 270

Asn Gly Ala Ala Ser Lys Arg Ala Phe Lys Gln Ser Pro Pro Ala Val
```

```
                275                 280                 285
Pro Ala Leu Gly Ala Gly Val Lys Lys Arg Arg His Gly Asp Glu Asp
    290                 295                 300
Thr Tyr Tyr Leu Gln Val Arg Gly Arg Glu Asn Phe Glu Ile Leu Met
305                 310                 315                 320
Lys Leu Lys Glu Ser Leu Glu Leu Met Glu Leu Val Pro Gln Pro Leu
                325                 330                 335
Val Asp Ser Tyr Arg Gln Gln Gln Leu Leu Gln Arg Pro Pro Arg
                340                 345                 350
Asp Ala Gln Gln Pro Trp Pro Arg Ser Ala Ser Gln Arg Arg Asp Glu
            355                 360                 365
Gln Gln Pro Gln Arg Pro Val His Gly Leu Gly Val Pro Leu His Ser
    370                 375                 380
Ala Thr Pro Leu Pro Arg Arg Pro Gln Pro Arg Gln Asp Leu Gly Ala
385                 390                 395                 400
Leu Lys Ile Pro Glu Gln Tyr Arg Met Thr Ile Trp Arg Gly Leu Gln
                405                 410                 415
Asp Leu Lys Gln Gly His Asp Tyr Ser Thr Ala Gln Gln Leu Leu Arg
            420                 425                 430
Ser Ser Asn Ala Ala Thr Ile Ser Ile Gly Gly Ser Gly Glu Leu Gln
    435                 440                 445
Arg Gln Arg Val Met Glu Ala Val His Phe Arg Val Arg His Thr Ile
450                 455                 460
Thr Ile Pro Asn Arg Gly Gly Pro Gly Gly Gly Pro Asp Glu Trp Ala
465                 470                 475                 480
Asp Phe Gly Phe Asp Leu Pro Asp Cys Lys Ala Arg Lys Gln Pro Ile
                485                 490                 495
Lys Glu Glu Phe Thr Glu Ala Glu Ile His
                500                 505

<210> SEQ ID NO 16
<211> LENGTH: 1870
<212> TYPE: DNA
<213> ORGANISM: Homo sapiens
<220> FEATURE:
<221> NAME/KEY: CDS
<222> LOCATION: 104..1867

<400> SEQUENCE: 16
tgcccggggc tgcgacggct gcagggaacc agacagcacc tacttcgacc ttccccagtc      60
aagccggggg aataatgagg tggtgggcgg aacggattcc agc atg gac gtc ttc     115
                                              Met Asp Val Phe
                                                1 cac ctg gag ggc atg act aca tct gtc atg gcc cag ttc aat ctg ctg     163
His Leu Glu Gly Met Thr Thr Ser Val Met Ala Gln Phe Asn Leu Leu
  5                  10                  15                  20 agc agc acc atg gac cag atg agc agc cgc gcg gcc tcg gcc agc ccc     211
Ser Ser Thr Met Asp Gln Met Ser Ser Arg Ala Ala Ser Ala Ser Pro
                 25                  30                  35 tac acc cca gag cac gcc gcc agc gtg ccc acc cac tcg ccc tac gca     259
Tyr Thr Pro Glu His Ala Ala Ser Val Pro Thr His Ser Pro Tyr Ala
         40                  45                  50 caa ccc agc tcc acc ttc gac acc atg tcg ccg gcg cct gtc atc ccc     307
Gln Pro Ser Ser Thr Phe Asp Thr Met Ser Pro Ala Pro Val Ile Pro
     55                  60                  65 tcc aac acc gac tac ccc gga ccc cac cac ttt gag gtc act ttc cag     355
Ser Asn Thr Asp Tyr Pro Gly Pro His His Phe Glu Val Thr Phe Gln
```

-continued

```
            70                  75                  80
cag tcc agc acg gcc aag tca gcc acc tgg acg tac tcc ccg ctc ttg      403
Gln Ser Ser Thr Ala Lys Ser Ala Thr Trp Thr Tyr Ser Pro Leu Leu
 85                  90                  95                 100 aag aaa ctc tac tgc cag atc gcc aag aca tgc ccc atc cag atc aag      451
Lys Lys Leu Tyr Cys Gln Ile Ala Lys Thr Cys Pro Ile Gln Ile Lys
                    105                 110                 115 gtg tcc acc ccg cca ccc cca ggc act gcc atc cgg gcc atg cct gtt      499
Val Ser Thr Pro Pro Pro Pro Gly Thr Ala Ile Arg Ala Met Pro Val
                120                 125                 130 tac aag aaa gcg gag cac gtg acc gac gtc gtg aaa cgc tgc ccc aac      547
Tyr Lys Lys Ala Glu His Val Thr Asp Val Val Lys Arg Cys Pro Asn
            135                 140                 145 cac gag ctc ggg agg gac ttc aac gaa gga cag tct gct cca gcc agc      595
His Glu Leu Gly Arg Asp Phe Asn Glu Gly Gln Ser Ala Pro Ala Ser
        150                 155                 160 cac ctc atc cgc gtg gaa ggc aat aat ctc tcg cag tat gtg gat gac      643
His Leu Ile Arg Val Glu Gly Asn Asn Leu Ser Gln Tyr Val Asp Asp
165                 170                 175                 180 cct gtc acc ggc agg cag agc gtc gtg gtg ccc tat gag cca cca cag      691
Pro Val Thr Gly Arg Gln Ser Val Val Val Pro Tyr Glu Pro Pro Gln
                185                 190                 195 gtg ggg acg gaa ttc acc acc atc ctg tac aac ttc atg tgt aac agc      739
Val Gly Thr Glu Phe Thr Thr Ile Leu Tyr Asn Phe Met Cys Asn Ser
                200                 205                 210 agc tgt gta ggg ggc atg aac cgg cgg ccc atc ctc atc atc acc          787
Ser Cys Val Gly Gly Met Asn Arg Arg Pro Ile Leu Ile Ile Thr
            215                 220                 225 ctg gag atg cgg gat ggg cag gtg ctg ggc cgc cgg tcc ttt gag ggc      835
Leu Glu Met Arg Asp Gly Gln Val Leu Gly Arg Arg Ser Phe Glu Gly
        230                 235                 240 cgc atc tgc gcc tgt cct ggc cgc gac cga aaa gct gat gag gac cac      883
Arg Ile Cys Ala Cys Pro Gly Arg Asp Arg Lys Ala Asp Glu Asp His
245                 250                 255                 260 tac cgg gag cag cag gcc ctg aac gag agc tcc gcc aag aac ggg gcc      931
Tyr Arg Glu Gln Gln Ala Leu Asn Glu Ser Ser Ala Lys Asn Gly Ala
                265                 270                 275 gcc agc aag cgt gcc ttc aag cag agc ccc cct gcc gtc ccc gcc ctt      979
Ala Ser Lys Arg Ala Phe Lys Gln Ser Pro Pro Ala Val Pro Ala Leu
                280                 285                 290 ggt gcc ggt gtg aag aag cgg cgg cat gga gac gag gac acg tac tac     1027
Gly Ala Gly Val Lys Lys Arg Arg His Gly Asp Glu Asp Thr Tyr Tyr
            295                 300                 305 ctt cag gtg cga ggc cgg gag aac ttt gag atc ctg atg aag ctg aaa     1075
Leu Gln Val Arg Gly Arg Glu Asn Phe Glu Ile Leu Met Lys Leu Lys
310                 315                 320 gag agc ctg gag ctg atg gag ttg gtg ccg cag cca ctg gtg gac tcc     1123
Glu Ser Leu Glu Leu Met Glu Leu Val Pro Gln Pro Leu Val Asp Ser
325                 330                 335                 340 tat cgg cag cag cag cag ctc cta cag agg ccg agt cac cta cag ccc     1171
Tyr Arg Gln Gln Gln Gln Leu Leu Gln Arg Pro Ser His Leu Gln Pro
                345                 350                 355 ccg tcc tac ggg ccg gtc ctc tcg ccc atg aac aag gtg cac ggg ggc     1219
Pro Ser Tyr Gly Pro Val Leu Ser Pro Met Asn Lys Val His Gly Gly
                360                 365                 370 atg aac aag ctg ccc tcc gtc aac cag ctg gtg ggc cag cct ccc ccg     1267
Met Asn Lys Leu Pro Ser Val Asn Gln Leu Val Gly Gln Pro Pro Pro
                375                 380                 385 cac agt tcg gca gct aca ccc aac ctg ggg ccc gtg ggc ccc ggg atg     1315
```

```
His Ser Ser Ala Ala Thr Pro Asn Leu Gly Pro Val Gly Pro Gly Met
    390                 395                 400 ctc aac aac cat ggc cac gca gtg cca gcc aac ggc gag atg agc agc    1363
Leu Asn Asn His Gly His Ala Val Pro Ala Asn Gly Glu Met Ser Ser
405                 410                 415                 420 agc cac agc gcc cag tcc atg gtc tcg ggg tcc cac tgc act ccg cca    1411
Ser His Ser Ala Gln Ser Met Val Ser Gly Ser His Cys Thr Pro Pro
                425                 430                 435 ccc ccc tac cac gcc gac ccc agc ctc gtc agt ttt tta aca gga ttg    1459
Pro Pro Tyr His Ala Asp Pro Ser Leu Val Ser Phe Leu Thr Gly Leu
            440                 445                 450 ggg tgt cca aac tgc atc gag tat ttc acc tcc caa ggg tta cag agc    1507
Gly Cys Pro Asn Cys Ile Glu Tyr Phe Thr Ser Gln Gly Leu Gln Ser
        455                 460                 465 att tac cac ctg cag aac ctg acc att gag gac ctg ggg gcc ctg aag    1555
Ile Tyr His Leu Gln Asn Leu Thr Ile Glu Asp Leu Gly Ala Leu Lys
    470                 475                 480 atc ccc gag cag tac cgc atg acc atc tgg cgg ggc ctg cag gac ctg    1603
Ile Pro Glu Gln Tyr Arg Met Thr Ile Trp Arg Gly Leu Gln Asp Leu
485                 490                 495                 500 aag cag ggc cac gac tac agc acc gcg cag cag ctg ctc cgc tct agc    1651
Lys Gln Gly His Asp Tyr Ser Thr Ala Gln Gln Leu Leu Arg Ser Ser
                505                 510                 515 aac gcg gcc acc atc tcc atc ggc ggc tca ggg gaa ctg cag cgc cag    1699
Asn Ala Ala Thr Ile Ser Ile Gly Gly Ser Gly Glu Leu Gln Arg Gln
            520                 525                 530 cgg gtc atg gag gcc gtg cac ttc cgc gtg cgc cac acc atc acc atc    1747
Arg Val Met Glu Ala Val His Phe Arg Val Arg His Thr Ile Thr Ile
        535                 540                 545 ccc aac cgc ggc ggc cca ggc ggc ggc cct gac gag tgg gcg gac ttc    1795
Pro Asn Arg Gly Gly Pro Gly Gly Gly Pro Asp Glu Trp Ala Asp Phe
    550                 555                 560 ggc ttc gac ctg ccc gac tgc aag gcc cgc aag cag ccc atc aag gag    1843
Gly Phe Asp Leu Pro Asp Cys Lys Ala Arg Lys Gln Pro Ile Lys Glu
565                 570                 575                 580 gag ttc acg gag gcc gag atc cac tga                                1870
Glu Phe Thr Glu Ala Glu Ile His
                585

<210> SEQ ID NO 17
<211> LENGTH: 588
<212> TYPE: PRT
<213> ORGANISM: Homo Sapiens

<400> SEQUENCE: 17

Met Asp Val Phe His Leu Glu Gly Met Thr Thr Ser Val Met Ala Gln
1               5                   10                  15

Phe Asn Leu Leu Ser Ser Thr Met Asp Gln Met Ser Ser Arg Ala Ala
            20                  25                  30

Ser Ala Ser Pro Tyr Thr Pro Glu His Ala Ala Ser Val Pro Thr His
        35                  40                  45

Ser Pro Tyr Ala Gln Pro Ser Ser Thr Phe Asp Thr Met Ser Pro Ala
    50                  55                  60

Pro Val Ile Pro Ser Asn Thr Asp Tyr Pro Gly Pro His His Phe Glu
65                  70                  75                  80

Val Thr Phe Gln Gln Ser Ser Thr Ala Lys Ser Ala Thr Trp Thr Tyr
            85                  90                  95

Ser Pro Leu Leu Lys Lys Leu Tyr Cys Gln Ile Ala Lys Thr Cys Pro
        100                 105                 110
```

```
Ile Gln Ile Lys Val Ser Thr Pro Pro Pro Gly Thr Ala Ile Arg
        115                 120                 125

Ala Met Pro Val Tyr Lys Lys Ala Glu His Val Thr Asp Val Val Lys
130                 135                 140

Arg Cys Pro Asn His Glu Leu Gly Arg Asp Phe Asn Glu Gly Gln Ser
145                 150                 155                 160

Ala Pro Ala Ser His Leu Ile Arg Val Glu Gly Asn Asn Leu Ser Gln
                165                 170                 175

Tyr Val Asp Asp Pro Val Thr Gly Arg Gln Ser Val Val Pro Tyr
                180                 185                 190

Glu Pro Pro Gln Val Gly Thr Glu Phe Thr Thr Ile Leu Tyr Asn Phe
            195                 200                 205

Met Cys Asn Ser Ser Cys Val Gly Gly Met Asn Arg Arg Pro Ile Leu
    210                 215                 220

Ile Ile Ile Thr Leu Glu Met Arg Asp Gly Gln Val Leu Gly Arg Arg
225                 230                 235                 240

Ser Phe Glu Gly Arg Ile Cys Ala Cys Pro Gly Arg Asp Arg Lys Ala
                245                 250                 255

Asp Glu Asp His Tyr Arg Glu Gln Gln Ala Leu Asn Glu Ser Ser Ala
                260                 265                 270

Lys Asn Gly Ala Ala Ser Lys Arg Ala Phe Lys Gln Ser Pro Pro Ala
            275                 280                 285

Val Pro Ala Leu Gly Ala Gly Val Lys Lys Arg Arg His Gly Asp Glu
        290                 295                 300

Asp Thr Tyr Tyr Leu Gln Val Arg Gly Arg Glu Asn Phe Glu Ile Leu
305                 310                 315                 320

Met Lys Leu Lys Glu Ser Leu Glu Leu Met Glu Leu Val Pro Gln Pro
                325                 330                 335

Leu Val Asp Ser Tyr Arg Gln Gln Gln Leu Leu Gln Arg Pro Ser
                340                 345                 350

His Leu Gln Pro Pro Ser Tyr Gly Pro Val Leu Ser Pro Met Asn Lys
            355                 360                 365

Val His Gly Gly Met Asn Lys Leu Pro Ser Val Asn Gln Leu Val Gly
        370                 375                 380

Gln Pro Pro Pro His Ser Ser Ala Ala Thr Pro Asn Leu Gly Pro Val
385                 390                 395                 400

Gly Pro Gly Met Leu Asn Asn His Gly His Ala Val Pro Ala Asn Gly
                405                 410                 415

Glu Met Ser Ser Ser His Ser Ala Gln Ser Met Val Ser Gly Ser His
                420                 425                 430

Cys Thr Pro Pro Pro Tyr His Ala Asp Pro Ser Leu Val Ser Phe
            435                 440                 445

Leu Thr Gly Leu Gly Cys Pro Asn Cys Ile Glu Tyr Phe Thr Ser Gln
        450                 455                 460

Gly Leu Gln Ser Ile Tyr His Leu Gln Asn Leu Thr Ile Glu Asp Leu
465                 470                 475                 480

Gly Ala Leu Lys Ile Pro Glu Gln Tyr Arg Met Thr Ile Trp Arg Gly
                485                 490                 495

Leu Gln Asp Leu Lys Gln Gly His Asp Tyr Ser Thr Ala Gln Gln Leu
                500                 505                 510

Leu Arg Ser Ser Asn Ala Ala Thr Ile Ser Ile Gly Gly Ser Gly Glu
            515                 520                 525
```

```
Leu Gln Arg Gln Arg Val Met Glu Ala Val His Phe Arg Val Arg His
        530                 535                 540
Thr Ile Thr Ile Pro Asn Arg Gly Gly Pro Gly Gly Gly Pro Asp Glu
545                 550                 555                 560
Trp Ala Asp Phe Gly Phe Asp Leu Pro Asp Cys Lys Ala Arg Lys Gln
                565                 570                 575
Pro Ile Lys Glu Glu Phe Thr Glu Ala Glu Ile His
                580                 585

<210> SEQ ID NO 18
<211> LENGTH: 1817
<212> TYPE: DNA
<213> ORGANISM: Homo sapiens

<400> SEQUENCE: 18
```

| | | | | | |
|---|---|---|---|---|---|
| atggcccagt | ccaccgccac | ctcccctgat | gggggcacca | cgtttgagca | cctctggagc | 60 |
| tctctggaac | agacagcac | ctacttcgac | cttccccagt | caagccgggg | gaataatgag | 120 |
| gtggtgggcg | aacggattc | cagcatggac | gtcttccacc | tggagggcat | gactacatct | 180 |
| gtcatggccc | agttcaatct | gctgagcagc | accatggacc | agatgagcag | ccgcgcggcc | 240 |
| tcggccagcc | cctacacccc | agagcacgcc | gccagcgtgc | ccacccactc | gccctacgca | 300 |
| caacccagct | ccaccttcga | caccatgtcg | ccggcgcctg | tcatcccctc | caacaccgac | 360 |
| taccccggac | ccaccacctt | tgaggtcact | ttccagcagt | ccagcacggc | caagtcagcc | 420 |
| acctggacgt | actccccgct | cttgaagaaa | ctctactgcc | agatcgccaa | gacatgcccc | 480 |
| atccagatca | aggtgtccac | cccgccaccc | ccaggcactg | ccatccgggc | catgcctgtt | 540 |
| tacaagaaag | cggagcacgt | gaccgacgtc | gtgaaacgct | gccccaacca | cgagctcggg | 600 |
| agggacttca | cgaaggaca | gtctgctcca | gccagccacc | tcatccgcgt | ggaaggcaat | 660 |
| aatctctcgc | agtatgtgga | tgaccctgtc | accggcaggc | agagcgtcgt | ggtgccctat | 720 |
| gagccaccac | aggtggggac | ggaattcacc | accatcctgt | acaacttcat | gtgtaacagc | 780 |
| agctgtgtag | gggcatgaa | ccggcggccc | atcctcatca | tcatcaccct | ggagatgcgg | 840 |
| gatgggcagg | tgctgggccg | ccggtccttt | gagggccgca | tctgcgcctg | tcctggccgc | 900 |
| gaccgaaaag | ctgatgagga | ccactaccgg | gagcagcagg | ccctgaacga | gagctccgcc | 960 |
| aagaacgggg | ccgccagcaa | gcgtgccttc | aagcagagcc | ccctgccgt | cccgcccctt | 1020 |
| ggtgccggtg | tgaagaagcg | gcggcatgga | gacgaggaca | cgtactacct | tcaggtgcga | 1080 |
| ggccgggaga | actttgagat | cctgatgaag | ctgaaagaga | gcctggagct | gatggagttg | 1140 |
| gtgccgcagc | cactggtgga | ctcctatcgg | cagcagcagc | agctcctaca | gaggccgagt | 1200 |
| cacctacagc | ccccgtccta | cgggccggtc | ctctcgccca | tgaacaaggt | gcacggggc | 1260 |
| atgaacaagc | tgccctccgt | caaccagctg | gtgggccagc | ctcccccgca | cagttcggca | 1320 |
| gctacacccca | acctggggcc | cgtgggcccc | gggatgctca | acaaccatgg | ccacgcagtg | 1380 |
| ccagccaacg | gcgagatgag | cagcagccac | agcgcccagt | ccatggtctc | ggggtcccac | 1440 |
| tgcactccgc | cacccccta | ccacgccgac | cccagcctcg | tcaggacctg | ggggccctga | 1500 |
| agatccccga | gcagtaccgc | atgaccatct | ggcgggcct | gcaggacctg | aagcagggcc | 1560 |
| acgactacag | caccgcgcag | cagctgctcc | gctctagcaa | cgcggccacc | atctccatcg | 1620 |
| gcggctcagg | gaactgcag | cgccagcggg | tcatggaggc | cgtgcacttc | cgcgtgcgcc | 1680 |
| acaccatcac | catccccaac | cgcggcggcc | caggcggcgg | ccctgacgag | tgggcggact | 1740 |
| tcggcttcga | cctgcccgac | tgcaaggccc | gcaagcagcc | catcaaggag | gagttcacgg | 1800 | aggccgagat ccactga                                                    1817

<210> SEQ ID NO 19
<211> LENGTH: 499
<212> TYPE: PRT
<213> ORGANISM: Homo sapiens

<400> SEQUENCE: 19

Met Ala Gln Ser Thr Ala Thr Ser Pro Asp Gly Gly Thr Thr Phe Glu
1               5                   10                  15

His Leu Trp Ser Ser Leu Glu Pro Asp Ser Thr Tyr Phe Asp Leu Pro
            20                  25                  30

Gln Ser Ser Arg Gly Asn Asn Glu Val Val Gly Gly Thr Asp Ser Ser
        35                  40                  45

Met Asp Val Phe His Leu Glu Gly Met Thr Thr Ser Val Met Ala Gln
50                  55                  60

Phe Asn Leu Leu Ser Ser Thr Met Asp Gln Met Ser Ser Arg Ala Ala
65                  70                  75                  80

Ser Ala Ser Pro Tyr Thr Pro Glu His Ala Ala Ser Val Pro Thr His
                85                  90                  95

Ser Pro Tyr Ala Gln Pro Ser Ser Thr Phe Asp Thr Met Ser Pro Ala
            100                 105                 110

Pro Val Ile Pro Ser Asn Thr Asp Tyr Pro Gly Pro His His Phe Glu
        115                 120                 125

Val Thr Phe Gln Gln Ser Ser Thr Ala Lys Ser Ala Thr Trp Thr Tyr
130                 135                 140

Ser Pro Leu Leu Lys Lys Leu Tyr Cys Gln Ile Ala Lys Thr Cys Pro
145                 150                 155                 160

Ile Gln Ile Lys Val Ser Thr Pro Pro Pro Gly Thr Ala Ile Arg
                165                 170                 175

Ala Met Pro Val Tyr Lys Lys Ala Glu His Val Thr Asp Val Val Lys
            180                 185                 190

Arg Cys Pro Asn His Glu Leu Gly Arg Asp Phe Asn Glu Gly Gln Ser
        195                 200                 205

Ala Pro Ala Ser His Leu Ile Arg Val Glu Gly Asn Asn Leu Ser Gln
    210                 215                 220

Tyr Val Asp Asp Pro Val Thr Gly Arg Gln Ser Val Val Pro Tyr
225                 230                 235                 240

Glu Pro Pro Gln Val Gly Thr Glu Phe Thr Thr Ile Leu Tyr Asn Phe
                245                 250                 255

Met Cys Asn Ser Ser Cys Val Gly Gly Met Asn Arg Arg Pro Ile Leu
            260                 265                 270

Ile Ile Ile Thr Leu Glu Met Arg Asp Gly Gln Val Leu Gly Arg Arg
        275                 280                 285

Ser Phe Glu Gly Arg Ile Cys Ala Cys Pro Gly Arg Asp Arg Lys Ala
    290                 295                 300

Asp Glu Asp His Tyr Arg Glu Gln Gln Ala Leu Asn Glu Ser Ser Ala
305                 310                 315                 320

Lys Asn Gly Ala Ala Ser Lys Arg Ala Phe Lys Gln Ser Pro Pro Ala
                325                 330                 335

Val Pro Ala Leu Gly Ala Gly Val Lys Lys Arg Arg His Gly Asp Glu
            340                 345                 350

Asp Thr Tyr Tyr Leu Gln Val Arg Gly Arg Glu Asn Phe Glu Ile Leu
        355                 360                 365

Met Lys Leu Lys Glu Ser Leu Glu Leu Met Glu Leu Val Pro Gln Pro
    370             375                 380

Leu Val Asp Ser Tyr Arg Gln Gln Gln Leu Leu Gln Arg Pro Ser
385                 390                 395                 400

His Leu Gln Pro Pro Ser Tyr Gly Pro Val Leu Ser Pro Met Asn Lys
                405                 410                 415

Val His Gly Gly Met Asn Lys Leu Pro Ser Val Asn Gln Leu Val Gly
            420                 425                 430

Gln Pro Pro His Ser Ser Ala Ala Thr Pro Asn Leu Gly Pro Val
        435                 440                 445

Gly Pro Gly Met Leu Asn Asn His Gly His Ala Val Pro Ala Asn Gly
    450                 455                 460

Glu Met Ser Ser Ser His Ser Ala Gln Ser Met Val Ser Gly Ser His
465                 470                 475                 480

Cys Thr Pro Pro Pro Tyr His Ala Asp Pro Ser Leu Val Arg Thr
                485                 490                 495

Trp Gly Pro

<210> SEQ ID NO 20
<211> LENGTH: 17
<212> TYPE: DNA
<213> ORGANISM: Artificial
<220> FEATURE:
<223> OTHER INFORMATION: primer

<400> SEQUENCE: 20
gcgagctgcc ctcggag                                                  17

<210> SEQ ID NO 21
<211> LENGTH: 19
<212> TYPE: DNA
<213> ORGANISM: Artificial
<220> FEATURE:
<223> OTHER INFORMATION: antisense primer

<400> SEQUENCE: 21
ggttctgcag gtgactcag                                                19

<210> SEQ ID NO 22
<211> LENGTH: 18
<212> TYPE: DNA
<213> ORGANISM: Artificial
<220> FEATURE:
<223> OTHER INFORMATION: primer

<400> SEQUENCE: 22
gccatgcctg tctacaag                                                 18

<210> SEQ ID NO 23
<211> LENGTH: 18
<212> TYPE: DNA
<213> ORGANISM: Artificial
<220> FEATURE:
<223> OTHER INFORMATION: antisense primer

<400> SEQUENCE: 23
accagctggt tgacggag                                                 18

<210> SEQ ID NO 24
<211> LENGTH: 21
<212> TYPE: DNA

```
<213> ORGANISM: Artificial
<220> FEATURE:
<223> OTHER INFORMATION: primer

<400> SEQUENCE: 24
gtcaaccagc tggtgggcca g                                              21

<210> SEQ ID NO 25
<211> LENGTH: 16
<212> TYPE: DNA
<213> ORGANISM: Artificial
<220> FEATURE:
<223> OTHER INFORMATION: antisense primer

<400> SEQUENCE: 25
gtggatctcg gcctcc                                                    16

<210> SEQ ID NO 26
<211> LENGTH: 17
<212> TYPE: DNA
<213> ORGANISM: Artificial
<220> FEATURE:
<223> OTHER INFORMATION: primer

<400> SEQUENCE: 26
aggccggcgt ggggaag                                                   17

<210> SEQ ID NO 27
<211> LENGTH: 19
<212> TYPE: DNA
<213> ORGANISM: Artificial
<220> FEATURE:
<223> OTHER INFORMATION: antisense primer

<400> SEQUENCE: 27
cttggcgatc tggcagtag                                                 19

<210> SEQ ID NO 28
<211> LENGTH: 17
<212> TYPE: DNA
<213> ORGANISM: Artificial
<220> FEATURE:
<223> OTHER INFORMATION: primer

<400> SEQUENCE: 28
gcggccacga ccgtgac                                                   17

<210> SEQ ID NO 29
<211> LENGTH: 18
<212> TYPE: DNA
<213> ORGANISM: Artificial
<220> FEATURE:
<223> OTHER INFORMATION: antisense primer

<400> SEQUENCE: 29
ggcagcttgg gtctctgg                                                  18

<210> SEQ ID NO 30
<211> LENGTH: 18
<212> TYPE: DNA
<213> ORGANISM: Artificial
<220> FEATURE:
<223> OTHER INFORMATION: primer

<400> SEQUENCE: 30
ctgtacgtcg gtgacccc                                                  18
```

```
<210> SEQ ID NO 31
<211> LENGTH: 18
<212> TYPE: DNA
<213> ORGANISM: Artificial
<220> FEATURE:
<223> OTHER INFORMATION: antisense primer

<400> SEQUENCE: 31
tcagtggatc tcggcctc                                                 18

<210> SEQ ID NO 32
<211> LENGTH: 18
<212> TYPE: DNA
<213> ORGANISM: Artificial
<220> FEATURE:
<223> OTHER INFORMATION: primer

<400> SEQUENCE: 32
aggggacgca gcgaaacc                                                 18

<210> SEQ ID NO 33
<211> LENGTH: 19
<212> TYPE: DNA
<213> ORGANISM: Artificial
<220> FEATURE:
<223> OTHER INFORMATION: antisense primer

<400> SEQUENCE: 33
ccatcagctc caggctctc                                                19

<210> SEQ ID NO 34
<211> LENGTH: 18
<212> TYPE: DNA
<213> ORGANISM: Artificial
<220> FEATURE:
<223> OTHER INFORMATION: antisense primer

<400> SEQUENCE: 34
ccaggacagg cgcagatg                                                 18

<210> SEQ ID NO 35
<211> LENGTH: 19
<212> TYPE: DNA
<213> ORGANISM: Artificial
<220> FEATURE:
<223> OTHER INFORMATION: antisense primer

<400> SEQUENCE: 35
gatgaggtgg ctggctgga                                                19

<210> SEQ ID NO 36
<211> LENGTH: 19
<212> TYPE: DNA
<213> ORGANISM: Artificial
<220> FEATURE:
<223> OTHER INFORMATION: antisense primer

<400> SEQUENCE: 36
tggtcaggtt ctgcaggtg                                                19

<210> SEQ ID NO 37
<211> LENGTH: 18
<212> TYPE: DNA
<213> ORGANISM: Artificial
<220> FEATURE:
```

```
<223> OTHER INFORMATION: primer

<400> SEQUENCE: 37
cacctactcc agggatgc                                                      18

<210> SEQ ID NO 38
<211> LENGTH: 21
<212> TYPE: DNA
<213> ORGANISM: Artificial
<220> FEATURE:
<223> OTHER INFORMATION: antisense primer

<400> SEQUENCE: 38
aggaaaatag aagcgtcagt c                                                  21

<210> SEQ ID NO 39
<211> LENGTH: 18
<212> TYPE: DNA
<213> ORGANISM: Artificial
<220> FEATURE:
<223> OTHER INFORMATION: primer

<400> SEQUENCE: 39
caggcccact tgcctgcc                                                      18

<210> SEQ ID NO 40
<211> LENGTH: 19
<212> TYPE: DNA
<213> ORGANISM: Artificial
<220> FEATURE:
<223> OTHER INFORMATION: antisense primer

<400> SEQUENCE: 40
ctgtccccaa gctgatgag                                                     19

<210> SEQ ID NO 41
<211> LENGTH: 15
<212> TYPE: DNA
<213> ORGANISM: Artificial
<220> FEATURE:
<223> OTHER INFORMATION: primer

<400> SEQUENCE: 41
cccccccccc ccccd                                                         15

<210> SEQ ID NO 42
<211> LENGTH: 16
<212> TYPE: DNA
<213> ORGANISM: Artificial
<220> FEATURE:
<223> OTHER INFORMATION: primer

<400> SEQUENCE: 42
cccccccccc cccccd                                                        16

<210> SEQ ID NO 43
<211> LENGTH: 1400
<212> TYPE: DNA
<213> ORGANISM: Cebus apella

<400> SEQUENCE: 43
ggggctccgg ggacacttgg cgtccgggct ggaagcgtgc tttccaagac ggtgacacgc         60
ttccctgagg attggcagcc agactgctta cgggtcactg ccatggagga gccgcagtca        120
gatcccagca tcgagccccc tctgagtcag gaaacatttt cagacctatg gaaactactt       180
```

```
cctgaaaaca acgttctgtc ccccttgccg tcccaagcgg tggatgattt gatgctctct    240
ccggatgatc ttgcacaatg gttaactgaa gacccaggtc cagatgaagc tcccagaatg    300
tcagaggctg ctccccacat ggccccccaca ccagcagctc ctacaccggc ggcccctgca    360
ccagccccct cctggcccct gtcatcctct gtcccttccc agaaaaccta ccacggcagc    420
tacggtttcc gtctgggctt cctgcattct ggaacagcca agtctgtgac ttgcacgtac    480
tcccctgacc tcaacaagat gttttgccag ctggccaaga cctgccccgt gcagctgtgg    540
gttgattcca caccccccgcc cggcagccgc gtccgcgcca tggccatcta caagcagtca    600
cagcacatga ctgaggtcgt gaggcgctgc ccccaccatg agcgctgctc agacagcgat    660
ggactggccc ctcctcaaca tcttatccga gtggaaggaa atttgcgtgt ggagtattcg    720
gatgacagaa acacttttcg acatagtgtg gtggtgccct atgagccgcc tgaggttggc    780
tctgactgta ccaccatcca ctacaactac atgtgtaaca gttcctgcat gggcggcatg    840
aaccggaggc ccatcctcac aattatcaca ctggaagact ccagtggtaa tctactggga    900
cggaacagct ttgaggtgcg agtttgtgcc tgtcctggga gagaccggcg cacagaggaa    960
gagaatttcc gcaagaaagg ggagccttgc cacgagctgc cccctgggag cactaagcga   1020
gcactgccca acaaccacag ctcctctccc cagccaaaga gaaaaccact ggatggagaa   1080
tatttcaccc ttcagatccg cgggcgtgag cgcttcgaga tgttccgaga gctgaatgag   1140
gccttggaac tcaaggatgc ccaggctggg aaagagccag cggggagcag ggctcactcc   1200
agccacctga agtccaagaa ggggcaatct acctcccgcc ataaaaaatt catgttcaag   1260
acagagggc ctgactcaga ctgacattct cagcttcttg ttcccccact gagcctccca   1320
cccccatctc tccctcccct gccattttga gttctgggtc tttaaaccct tgcttgcaat   1380
aggtgtgtgt cagaagcaaa                                                1400
```

<210> SEQ ID NO 44
<211> LENGTH: 393
<212> TYPE: PRT
<213> ORGANISM: Cebus apella

<400> SEQUENCE: 44

```
Met Glu Glu Pro Gln Ser Asp Pro Ser Ile Glu Pro Pro Leu Ser Gln
  1               5                  10                  15

Glu Thr Phe Ser Asp Leu Trp Lys Leu Leu Pro Glu Asn Asn Val Leu
             20                  25                  30

Ser Pro Leu Pro Ser Gln Ala Val Asp Asp Leu Met Leu Ser Pro Asp
         35                  40                  45

Asp Leu Ala Gln Trp Leu Thr Glu Asp Pro Gly Pro Asp Glu Ala Pro
     50                  55                  60

Arg Met Ser Glu Ala Ala Pro His Met Ala Pro Thr Pro Ala Ala Pro
 65                  70                  75                  80

Thr Pro Ala Ala Pro Ala Pro Ala Pro Ser Trp Pro Leu Ser Ser Ser
                 85                  90                  95

Val Pro Ser Gln Lys Thr Tyr His Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Asp Leu Asn Lys Met Phe Cys Gln Leu Ala Lys Thr Cys Pro Val Gln
    130                 135                 140

Leu Trp Val Asp Ser Thr Pro Pro Pro Gly Ser Arg Val Arg Ala Met
```

```
                145                 150                 155                 160
Ala Ile Tyr Lys Gln Ser Gln His Met Thr Glu Val Val Arg Arg Cys
                    165                 170                 175

Pro His His Glu Arg Cys Ser Asp Ser Asp Gly Leu Ala Pro Pro Gln
                180                 185                 190

His Leu Ile Arg Val Glu Gly Asn Leu Arg Val Glu Tyr Ser Asp Asp
                195                 200                 205

Arg Asn Thr Phe Arg His Ser Val Val Pro Tyr Glu Pro Pro Glu
            210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
                260                 265                 270

Arg Val Cys Ala Cys Pro Gly Arg Asp Arg Arg Thr Glu Glu Glu Asn
                275                 280                 285

Phe Arg Lys Lys Gly Glu Pro Cys His Glu Leu Pro Pro Gly Ser Thr
            290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
                340                 345                 350

Ala Gln Ala Gly Lys Glu Pro Ala Gly Ser Arg Ala His Ser Ser His
            355                 360                 365

Leu Lys Ser Lys Lys Gly Gln Ser Thr Ser Arg His Lys Lys Phe Met
            370                 375                 380

Phe Lys Thr Glu Gly Pro Asp Ser Asp
385                 390

<210> SEQ ID NO 45
<211> LENGTH: 393
<212> TYPE: PRT
<213> ORGANISM: Homo sapiens

<400> SEQUENCE: 45

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
                20                  25                  30

Ser Pro Leu Pro Ser Gln Ala Met Asp Asp Leu Met Leu Ser Pro Asp
            35                  40                  45

Asp Ile Glu Gln Trp Phe Thr Glu Asp Pro Gly Pro Asp Glu Ala Pro
        50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125
```

```
Ala Leu Asn Lys Met Phe Cys Gln Leu Ala Lys Thr Cys Pro Val Gln
        130                 135                 140

Leu Trp Val Asp Ser Thr Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Pro Tyr Glu Pro Pro Glu
210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Asn
275                 280                 285

Leu Arg Lys Lys Gly Glu Pro His His Glu Leu Pro Pro Gly Ser Thr
290                 295                 300

Lys Arg Ala Leu Pro Asn Asn Thr Ser Ser Ser Pro Gln Pro Lys Lys
305                 310                 315                 320

Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Gln Gly Lys Glu Pro Gly Gly Arg Ser Ala His Ser Ser His
            355                 360                 365

Leu Lys Ser Lys Lys Gly Gln Ser Thr Ser Arg His Lys Lys Leu Met
        370                 375                 380

Phe Lys Thr Glu Gly Pro Asp Ser Asp
385                 390

<210> SEQ ID NO 46
<211> LENGTH: 889
<212> TYPE: DNA
<213> ORGANISM: Homo sapiens

<400> SEQUENCE: 46
cacctactcc agggatgccc caggcaggcc cacttgcctg ccgcccccac cgaggctgtc      60
acaggaggac agagcacgag ttcccagggt gctcaggtgt cattccttcc ttcctgcaga     120
gcgagctgcc ctcggaggcc ggcgtgggga agatggccca gtccaccgcc acctcccctg     180 atggggcac cacgtttgag cacctctgga gctctctgtg agtgcgcttg ctggccaga      240 gctgggggcc ccctgggag gcactctggg ctagcctcag ccaccttcgc tgggctaact     300
gggccagagc aggagggtg gccccgggag gactctgggc tagccccagc caccctcact     360
gagactttgg gctaaacttg gcaaccctca ctgggattct gggctagcct cgaccaccct     420
tgctgcacta actggaccag agcaggagag gtggctccac actagtcttg ggctagcctt     480
agccaccctc atcagcttgg ggacagggcg gtcggaggg gcaggaaga gggactgctg      540 ccctaggcct tccctgggga tgcaggacca aaattcagac tctttttctct ggccagctct    600
```

| | |
|---|---|
| ggagagggcc catggccagc agaggcccag aataacagag cccatgactg gctctgcctc | 660 |
| tctggcactc acagcagccc tggaatggca ggtggaggac agagatggga tgagagggaa | 720 |
| tgggaagggc aggagacgta ggcctcacca ggagtctcag gctagccttg agctctgggc | 780 |
| ctgggaggta ttggggtgac acccaaactg gggactgacg cttctatttt cctctccctg | 840 |
| ccccagggaa ccagacagca cctacttcga ccttccccag tcaagccgg | 889 |

```
<210> SEQ ID NO 47
<211> LENGTH: 23
<212> TYPE: DNA
<213> ORGANISM: Artificial
<220> FEATURE:
<223> OTHER INFORMATION: primer comprising BamHI site

<400> SEQUENCE: 47
```

| | |
|---|---|
| gatccgggcc cttttttttt ttt | 23 |

```
<210> SEQ ID NO 48
<211> LENGTH: 20
<212> TYPE: DNA
<213> ORGANISM: Artificial
<220> FEATURE:
<223> OTHER INFORMATION: primer comprising ApaI site

<400> SEQUENCE: 48
```

| | |
|---|---|
| aaaaaaaaaa aaagggcccg | 20 |

```
<210> SEQ ID NO 49
<211> LENGTH: 26
<212> TYPE: DNA
<213> ORGANISM: Artificial
<220> FEATURE:
<223> OTHER INFORMATION: primer comprising Kpn I site

<400> SEQUENCE: 49
```

| | |
|---|---|
| actggtaccg cgagctgccc tcggag | 26 |

```
<210> SEQ ID NO 50
<211> LENGTH: 28
<212> TYPE: DNA
<213> ORGANISM: Artificial
<220> FEATURE:
<223> OTHER INFORMATION: antisense primer comprising Xba I site

<400> SEQUENCE: 50
```

| | |
|---|---|
| gactctagag gttctgcagg tgactcag | 28 |

```
<210> SEQ ID NO 51
<211> LENGTH: 19
<212> TYPE: DNA
<213> ORGANISM: Artificial
<220> FEATURE:
<223> OTHER INFORMATION: primer

<400> SEQUENCE: 51
```

| | |
|---|---|
| gagcatgtga ccgacattg | 19 |

```
<210> SEQ ID NO 52
<211> LENGTH: 30
<212> TYPE: DNA
<213> ORGANISM: Artificial
<220> FEATURE:
<223> OTHER INFORMATION: primer comprising BamHI site

<400> SEQUENCE: 52
```

```
tttggatccg tcaaccagct ggtgggccag                                      30

<210> SEQ ID NO 53
<211> LENGTH: 25
<212> TYPE: DNA
<213> ORGANISM: Artificial
<220> FEATURE:
<223> OTHER INFORMATION: antisense primer comprising a Sal I site

<400> SEQUENCE: 53
aaagtcgacg tggatctcgg cctcc                                           25

<210> SEQ ID NO 54
<211> LENGTH: 27
<212> TYPE: DNA
<213> ORGANISM: Artificial
<220> FEATURE:
<223> OTHER INFORMATION: primer

<400> SEQUENCE: 54
tatctcgagc tgtacgtcgg tgacccc                                         27

<210> SEQ ID NO 55
<211> LENGTH: 27
<212> TYPE: DNA
<213> ORGANISM: Artificial
<220> FEATURE:
<223> OTHER INFORMATION: antisense primer

<400> SEQUENCE: 55
atatctagat cagtggatct cggcctc                                         27
```